US006413233B1

(12) United States Patent
Sites et al.

(10) Patent No.: US 6,413,233 B1
(45) Date of Patent: Jul. 2, 2002

(54) PERFUSION HYPERTHERMIA TREATMENT SYSTEM AND METHOD

(75) Inventors: Jeffrey P. Sites, Plymouth; Philip R. Glassel, Stacy; Michael D. Miller, St. Anthony; Clark B. Norgaard, Golden Valley; Thomas A. Roman, St. Anthony; Dale J. Ziebarth, White Bear Township, all of MN (US)

(73) Assignee: BioThermics, Inc., Minneapolis, MN (US)

(*) Notice: Subject to any disclaimer, the term of this patent is extended or adjusted under 35 U.S.C. 154(b) by 0 days.

(21) Appl. No.: 09/480,088

(22) Filed: Jan. 10, 2000

Related U.S. Application Data

(60) Continuation of application No. 09/042,382, filed on Mar. 13, 1998, now abandoned, which is a division of application No. 08/516,580, filed on Aug. 18, 1995, now Pat. No. 5,730,720.

(51) Int. Cl.[7] .......................... A61M 37/00; A61F 7/12; A61A 1/00; G06F 7/02; C02F 1/00
(52) U.S. Cl. .................. 604/6.13; 604/4.01; 604/28; 604/113; 422/46; 601/3; 210/742; 706/924; 714/819
(58) Field of Search ............................. 604/4.01, 5.01, 604/6.13, 28, 500, 503, 27, 113–114, 65–67; 601/1, 3; 606/27; 600/300, 301, 306, 363, 366, 504; 210/739, 742, 252, 259–261, 256, 258, 257.1–257.2, 282, 321.6; 422/44, 46, 82, 12; 128/905, 898, 923, 924; 73/863.11; 165/200, 201, 205, 177, 287–289, 293; 706/45–47, 52, 55, 924, 932, 934; 714/25–26, 37–43, 418, 819, 822–824

(56) References Cited

U.S. PATENT DOCUMENTS

| 3,140,716 A | 7/1964 | Harrison et al. ............. 128/399 |
| 3,353,491 A | 11/1967 | Bastian ....................... 103/149 |

(List continued on next page.)

FOREIGN PATENT DOCUMENTS

| FR | 2631241 | 11/1989 |
| JP | 63165958 | 7/1988 |
| WO | 94/03216 | 2/1994 |
| WO | 94/11093 | 5/1994 |

OTHER PUBLICATIONS

Alonso, K., et al., "Systemic hyperthermia in the treatment of HIV–related Kaposi's sarcoma. A phase I study.", *Biomed & Pharmacother., vol. 46*, 21–24, (1992).

(List continued on next page.)

*Primary Examiner*—Angela D. Sykes
*Assistant Examiner*—Patricia Bianco
(74) *Attorney, Agent, or Firm*—Schwegman, Lundberg, Woessner & Kluth, P.A.

(57) ABSTRACT

Method and apparatus to automatically monitor and control a perfusion hyperthermia treatment using a system including one or more programmed computers, and mechanical and sensor subsystems. The system includes a fluid path between a patient and an external fluid-treatment subsystem, wherein control of the external fluid-treatment subsystem includes feedback from sensors coupled to the patient. The resulting integrated system provides automated monitoring and control of the patient, the external fluid-treatment subsystem, and the treatment. In one embodiment, the fluid passing between the patient and the external fluid-treatment subsystem is blood. In one embodiment, an apparatus and method are provided for using a computerized system for a perfusion hyper/hypothermia treatment of a patient which obtains a body fluid having a temperature. A plurality of temperature signals representative of temperatures at each of a plurality of patient locations on or within the patient are coupled to the computer system. Measured temperatures are compared to a set of stored parameters in the computer system to generate a comparison value which controls a change in the temperature of the body fluid. The body fluid is then perfused into the patient to either warm, cool, or maintain the current temperature of the patient. In one such embodiment, the body fluid is blood withdrawn from the patient. In another such embodiment, the body fluid is saline.

21 Claims, 35 Drawing Sheets

U.S. PATENT DOCUMENTS

| | | | | |
|---|---|---|---|---|
| 4,158,693 A | | 6/1979 | Reed et al. | 422/46 |
| 4,181,132 A | | 1/1980 | Parks | 128/399 |
| 4,190,053 A | | 2/1980 | Sterzer | 128/399 |
| 4,298,006 A | | 11/1981 | Parks | 128/399 |
| 4,397,314 A | | 8/1983 | Vaguine | 128/399 |
| 4,398,535 A | | 8/1983 | Guibert | 128/399 |
| 4,416,280 A | | 11/1983 | Carpenter et al. | 128/399 |
| 4,447,237 A | | 5/1984 | Frisch et al. | 604/175 |
| 4,476,867 A | | 10/1984 | Parks | 128/400 |
| 4,479,798 A | | 10/1984 | Parks | 604/175 |
| 4,572,190 A | | 2/1986 | Azam et al. | 128/399 |
| 4,617,931 A | | 10/1986 | Dory | 128/328 |
| 4,658,828 A | | 4/1987 | Dory | 128/660 |
| 4,662,435 A | | 5/1987 | Bohlin | 165/74 |
| 4,667,482 A | | 5/1987 | Kriekels | 62/238.6 |
| 4,669,475 A | | 6/1987 | Turner | 128/399 |
| 4,719,919 A | | 1/1988 | Marchosky et al. | 128/401 |
| 4,735,558 A | | 4/1988 | Kienholz et al. | 417/477 |
| 4,854,324 A | | 8/1989 | Hirschman et al. | 128/655 |
| 4,950,225 A | | 8/1990 | Davidner et al. | 604/4 |
| 5,026,365 A | | 6/1991 | Rossini et al. | 604/891.1 |
| 5,080,101 A | | 1/1992 | Dory | 120/660.03 |
| 5,080,645 A | | 1/1992 | Hanig | 604/4 |
| 5,104,373 A | | 4/1992 | Davidner et al. | 604/4 |
| 5,116,307 A | | 5/1992 | Collins | 422/24 |
| 5,133,932 A | | 7/1992 | Gunn et al. | 422/24 |
| 5,150,711 A | | 9/1992 | Dory | 129/660.03 |
| 5,180,896 A | * | 1/1993 | Gibby et al. | 219/10.55 |
| 5,188,738 A | | 2/1993 | Kaali et al. | 210/748 |
| 5,197,466 A | | 3/1993 | Marchosky et al. | 128/399 |
| 5,213,483 A | | 5/1993 | Flaherty et al. | 417/477 |
| 5,254,094 A | | 10/1993 | Starkey et al. | 604/113 |
| 5,261,874 A | | 11/1993 | Castle | 604/4 |
| 5,354,277 A | * | 10/1994 | Guzman et al. | 604/113 |
| 5,385,540 A | | 1/1995 | Abbott et al. | 604/4 |
| 5,391,142 A | * | 2/1995 | Sites et al. | 604/4 |
| 5,429,594 A | | 7/1995 | Castle | 604/4 |
| 5,437,278 A | * | 8/1995 | Wilk | |
| 5,492,109 A | | 2/1996 | Hirschl et al. | 128/201.21 |
| 5,494,822 A | * | 2/1996 | Sadri | |
| 5,674,190 A | * | 10/1997 | Kelly | 604/4 |
| 5,730,720 A | * | 3/1998 | Sites et al. | 604/27 |
| 5,752,813 A | | 5/1998 | Tyner et al. | 417/477.2 |
| 5,817,045 A | * | 10/1998 | Sever, Jr. | |

OTHER PUBLICATIONS

Alonso, K., et al., "Whole–Body Hyperthermia and the Augmentation of Cellular Cytotoxic Responses in the Treatment of Acquired Immune Deficiency Syndrome", *Southern Medical Assn's Annual Conference and Conjoint Meeting of the American Society of Clinical Hyperthermic Oncology, Abstract/Presentation*, S142, (1995).

Ash, S.R., et al., "Safety of Whole Body Hyperthermia (WBHT) with Hemodiabsorption in Treatment of AIDS", *ASAIO 41st Annual Conference Abstracts, vol. 41(1)*, 85, (1995).

Ash, S.R., et al., "The BioLogic–HT Sorbent System Maintains Normal Blood Chemistries during Whole Body Hyperthermia (WBHT)", *ASAIO 40th Annual Conference, Poster Presentation and Abstract*, (1994).

DeMoss, J.L., et al., "Hyperthermia in the Treatment of Cancer", *Journal of Extra–Corporeal Technology, vol. 17(1)*, 37–43, (1985).

Dietzel, F., "Tumortherapy with Hyperthermia", *Recent Results in Cancer Research, vol. 86, Springer–Verlag, Berlin*, 177–190, (1983).

Filippo, F., et al., "The Role of Hyperthermic Perfusion in the Treatment of Tumors of the Extremities", *Consensus on Hyperthermia for the 1990s, Plenum Press, New York*, 223–234, (1990).

Gabriele, P., et al., "Interstitial Hyperthermia: Technical Problems and Methodology", *Consensus on Hyperthermia for the 1990s, Plenum Press, New York*, 121–127, (1990).

Galletti, P.M., et al., "Rotary Pumps, Reciprocating Pumps, Elements of Extracorporeal Circulation", *Heart–Lung Bypass—Principles and Techniques of Extracorporeal Circulation, Grune & Stratton, New York*, 131–170, (1962).

Galletti, P.M., et al., "Theory of Blood Pumps", *Heart–Lung Bypass—Principles and Techniques of Extracorporeal Circulation, Grune & Stratton, New York*, 121–130, (1962).

Gautherie, M.(., "Whole Body Hyperthermia: Biological and Clinical Aspects", *Springer–Verlag*, (1992).

Ghussen, F., et al., "The Limit of Hyperthermic Strain on Skeletal Muscle Tissue During Regional Perfusion", *Research in Experimental Medicine, vol. 184, Springer–Verlag*, 115–123, (1984).

Groom, R.C., et al., "Hyperthermia Cancer Treatment: Systemic Hyperthermia and Isolated Limb Perfusion", *Proceedings of the American Academy of Cardiovascular Perfusion, vol. 8*, 105–111, (Sep., 1987).

Koga, S., et al., "Extracorporeally Induced Total Body Hyperthermia for Disseminated Cancer", *Consensus on Hyperthermia for the 1990s, Plenum Press, New York*, 177–178, (1990).

Koga, S., et al., "Prophylactic Therapy for Peritoneal Recurrence of Gastric Cancer by Continuous Hyperthermic Peritoneal Perfusion with Mitomycin C", *Cancer, vol. 61*, 232–237, (Jan., 1988).

Koops, H.S., et al., "Regionale Perfusionbehandlung bei primaren malignen Melanomen der Extremitaten", *Der Hautarzt, vol. 33, Springer–Verlag*, 506–510, (1982).

Krementz, E.T., "Chemotherapy of Melanoma of the Extremities by Perfusion: Fourteen Years Clinical Experience", *Annual Surgery, vol. 175(6)*, 900–917, (Jun., 1972).

Marchosky, J., et al., "Conductive Interstitial Hyperthermia: A New Modality for Treatment of Intracranial Tumors", *Consensus on Hyperthermia for the 1990s, Plenum Press, New York*, 129–143, (1990).

McLaren, J.R., "The Basis for Hyperthermia Becoming the Fourth Cancer Treatment Modality in the 1990's", *Consensus on Hyperthermia for the 1990s, Plenum Press, New York*, 21–36, (1990).

Osinsky, S., et al., "Procedures for Improving Therapeutic Gain", *Consensus on Hyperthermia for the 1990s, Plenum Press, New York*, 251–270, (1990).

Pace, M., et al., "Control of the Physical Parameters in Local Electromagnetic Hyperthermia", *Consensus on Hyperthermia for the 1990s, Plenum Press, New York*, 297–304, (1990).

Pace, M., et al., "Thermal Induction and Temperature Control in the Hyperthermic Antiblastic Regional Perfusion with Extracorporeal Circulation", *Consensus on Hyperthermia for the 1990s, Plenum Press, New York*, 399–403, (1990).

Parks, L.C., et al., "Systemic Hyperthermia by Extracorporeal Induction: Techniques and Results", *Hyperthermia and Cancer Therapy*, 407–446, (1983).

Parks, L.C., et al., "Treatment of far–advanced bronchogenic carcinoma by extracorporeally induced systemic hyperthermia", *Journal of Thoracic and Cardiovascular Surgery, vol. 78(6)*, 883–892, (1979).

Pontiggia, P., et al., "Whole–body Hyperthermia Followed by Beta Carotene Supplementation in Patients with Acquired Immune Deficiency Syndrome (AIDS)", *Southern Medical Assn's Annual Conference, and Conjoint Meeting of the American Society of Clinical Hyperthermic Oncology*, Abstract, S142, (1995).

Reed, C.C., et al., "Blood Pumps", *Cardiopulmonary Bypass, Texas Medical Press, Inc.,* Houston, TX, 376–378, (1985).

Reed, C.C., et al., "Heat Exchangers and Hypothermia", *Cardiopulmonary Bypass, Texas Medical Press, Inc., Houston, TX,* 320–328, (1985).

Sapir, A., et al., "Extracorporeal Whole–body Hyperthermia (WBHT) to Treat Human Immunodeficiency Virus (HIV) Infection Using the Biologic–HT", *Southern Medical Assn's Annual Conference, and Conjoint Meeting of the American Society of Clinical Hyperthermic Oncology*, Abstract/presentation, S144, (1995).

Schecterle, L.M., et al., "Canine Experimentation with Low Flow Extracorporeal Whole–body Hyperthermia", *Southern Medical Assn's Annual Conference, and Conjoint Meeting of the American Society of Clinical Hyperthermic Oncology, Absract*, S143, (1995).

Schecterle, L.M., et al., "Rate of Rise Using a Hot Air Whole–Body Hyperthermia Device", *Southern Medical Assn's Annual Conference, and Conjoint Meeting of the American Society of Clinical Hyperthemic Oncology*, Abstract S143, (1995).

Shidnia, H., et al., "Consensus of Hyperthermia for the 1990s", *Consensus on Hyperthermia for the 1990s, Plenum Press, New York,* 47–49, (1990).

Shidnia, H., et al., "The Use of Local Microwave Hyperthermia in Treatment of Head and Neck Tumors: Second Primary Site", *Southern Medical Assn's Annual Conference, and Conjoint Meeting of the American Society of Clinical Hyperthermic Oncology*, Abstract/presentation, S141, (1995).

Sites, J., "System Perfusion Hyperthermia for the Treatment of Cancer and HIV–Related Diseases", *6th European Congress on Extracorporeal Circulation Technology*, Waterloo, Belgium, (Jun. 7–10, 1995).

Sites, J., "The use of Extracorporeal Hyperthermia in an HIV–Infected Patient", *Case Reports I: Clinical Sutides in Extracorporeal Circulation, The Pref Press, Perfusion Research and Education Foundation,* 217–225, (1994).

Sites, J., et al., "A Computer Assisted Hyperthermia Perfusion System", *ASAIO 41st Annual Meeting,* Poster presentation, (May 4–6, 1995).

Storm, F.K., et al., "Value of Therapeutic Hyperthermic Limb Perfusion in Advanced Recurrent Melanoma of the Lower Extremity", *American Journal of Surgery, vol. 150(1),* 32–35, (Jul., 1985).

Sugahara, R.U., et al., "The Use of Hyperthermia in Cancer Treatment", *Consensus on Hyperthermia for the 1990s, Plenum Press, New York,* 79–98, (1990).

Uzunoglu, N., et al., "Four Element Computer Conrolled 432 Mhz Phased Array Hyperthermia System", *Consensus on Hyperthermia for the 1990s*, Plenum Press, New York, 311–313, (1990).

VanRhoon, G., et al., "Instrumentation for Clinical Hyperthermia", *Consensus on Hyperthermia for the 1990s, Plenum Press, New York,* 57–77, (1990).

Vertrees, R.A., "Hyperthermia: What is its role?", *Mechanisms of Perfusion X, Perfusion Resource Association, Inc.,* (May 11–14, 1995).

Vertrees, R.A., et al., "Induction of Whole Body Hyperthermia with Venovenous Perfusion", *ASAIO 41st Annual Conference Abstracts, vol. 41(1),* 62, (1995).

Vertrees, R.A., et al., "Pathology of Perfusion–Induced Whole Body Hyperthermia in Acute Swine", *Eleventh Annual Scientific Session of the Acadmey of Surgical Research,* Poster presentation, (Oct. 5–7, 1995).

Vertrees, R.A., et al., "Perfusion Hyperthermia: The Pathophysiologic Response", *Southern Medical Assn's Annual Conference, and Conjoint Meeting of the American Society of Clinical Hyperthermic Oncology,* Abstract/resentation, S143, (1995).

Yokoyama, I., et al., "Pelvic Perfusion Hyperthermia for Advanced Pelvic Malignancies", *Japanese Journal of Surgery, vol. 15(1),* 49–54, (1985).

* cited by examiner

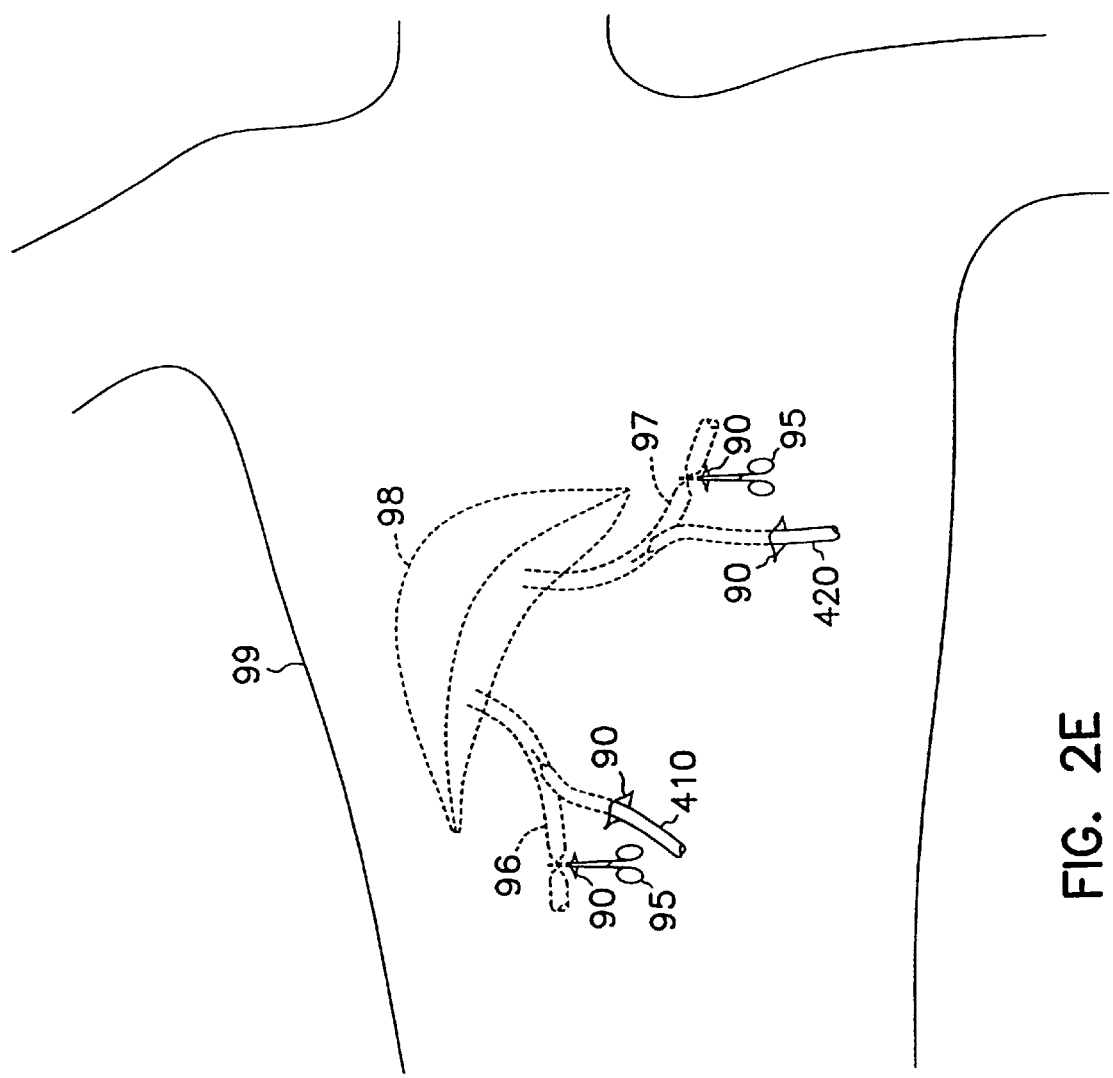

| File | Create | Edit | View | Options | Preferences | Return! |

— 606
— 608

PAGE 1 OF 8

WATER CIRCUIT CHECKLIST

638 ⌐ [ SYSTEM ON, PLUG SECURE ]

WATER CIRCUIT

612 ☐ HEAT EXCHANGER CONNECTED TO WATER
616 ☐ WATER RESERVOIR FULL

WATER CIRCUIT TEMP PROBES CONNECTED AND FUNCTIONAL

620 ☐ WATER INTO HEAT EXCHANGER
624 ☐ WATER OUT OF HEAT EXCHANGER

628 ☐ READY TO START WATER PUMP

IN CASE OF EMERGENCY [BYPASS (^B)] CHECKLIST!
— 646

640 — [LOW]
642 — [0.0]
644 — [0.0]

FIG. 6

| File | Create | Edit | View | Options | Preferences | Return! |

PERFUSION CIRCUIT CHECKLIST                    PAGE 4 OF 8

PERFUSION CIRCUIT
910 — [ ] TUBING IN PUMP IN PROPER DIRECTION.
912 — [ ] TUBING PUMP OCCLUSION SET PROPERLY
914 — [ ] BLOOD LINES CONNECTED TO HEAT EXCHANGER
916 — [ ] PERFUSION CIRCUIT SECURELY MOUNTED
918 — [ ] HEAT EXCHANGER PRESSURE LINE CONNECTED
920 — [ ] BLOOD SYSTEM PRESSURE CONNECTED

BLOOD TEMP PROBES CONNECTED AND FUNCTIONAL
922 — [ ] INTO HEAT EXCHANGER
924 — [ ] OUT OF HEAT EXCHANGER
926 — [ ] BUBBLE DETECTOR CHECKED/SECURE
928 — [ ] BLOOD LINES CONNECTED TO BUBBLE DETECTOR
930 — [ ] READY TO PRIME PERFUSION CIRCUIT

932 — [0.00]         △(^U) — 934
                     ▽(^D) — 936

940 — [0.0]
942 — [0.0]
944 — [CLEAR]

BLOOD FLOW RATE L/min

938 — [STOP (F10)] BLOOD PUMP        IN CASE OF EMERGENCY [BYPASS (^B)] CHECKLIST!
                                                                    646

FIG. 9

| File | Create | Edit | View | Options | Preferences | Return! |

PERFUSION CIRCUIT PRIMING       PAGE 6 OF 8

PRIMING PERFUSION CIRCUIT.

CURRENT    TARGET
BUBBLES DETECTED:          YES
TIME SINCE LAST BUBBLE DETECTED:  00.00   02:00
PERFUSION CIRCUIT TEMPERATURE:    0.0    39.0

Cancel (Esc)        Continue (^C)

BLOOD FLOW RATE L/min  0.00   △(^U)
                              ▽(^D)

STOP (F10)  BLOOD PUMP    IN CASE OF EMERGENCY   BYPASS (^B)  CHECKLIST!

FIG. 11

| File | Create | Edit | View | Options | Preferences | Return! |

SUBJECT PROCEDURE CHECKLIST  PAGE 7 OF 8

ANESTHESIA PROTOCOL
1210 — ☐ FLUID ADMINISTRATION LINES PRIMED
1212 — ☐ HEPARIN GIVEN, ACT CHECKED
1214 — ☐ ANESTHETIC AGENTS PER PROTOCOL

TEMPERATURE PROBES CONNECTED AND FUNCTIONAL

1216 — ☐ TYMPANIC LEFT — 1226
1218 — ☐ TYMPANIC RIGHT — 1228
1220 — ☐ ESOPHAGEAL — 1230
1222 — ☐ INDWELLING — 1232
1224 — ☐ RECTAL/BLADDER — 1234
1225 — ☐ RECTAL — 1235

1236 — ☐ MONITOR/NON-COMMITTED TEMP1
1237 — ☐ MONITOR/NON-COMMITTED TEMP2

[ 1240 | 1241 ]  L/MIN., BLOOD FLOW
                 mm Hg, SYSTEM PRESSURE

938 — STOP (F10) BLOOD PUMP    IN CASE OF EMERGENCY  BYPASS (^B) CHECKLIST!  — 646

FIG. 12

```
| File | Create | Edit | View | Options | Preferences | Return! |
```

SUBJECT CHECKLIST (CONT.)                                    PAGE 8 OF 8

1310 — ☐ BLOOD PUMP STOPPED!
1312 — ☐ BLOOD LINES CONNECTED TO SUBJECT

938 — [STOP (F10)] BLOOD PUMP     IN CASE OF EMERGENCY   [BYPASS (^B)] — 646  CHECKLIST!

FIG. 13

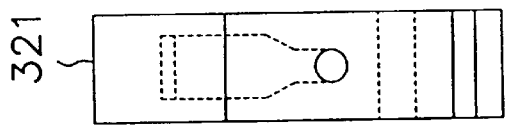
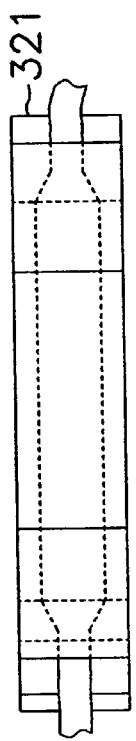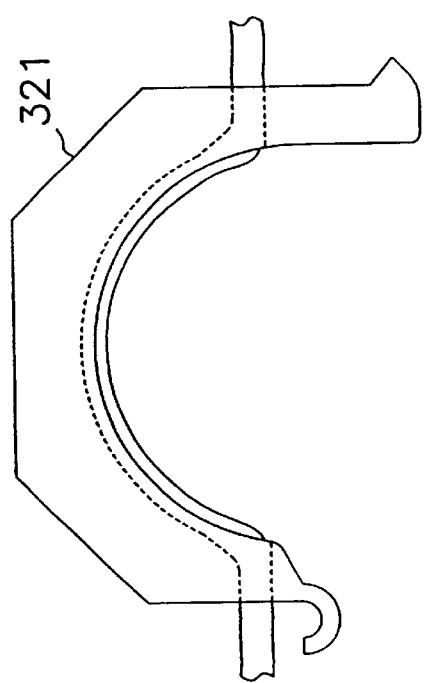
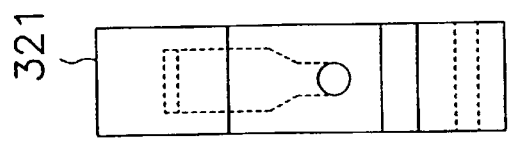

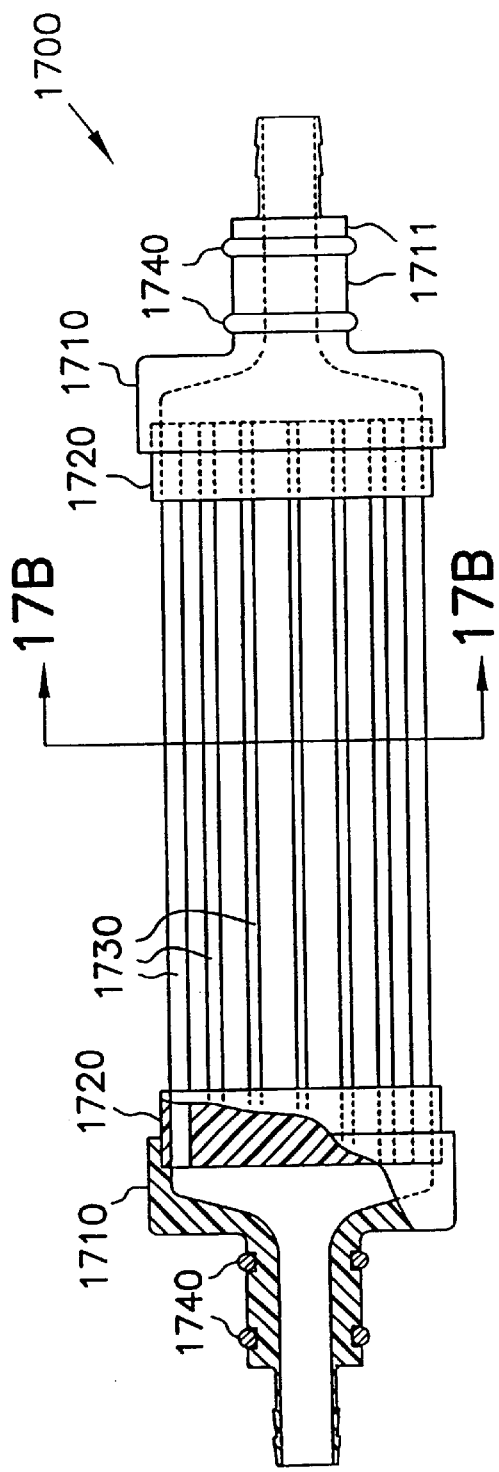
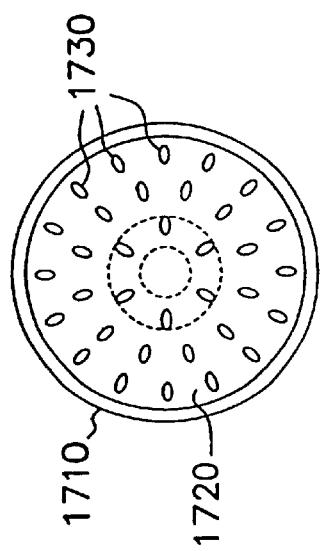
FIG. 17A
FIG. 17B ived for using a computerized system for a perfusion hyper/hypothermia treatment of a patient which obtains a body fluid having a particular temperature. A plurality of temperature signals representative of temperatures at each of a plurality of patient locations on or within the patient are coupled to the computer system. Measured temperatures are compared to a set of stored parameters in the computer system to generate a comparison value which controls a change in the temperature of the body fluid which is made by the extracorporeal fluid-treatment system. The body fluid is then perfused into the patient to either warm, cool, or maintain the current temperature of the patient. In one such embodiment, the body fluid is blood withdrawn from the patient. In another such embodiment, the body fluid is saline.
PERFUSION HYPERTHERMIA TREATMENT SYSTEM AND METHOD

CROSS REFERENCE TO RELATED APPLICATION

This application is a continuation of application Ser. No. 09/042,382, filed Mar. 13, 1998 and now abandoned, which is a division of application Ser. No. 08/516,580, filed Aug. 18, 1995 and now U.S. Pat. No. 5,730,720, which is incorporated herein by reference.

FIELD OF THE INVENTION

The present invention relates to methods and apparatus for controlling medical hyperthermia or hypothermia treatments for humans and other animals, and more specifically for automatically controlling temperatures and rates of change of temperature in the subject of a perfusion hyperthermia or hypothermia treatment using a programmed computer system.

BACKGROUND OF THE INVENTION

Fever is one mechanism by which a mammal fights disease. A number of pathogens, including some bacteria, some cancers, and some viruses, such as the HIV retrovirus and other enveloped viruses, seem to be adversely affected by heat. In addition, certain processes which normally fight disease, such as tumor necrosis factor A, seem to be stimulated with hyperthermia. Fever can be thought of as a natural-response hyperthermia treatment of a mammal to a pathogen or disease condition which may have a more adverse effect on the pathogen or diseased tissue than on the rest of the animal's body, thus allowing the body to prevail against the disease condition.

In particular, artificially-induced whole-body hyperthermia, as opposed to, for instance, local application of heat to a tumor or extracorporeal hyperthermia treatments to blood, may be required to treat such diseases as HIV infection or a metastasized cancer where the pathogen is universally distributed in the experimental subject or clinical patient, since leaving any one part of the patient cooler (i.e., outside the boundary of the hyperthermia treatment) will provide a safe harbor for the pathogen, which will again spread into the rest of the body once the hyperthermia treatment ends.

Hippocrates first described hyperthermia treatments, around 480 BC, which used hot sand baths for patients with skin tumors. In 1927, a Nobel prize was awarded to a doctor, Warner Jauregg who used malaria-induced fever to treat syphilis. However, by the mid-1930s the medical community began to recognize the potential hazards of hyperthermic therapy, and a 1934 survey by the Council on Physical Therapy of the American Medical Association documented 29 deaths resulting from hyperthermia treatments. Among the adverse effects of hyperthermia are increases in cardiac output by as much as 200% of normal, increases in oxygen consumption, changes in serum enzymes, drops in phosphate, calcium, and magnesium levels, heart, liver and brain damage and failure, disseminated intravasular coagulation, hemolysis of red blood cells, spinal-cord necrosis, fluid loss from diuresis and perspiration, electrolyte shifts, and bleeding problems associated with systemic heparinization.

Hyperthermia has been induced using hot baths, bacterial inoculation, hot wax, hot air systems, heated water blankets, etc.

Hyperthermia has been combined with radiation and/or chemotherapy to achieve synergistic results against cancers (i.e., when heat is combined with those other therapies, destruction of neoplastic tissues occurs at smaller dosages of radiation or chemotherapy agents).

One shortcoming of prior-art systems and methods has been the lack of tight, fast, and automatic control over, and lack of visual feedback with respect to, the exact temperature achieved in particular parts of the body of the patient, the average temperatures of the body core or various body parts, the rates of temperature change, and temperature gradients between various body parts. In addition, known prior-art perfusion hyperthermia systems have not automated system checklists, patient-monitoring systems, alarms, treatment-procedure recording, nor the monitor indications and controls provided to the medical professionals who administer the hyperthermia treatment.

SUMMARY OF THE INVENTION

What is needed, and what the present invention provides, is a system and method that automatically monitors and controls a perfusion hyperthermia treatment using a system including one or more programmed computers, and mechanical and sensor subsystems. The system includes a fluid path between a patient and an external fluid-treatment subsystem, wherein control of the external fluid-treatment subsystem includes feedback from sensors coupled to the patient. The resulting integrated system provides an automated monitoring and control of the patient, the external fluid-treatment subsystem, and the treatment. In one embodiment, the fluid passing between the patient and the external fluid-treatment subsystem is blood.

In one embodiment, an apparatus and method are provided for using a computerized system for a perfusion hyper/hypothermia treatment of a patient which obtains a body fluid having a particular temperature. A plurality of temperature signals representative of temperatures at each of a plurality of patient locations on or within the patient are coupled to the computer system. Measured temperatures are compared to a set of stored parameters in the computer system to generate a comparison value which controls a change in the temperature of the body fluid which is made by the extracorporeal fluid-treatment system. The body fluid is then perfused into the patient to either warm, cool, or maintain the current temperature of the patient. In one such embodiment, the body fluid is blood withdrawn from the patient. In another such embodiment, the body fluid is saline.

In one embodiment, the supply voltage to the plurality of thermistors is provided by a circuit which provides a very short pulse, one at a time and sequentially to each thermistor, in order to reduce heating of the thermistors and to reduce the electrical hazards, and via a multiplexor, couples the analog response signal to an A/D convertor.

In one embodiment, the mass of water in the water circuit is minimized in order to improve the response time of the temperature control feedback mechanism.

In one embodiment, the volume of blood in the blood circuit is minimized in order to reduce the amount of blood outside the patient and to improve the response time of the temperature control feedback mechanism.

In one embodiment, a rate of change of temperature is measured and controlled according to a stored parameter in the computer system.

In a further embodiment, checklist input is elicited and received from a user, and used to control operation of the computer system.

In another further embodiment, correct operation of the computer system is repeatedly verified with a self-test program.

In another further embodiment, correct coupling of the computer system to external components is repeatedly verified with a self-test program.

One embodiment also provides a visualization of the monitored functions.

One embodiment also provides a recording over time of one or more of a set of measured parameters.

One embodiment provides for an integrated disposable body-fluid subsystem which mates with a reusable system interface.

BRIEF DESCRIPTION OF THE DRAWINGS

In the following detailed description of the invention, reference is made to the accompanying drawings which form a part hereof, and in which is shown by way of illustration only, specific exemplary embodiments in which the invention may be practiced. It is to be understood that other embodiments may be utilized, and structural changes may be made, without departing from the scope of the present invention.

FIG. 2E illustrates an exemplary perfusion system 400 used to effect a single-organ perfusion hyperthermia or hypothermia of patient 99.

FIG. 6 illustrates an exemplary display screen usable with a mouse-type point-and-click input device for one portion of the software-controlled user-interactive start-up-procedure checklist.

FIG. 9 illustrates an exemplary display screen usable with a mouse-type point-and-click input device for a fourth portion of the checklist.

FIG. 11 illustrates an exemplary display screen usable with a mouse-type point-and-click input device for a sixth portion of the checklist.

FIG. 12 illustrates an exemplary display screen usable with a mouse-type point-and-click input device for a seventh portion of the checklist.

FIG. 13 illustrates an exemplary display screen usable with a mouse-type point-and-click input device for a eighth portion of the checklist.

FIG. 14C is a plan view of one embodiment of blood-pump interface 321.

FIG. 14D is a left elevation view of the blood-pump interface 321 shown in FIG. 14C.

FIG. 14E is a bottom elevation view of the blood-pump interface 321 shown in FIG. 14C.

FIG. 14F is a right elevation view of the blood-pump interface 321 shown in FIG. 14C.

FIG. 14G is a top elevation view of the blood-pump interface 321 shown in FIG. 14C.

FIG. 17A shows a front view of a disposable blood-tube assembly 1700 usable with modular clam-shell heat exchanger 1600 of FIG. 16A according to the present invention.

FIG. 17B shows a cross-section view of the disposable blood-tube assembly 1700 of FIG. 17A.

DETAILED DESCRIPTION OF THE PREFERRED EMBODIMENT

In the following detailed description of the preferred embodiments, reference is made to the accompanying drawings which form a part hereof, and in which are shown, by way of illustration, specific embodiments in which the invention may be practiced. It is to be understood that other embodiments may be utilized and structural changes may be made without departing from the scope of the present invention.

The success of hyperthermia or hypothermia and whole-body hyperthermia or hypothermia treatment (as measured by efficacy of disease removal and by reduced patient complications and mortality) is related to the multiple controls over the absolute temperature achieved, temporal profiles of temperature, temperature distribution within the patient, and the rates of change of temperature. Each of these parameters is to some extent affected by numerous factors, such as heat shedding by the patient, the mass of the patient, circulatory patterns or abnormalities (e.g., stroke) within the patient, and the flow through the extracorporeal circuit (ECC). In turn, each of these temperature parameters affects the patient. For instance, a rapid temperature rise may lead to heat-shock protein generation or degradation, while a slow temperature rise may induce thermal tolerance in some cancers. Natural fevers have a temperature profile which changes over time, and may vary in distribution within the body, and such specific time-varying profiles may thus be effective in combatting certain pathogens. It is therefore desirable to have automatic, pre-determined temporal and spatial temperature profiles for a treatment.

In the following discussions, specific reference is made to the extracorporeal circulation and perfusion of blood as the fluid being treated by the system and method of the present invention. Other embodiments circulate and perfuse other body fluids, which are defined in this invention to include blood or other body fluids obtained from the patient and treated and returned by perfusion, as well as other fluids obtained from commercial sources, such as sterile saline (hereinafter collectively called "body fluid(s)"), and for such embodiments, the terms used in the descriptions for treating or transporting "blood" nn(such as "blood tubing" or "blood pump") should be interpreted to treat or transport the relevant body fluid.

Figure 1:
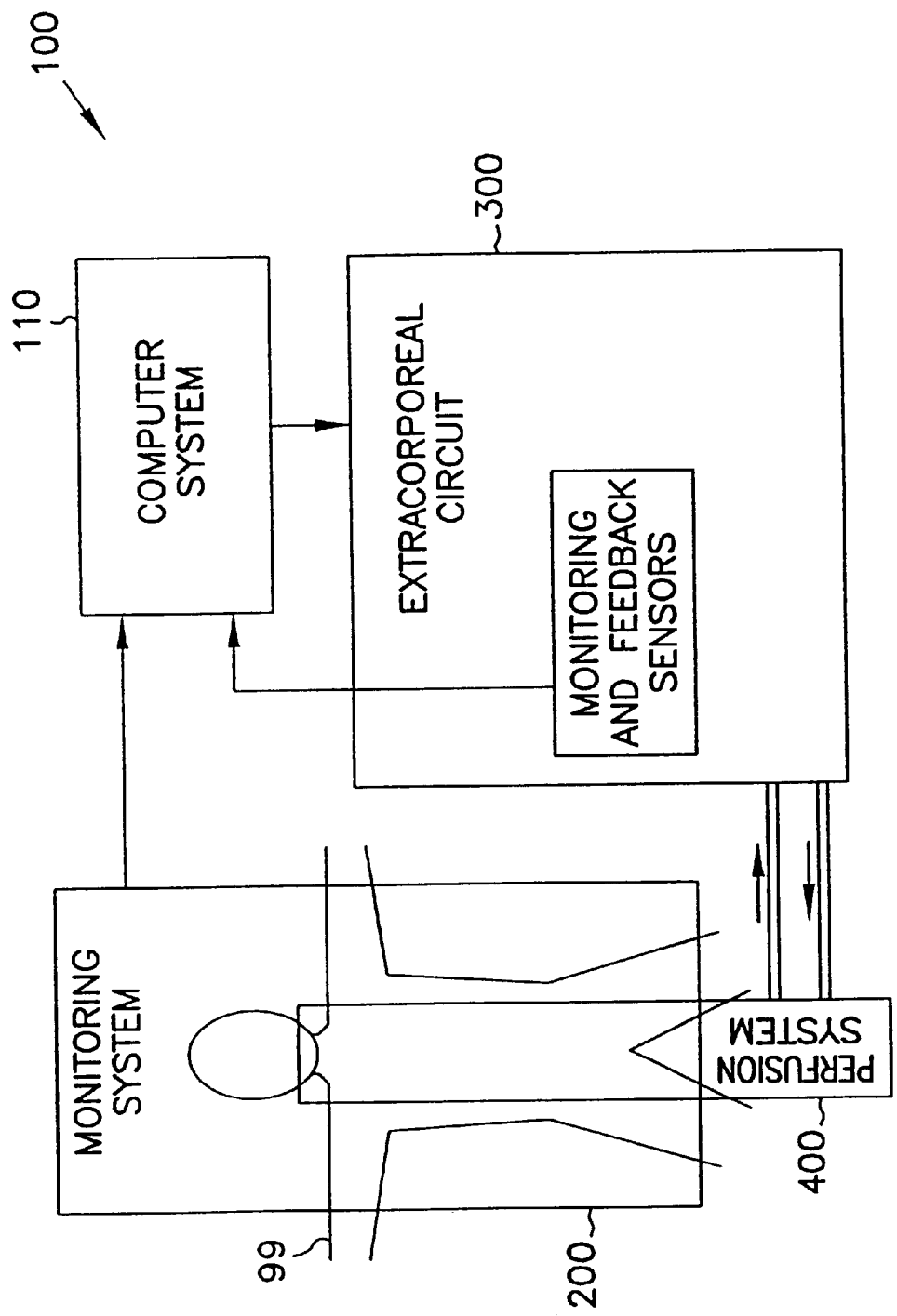
FIG. 1 shows a high-level conceptual overview of perfusion hyperthermia/hypothermia treatment system (PHTS) 100.

FIG. 1 shows a conceptual drawing of one embodiment of a perfusion hyper/hypothermia treatment system (PHTS) 100 comprising computer system 110 for monitoring and controlling the system using input from a user, monitoring system 200 for measuring various parameters of the PHTS 100 and patient 99 (or other biological organism, organ, or preparation being treated, hereinafter collectively called "patient 99") and for providing representative signals to computer system 110, perfusion system 400 for withdrawing blood from patient 99 and later returning the blood after treatment, and extracorporeal circuit (ECC) 300 for treating the withdrawn blood. PHTS 100 can be used to effect either hyperthermia or hypothermia of patient 99, depending on the treatment desired.

In one embodiment, the withdrawn blood is first circulated to observe or achieve an initial stable "normal" temperature (e.g., at a "normal" oral temperature of, for example, 98.6° F. or 37° C.) in patient 99 (i.e., in the case where the initial observed temperature is not stable or "normal," one embodiment controls the heat feedback to achieve such a state). Heat is then added to the blood by ECC 300 at a rate which achieves a predetermined rate of temperature increase as measured at one or more points measured in patient 99 (and/or other treatment performed) until a stable hyperthermia treatment state is achieved. This hyperthermia is then maintained for a period of time, then heat is removed from the blood by ECC 300 at a rate which achieves a predetermined rate of temperature decrease until the patient is returned to a "normal" temperature and stabilized. In another embodiment, the withdrawn blood is first circulated to observe (or achieve) an initial stable "normal" temperature in patient 99, then heat is removed from the blood by ECC 300 at a rate which achieves a predetermined rate of temperature decrease as measured at one or more points measured in patient 99 (and/or other treatment performed) until a stable hypothermia treatment state is achieved. This hypothermia is then maintained for a period of time, then heat is added to the blood by ECC 300 at a rate which achieves a predetermined rate of temperature increase until the patient is returned to a "normal" temperature and stabilized. Such hypothermia can be used, for example, to reduce the metabolic rate of patient 99 for certain surgical procedures, or in certain medical management instances (for example, in children or infants with pulmonary insufficiency). In yet another embodiment, heat is added to, or removed, from the blood by ECC 300 at a rate which achieves a predetermined rate of temperature increase or decrease as measured at one or more points measured in patient 99 (and/or other treatment performed) and until a stable temperature treatment state is achieved; in order, for example, to bring a hypothermia victim back to normal temperature, or to remove excess fever in a controlled fashion.

Figure 2A:
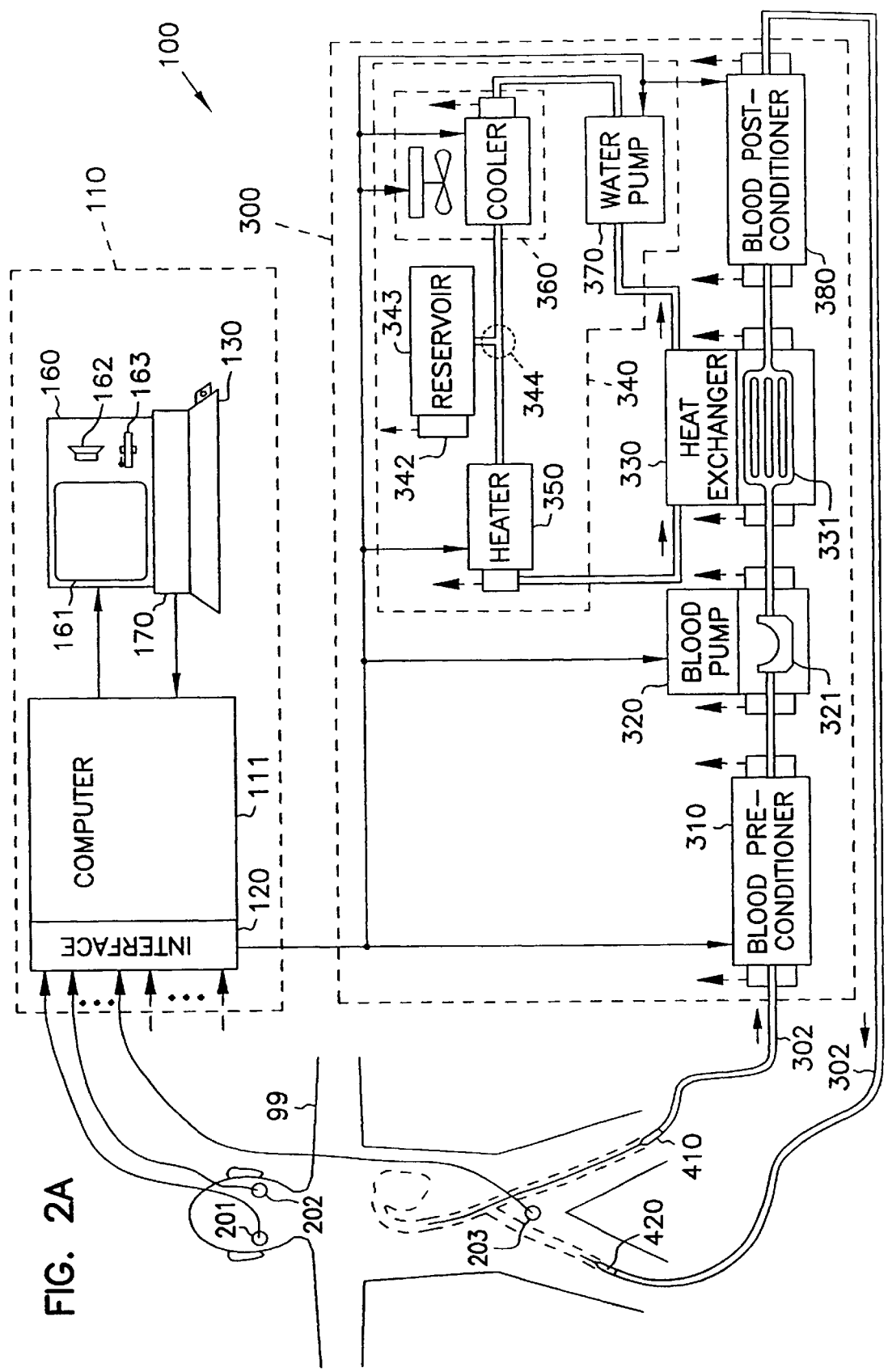
FIG. 2A shows a more detailed conceptual drawing of PHTS 100.

FIG. 2A shows a more detailed conceptual drawing of one embodiment of PHTS 100 shown in FIG. 1. Computer system 110 comprises computer 111, one or more interface 120, one or more input device 130, and one or more output device 160. In one embodiment, monitoring system 200 comprises a plurality of patient-temperature probes 201 through 203. In one embodiment, ECC 300 comprises blood tubing 302, blood pre-conditioner 310, blood pre-conditioner interface 311, blood pump 320, blood-pump interface 321, heat exchanger 330, heat-exchanger interface device 331, blood post-conditioner 380, blood postconditioner interface 381, water-conditioning subsystem 340 (comprising water reservoir 343, water reservoir level detector 342, "T" connector 344, water heater 350, water cooler 360, and water pump 370, plus associated sensors for temperature, pressure, and/or water level). In another embodiment, ECC 300 omits blood pre-conditioner 310 and blood-post-conditioner 380. Perfusion system 400 comprises canulae 410 and 420, and the pre-ECC and post-ECC components, if any, in a particular embodiment.

In one embodiment, computer system 110 comprises an IBM-compatible personal computer. In one embodiment, interface 120 is a signal-interface card or circuit board which resides within computer system 110, and provides signals to computer 110 representative of various measured system parameters, such as temperature, pressure, and flow rate. In one such embodiment, computer system 110 comprises computer 111, which comprises a dedicated computer board based on a high-performance Intel microprocessor coupled to interface circuit 120, and which communicates with personal computer 170, which in turn provides input device 130 and output device 160 functions. In one embodiment, input device 130 comprises a keyboard with an associated pointer input device, such as a track-ball or mouse, which is coupled to computer system 170. In another such embodiment, input device 130 comprises a touch-sensitive-screen input device such as is commonly known in the computer art, wherein the user touches certain portions of the display screen which elicit input from the user under program control. In yet another such embodiment, input device 130 comprises a set of touch-sensitive bezel buttons physically located next to display screen 161. In one embodiment, output device 160 comprises a display 161 having a video-graphics attachment (VGA) display screen, such as a cathode-ray-tube (CRT) or, preferably, a liquid crystal display VGA (LCD-VGA) screen. In one such embodiment, output device 160 also comprises an audio output device 162, such as an electronically-driven buzzer or speaker, used to alert the user of various exigencies or other conditions. In one such embodiment, audio-output device 162 comprises a tone generator producing different sounds for alerting a user to various warnings or alarms. In another such embodiment, recorded or synthesized voice signals are converted to sound by audio-output device 162, for alerting a user to various warnings or alarms. In one such embodiment, output device 160 also comprises a data-output device 163, such as a diskette drive, to write data from a treatment operation onto a diskette, a magnetic tape drive to write data from a treatment operation onto magnetic tape, and/or a network connection (e.g., an Ethernet local-area network) to write data from a treatment operation onto a dataset on a centralized file server.

Monitoring system 200 measures various parameters of the PHTS 100 and/or patient 99. In one embodiment, temperature probes 201 through 203 comprise solid-state thermistor devices which measure temperatures at a plurality of points on or within the subject patient 99. For instance, in one embodiment, probe 203 measures the temperature within the bladder, and probes 201 and 202 measure the tympanic temperature in the right and left ears, respectively. In another such embodiment, one or more additional or alternative temperature probes also measure rectal temperature (in one embodiment, two such probes are used to measure temperature at two different depths within the rectum), body-core temperature using deep subcutaneous placement, nasopharyngeal temperature, intracardiac and/or intrathoracic temperature using thermodilution cardiac-output placement, intrapulmonary artery and/or vein temperature, esophagus temperature, limb skin temperature, limb muscle temperature (by an embedded thermistor probe), and/or limb bone temperature (by an embedded thermistor probe). In other embodiments, one or more additional or alternative temperature probes also measure temperature at the canulation site(s).

In one embodiment, the one or more temperature probes 201–203 are thermistors calibrated to a suitable accuracy within the anticipated temperature ranges of the treatment. In one such embodiment, care is taken to minimize the thermal mass and the thermal conductivity path from embedded thermisters (e.g., in muscle or bone) to the external environment, in order that the thermistor accurately measures core temperatures without significant thermal leakage to the external environment. For instance, a "trocar" (a hollow needle used to implant a thermistor into a bone marrow site) left in place after implanting a thermistor can provide a significant thermal path from the thermistor site to the external air, leading to errors in temperature measurement, and therefore the trocar is partially or completely withdrawn after placing the thermistor in order to thermally isolate the thermistor. In another embodiment, monitoring system 200 also includes patient heart-signal ("ECG") probes, brain-signal ("EEG") probes, and blood-pressure probes to provide additional signals to be used for monitoring and display to computer 110.

Figure 2B:
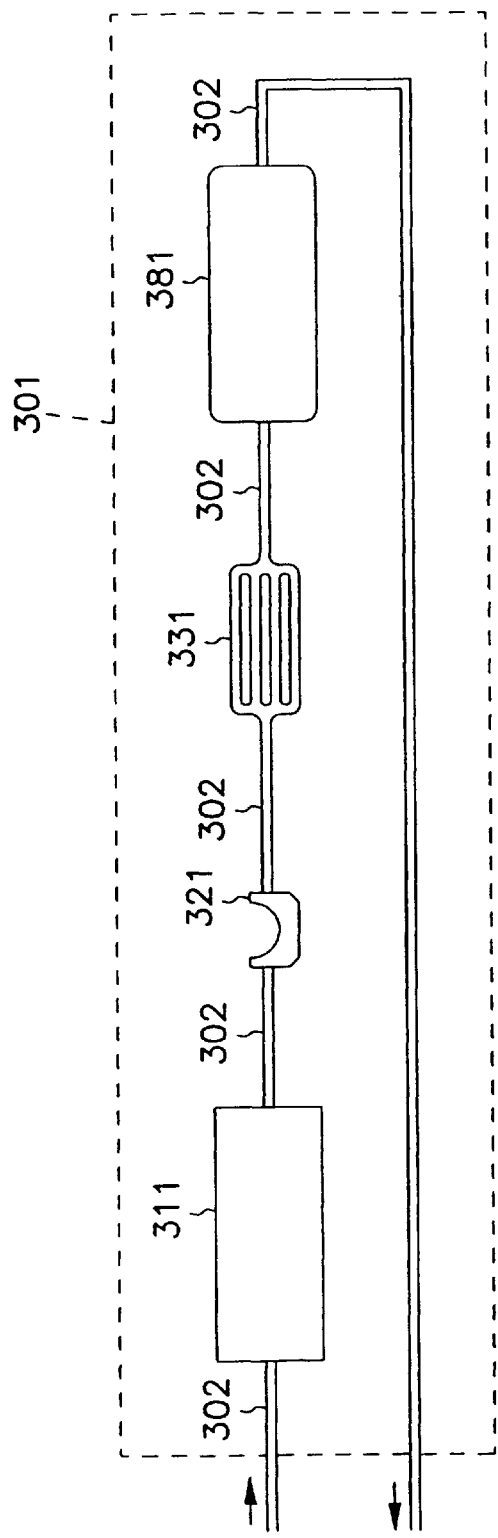
FIG. 2B illustrates a schematic of disposable subsystem 301.

FIG. 2B illustrates a schematic of disposable subsystem 301. In one embodiment, disposable subsystem 301 is manufactured as a single integrated subsystem with all necessary tubing connected and sealed, pretested for functionality and absence of leaks, sterilized, and packaged in a sterilized delivery package. This disposable subsystem 301 provides an easy-to-use, sterile, reliable part which isolates all parts which come into contact with the patient's fluids (e.g., blood), and can be quickly replaced for each new patient with a minimum of manual intervention or adjustments. In the embodiment shown in FIG. 2B, a length of blood tubing 302 for receiving patient blood is coupled to blood-preconditioner interface unit 311, a further length of blood tubing 302 then couples the blood to blood-pump interface 321, a further length of blood tubing 302 then couples the blood to heat-exchanger interface 321, a further length of blood tubing 302 then couples the blood to blood-postconditioner interface 321, a further length of blood tubing 302 is then coupled for returning the blood to the patient. In one embodiment, disposable subsystem 301 includes disposable sensors, such as thermisters connected before and after the heat-exchanger interface 331 and pressure sensors connected before and after blood-pump interface 321. In one embodiment, the heat exchanger is assembled such that the flow of heat exchange fluid (e.g., water) is counter to the flow of patient fluid (e.g., blood), in order that the efficiency and amount of heat transfer is maximized (i.e., the end of heat exchanger 330 having the warmest water is transferring heat energy to the coolest blood, and the end with the coolest water is transferring to the warmest blood). Blood-preconditioner interface unit 311 comprises those parts of blood preconditioner 310 which come into contact with the patient's blood, including any sensors which come into contact with the blood. In one embodiment, blood preconditioner 310 and blood-preconditioner interface unit 311 are used to add fluids, such as saline and/or various drugs, to the blood passing through disposable subsystem 301. Blood-postconditioner interface unit 381 comprises those parts of blood postconditioner 380 which come into contact with the patient's blood, including any sensors which come into contact with the blood. In one embodiment, blood postconditioner 380 and blood-postconditioner interface unit 381 are used to add oxygen and/or remove carbon dioxide from the blood passing through disposable subsystem 301. In one embodiment, disposable subsystem 301, which is otherwise as shown in FIG. 2B, omits blood-preconditioner interface unit 311 and blood-postconditioner interface unit 381.

Figure 2C:
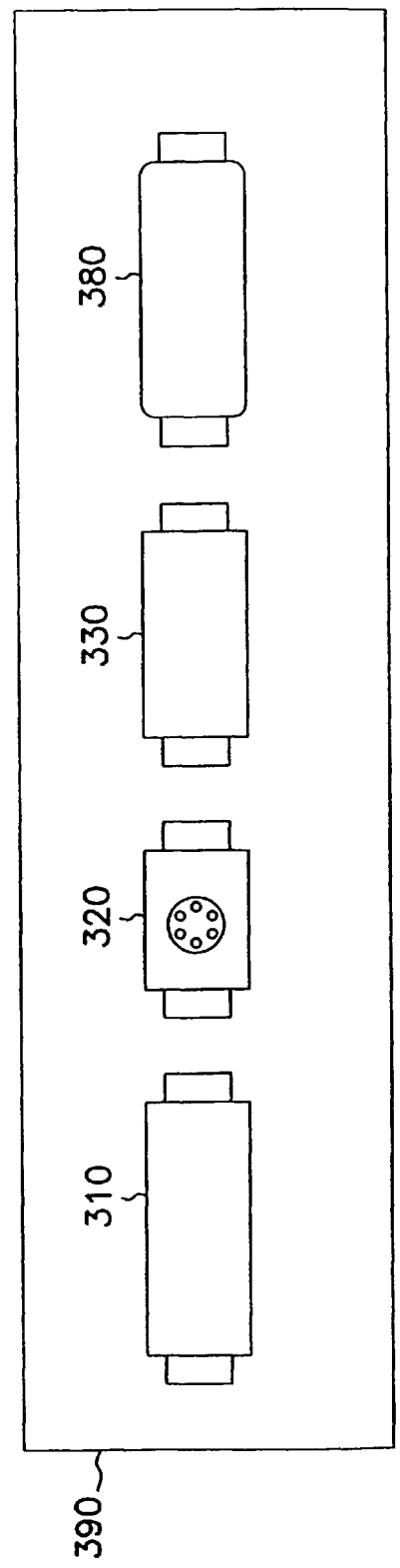
FIG. 2C illustrates a schematic of a system interface 390 which mates to disposable subsystem 301 of FIG. 2B.

FIG. 2C illustrates a schematic of a system interface 390 to disposable subsystem 301 of FIG. 2B. In one embodiment, system interface 390 is configured so that disposable subsystem 301 is easily assembled into system interface 390 to form ECC 300 by use of snap-in-place connectors, and plug-and-socket interfaces for both the mechanical and electrical subsystems thereof. In one such embodiment, disposable subsystem 301 is made so that correct assembly is easily performed and incorrect assembly is thereby prevented, as illustrated by the corresponding interfaces between disposable subsystem 301 and system interface 390 in FIGS. 2B and 2C. In one embodiment, system interface 390 comprises blood pre-conditioner 310, blood pump 320, heat exchanger 330, and blood post-conditioner 380. In another embodiment, system interface 390, which is otherwise as shown in FIG. 2C, omits blood preconditioner 310 and blood postconditioner 380. In one such embodiment, these components comprise only the permanent, reusable positions, and electrical and mechanical connectors of the respective devices, and do not come into contact with the patient's blood.

In one embodiment, disposable subsystem 301 and system interface 390 are assembled together at the start of a perfusion hyper/hypothermia treatment (PHT) by a user such as a physician or perfusion technician. In one such embodiment, a sterile disposable subsystem 301 is delivered in a preassembled state, and need only be removed from its packaging and attached to system interface 390. In one such embodiment, disposable subsystem 301 is shipped empty of any fluid, and is "primed," in one case, by the user filling it with a standard sterile saline solution. In another such embodiment, disposable subsystem 301 is shipped pre-filled with a standard sterile saline solution. Once disposable subsystem 301 is connected to system interface 390 and has been filled with a priming fluid, the ECC 300 can be checked for functionality, which, in one embodiment, is done as part of a automated system-checklist procedure, as is described more fully below. In one such embodiment, this functionality check includes pumping sterile saline solution from a supply bag through the blood circuit of ECC 300 to check the functionality (e.g., that the fluid is pumped and is heated and cooled and otherwise treated, when the appropriate commands are sent be computer system 110), and then into an output bag for later disposal.

Figure 2D:
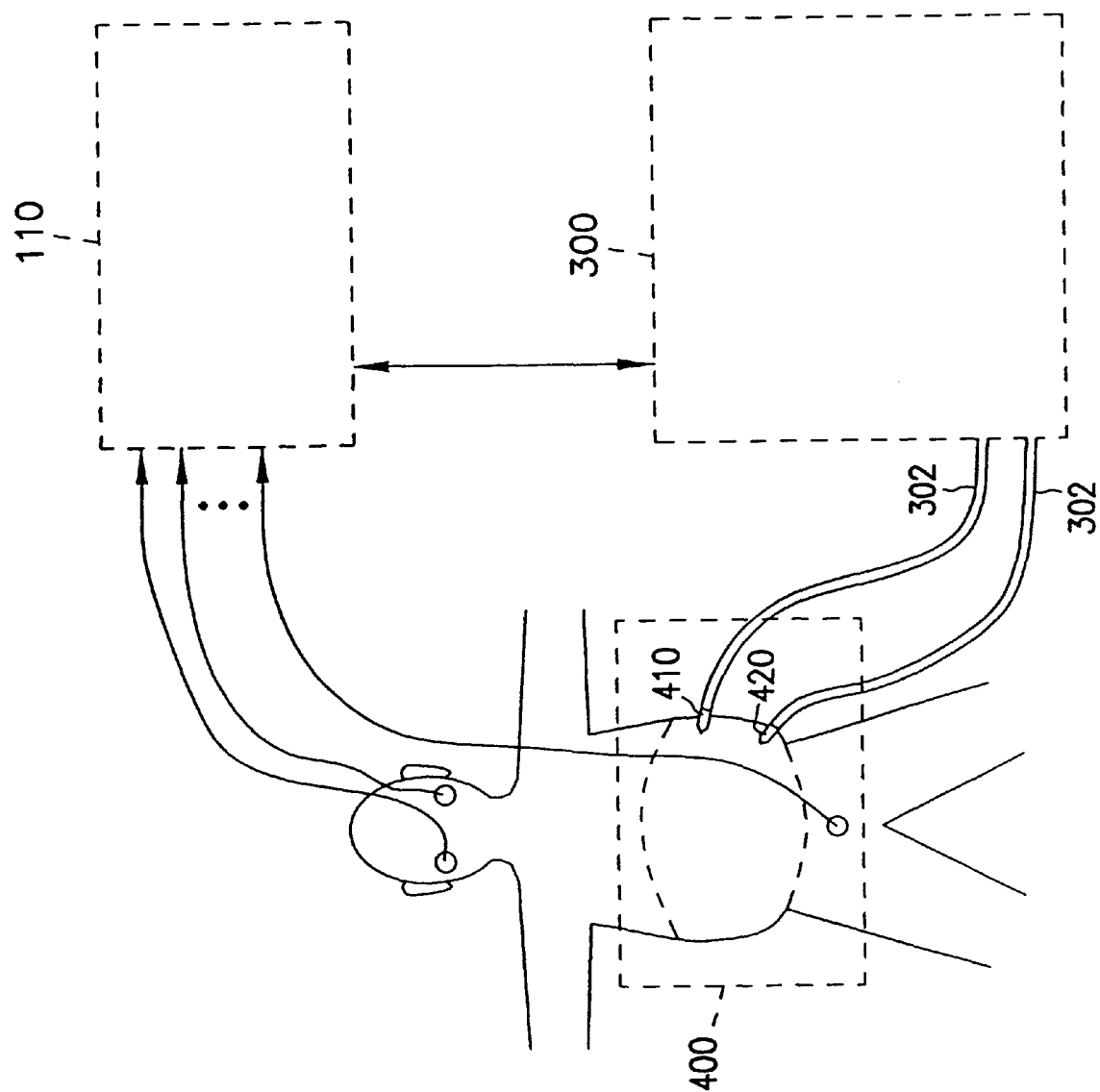
FIG. 2D illustrates an exemplary perfusion system 400 used to effect intraperitoneal hyperthermia or hypothermia of patient 99.

FIG. 2D illustrates an exemplary perfusion system 400 used to effect intraperitoneal hyperthermia or hypothermia of patient 99; this perfusion system 400 is connected to a computer system 110 and ECC 300 which are substantially the same as shown in FIG. 2A. In one such embodiment, perfusion system 400 comprises canulas 410 and 420 used to effect intraperitoneal hyperthermia of patient 99. In such an embodiment, fluid (such as sterile saline) is provided into and treated by ECC 300, then pumped into canula 420 which is inserted into one point in the peritoneal cavity of patient 99; this fluid is then withdrawn through canula 410 (which was inserted into another point in the peritoneal cavity of patient 99). It is to be understood that in such an embodiment the description of other parts of PHTS 100 apply, substituting the word "fluid" for the word "blood," when the context of the ECC 300 treatment is of other than blood. In another such embodiment, the cerebrospinal fluid cavity is treated. Thus, circulation of treated (e.g., by heparinization, electrolyte adjustment, chemotherapy, oxygenization, heating, cooling, filtering, light, irradiation, radioactivity, etc., by ECC 300) fluid into and from the peritoneal abdominal cavity or other body cavity of patient 99 (i.e., not within the circulatory system), as well as circulation through the blood system of patient 99, is specifically contemplated within the scope of the present invention. In one such embodiment, drugs (e.g., cancer chemotherapy drugs) are added to the fluid or blood (e.g., to effect a combined heat/drug treatment wherein the synergistic effect of the heat and drug therapies is desired to treat, for example, a stomach cancer which may have spread to the peritoneal cavity).

In another embodiment, individual organs (or portions of the body) are treated "in situ" in the body of patient 99. In one such embodiment, the organ to be treated is isolated from the circulatory system of patient 99 (via, e.g., laparoscopic and/or endoscopic surgical techniques via the peritoneal cavity), and perfused from and to PHTS 100 to treat isolated diseases (e.g., hepatic carcinoma). FIG. 2E schematically illustrates an exemplary perfusion system 400 used to effect such a single-organ perfusion hyperthermia of patient 99. In one such embodiment, one or more clamps 95 (such as intra-abdominal vascular tourniquets) are placed on both an artery 97 (such as the hepatic artery) and a vein 96 (such as the portal vein) for an organ 98 (such as the liver) of patient 99, and canulae 410 and 420 are used to withdraw blood for treatment by ECC 300 and to perfuse the treated blood back into the organ 98, substantially as schematically shown. One or more laparoscopic incisions 90 and/or endoscopic openings (such as the throat or rectum) are used in one embodiment to facilitate access for such a treatment. Monitoring system 200 is used to monitor the organ 98 and/or the rest of patient 99 as shown in FIG. 2A, and computer system 110 is used to control the treatment as described above for FIG. 2A.

In yet another embodiment, an isolated (i.e., removed from the body of a donor patient) organ (such as liver, kidney, pancreas or heart) is individually perfused and/or pretreated by PHTS 100 prior to implantation into a new patient 99. In one such embodiment, PHTS 100 is used, not to perform hyperthermia treatment, but to maintain the removed organ in a state which maximizes viability of the organ for later implantation; and in one such embodiment, PHTS 100 is used to effect hypothermia and/or oxygenation of the isolated organ.

Figure 2F:
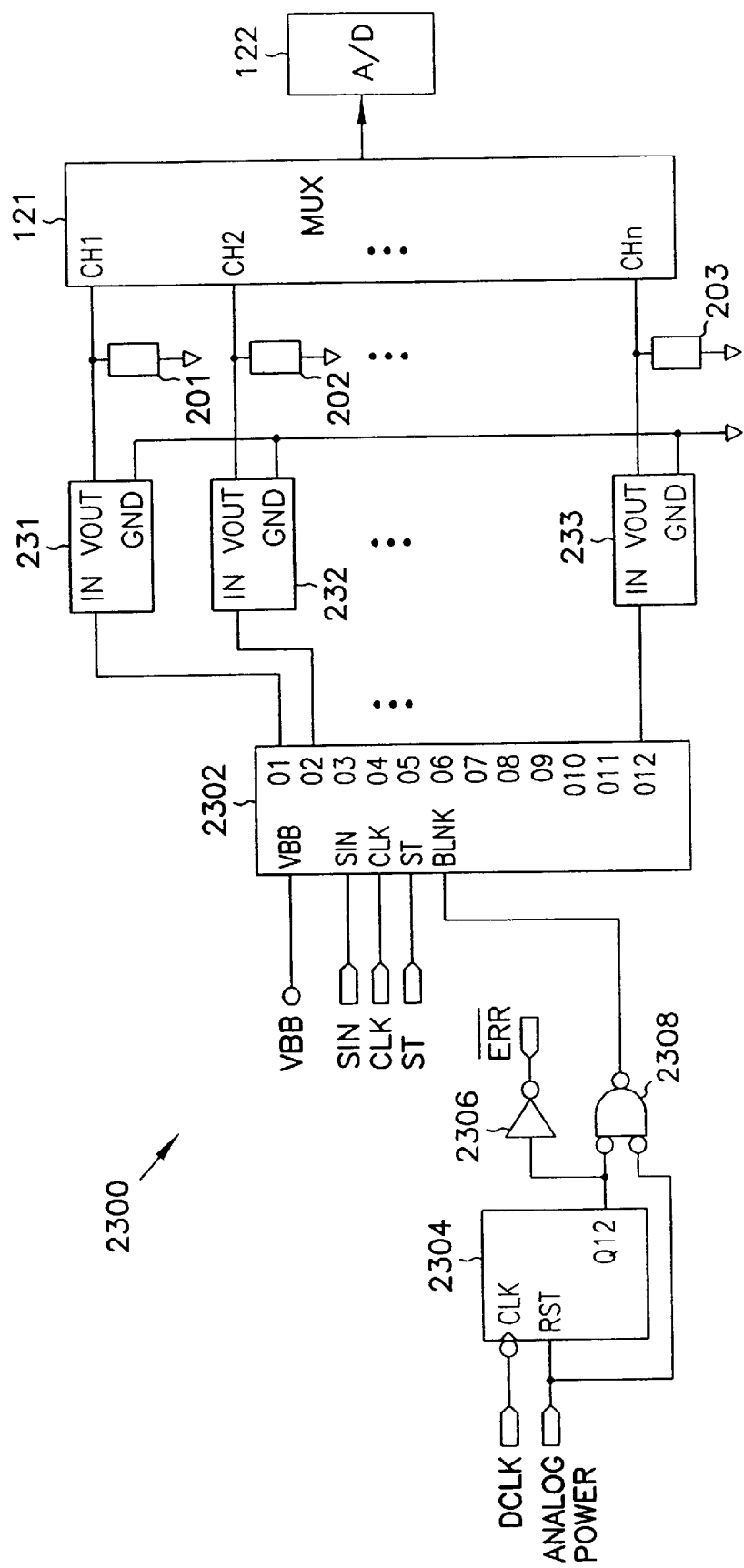
FIG. 2F shows a schematic of a circuit used to supply regulated voltage current to thermisters in the sensor probes in one embodiment of PHTS 100.

FIG. 2F shows a schematic of the thermistor electrical supply circuit 2300 used in one embodiment of PHTS 100 to supply regulated voltage pulses to thermisters in the temperature sensor probes 201–203. In order to reduce self-heating of the thermisters which would reduce the accuracy of the temperature measurements, and to reduce the electrical hazard of possible leakage currents from thermisters which are threaded into a blood vessel or otherwise implanted or in contact with patient 99, one embodiment uses short-duty-cycle pulses to drive thermisters 201–203 as shown in exemplary circuit 2300. One embodiment uses a CMOS ripple counter 2304, such as CMOS part number 74HC4020, to divide a DCLK signal which has a cycle time of approximately 139 nanoseconds to generate a Q12 signal with a cycle time of approximately 573 microseconds. The Q12 signal is inverted by inverter 2306, such as CMOS part number 74HC04, to generate the active-low signal ERR, which indicates to computer system 110 that the thermistor pulse is too long (an error condition which generates a safety alert). The falling edge of the ANALOG POWER signal (generated under software control by computer system 110) allows counter 2304 to start, and Q12 will remain low approximately 573 microseconds afterwards. Gate 2308, such as CMOS part number 74HCT32, will generate an active-low signal BLNK starting on the falling edge of the ANALOG POWER signal, and ending on the next rising edge of the ANALOG POWER signal or the rising edge of Q12, whichever is first (thus Q12 stops the BLNK signal if the ANALOG POWER signal remains active too long). High-current driver 2302, such as Fujitsu part number UCN5811A, provides a current pulse, sequentially, one at a time, to a plurality of precision voltage regulators 231 through 233 (a separate precision voltage regulator for each thermistor used in temperature probes 201–203). By limiting the RMS current, for example to a ½ millisecond or shorter pulse once per second or longer, the risk of serious injury or death to patient 99 can be reduced. The current pulse is sent as long as the BLNK signal is active to a selected one of the plurality of precision voltage regulators 231 through 233, such as National Semiconductors Corp. part number LH0070. The CLK input signal to driver 2302 is provided by computer system 110 to select the next sequential one of the plurality of precision voltage regulators 231 through 233 for the next pulse. (In one embodiment, a specified plurality of CLK pulses are sent to select a particular one of the precision voltage regulators in order to measure a particular temperature probe, e.g., 201, 202, or 203.) For example, a pulse generated on output O1 of driver 2302 is coupled to precision voltage regulator 231 which generates a precision voltage reference for a thermistor used in temperature probe 201, such as thermistor model number 100-44033-1.5-RPS-NA/NA-12-ST made by Yellow Springs Instruments, Inc., of Yellow Springs, Ohio, phone number 1(800)765-4974. The resultant signal is coupled by mux 121, such as part number CD4051, to A/D converter 122, such as Crystal part number CS5031 for conversion to a digital signal which is then coupled to computer system 110.

Figure 3:
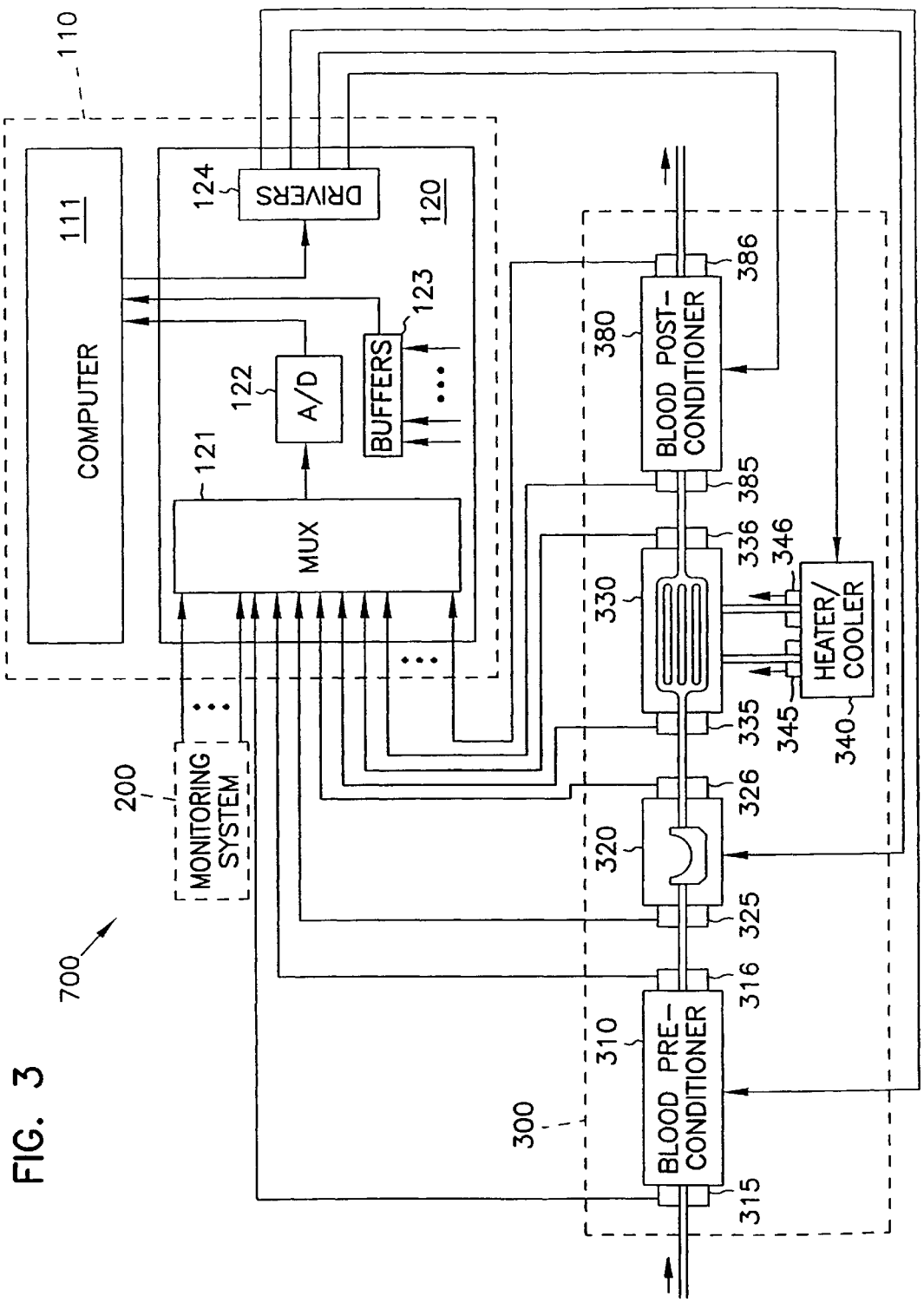
FIG. 3 illustrates one embodiment of the monitoring and control connections between monitoring system 200, extracorporeal circuit (ECC) 300 and computer system 110.

FIG. 3 shows a schematic of a portion of electrical subsystem 700 including sensor and control connections and configuration for one embodiment of ECC 300, monitoring system 200 and computer system 110. In one embodiment, monitoring system 200 provides additional sensor probes for measuring various parameters of patient 99, which provide monitoring and control in addition to the probes of ECC 300 as shown in FIG. 3. In one embodiment, each analog signal (each representing a separate physical parameter which is being measured such as pressure, flow rate, or temperature) is fed into one or more multiplexor ("mux") 121, such as a CMOS CD4051 part, within interface circuit 120. The mux 121 sequentially couples one analog signal at a time to an analog-to-digital converter ("A/D") 122, such as a Crystal CS5031 part, also within interface circuit 120. The A/D 122 converts each analog signal into a digital value representative of the value of the physical parameter being measured, and couples this digital value to computer 111. Thus, analog signals are converted to digital values for processing by digital computer 111 in a manner known in the art. Parameters which are measured directly by digital signals, such as the on-or-off states of circuits or the pulses which indicate the speed of a motor, are buffered in buffer 123 on interface circuit 120 (and in the case of motor pulses, accumulated into a pulse total over a short period of time) and coupled as digital values to computer 111 in a known manner. Once the measured parameters are processed by software 500 running in computer 111, control signals are sent by computer 111 to appropriate and known driver circuits 124 on interface circuit 120, which drive control signals back, for example, to turn on-or-off blood pre-conditioner 310, control the speed of blood pump 320, control the heat gain-or-loss of heat exchanger 330, control the amount of oxygenation provided from blood post-conditioner 380, and/or control the heat gain-or-loss of water-conditioning subsystem 340.

The sensor probes of ECC 300 include probes 315 and 316 at the blood input and output points, respectively, to blood preconditioner 310, probes 325 and 326 at the blood input and output points, respectively, to blood pump 320, probes 335 and 336 at the blood input and output points, respectively, to heat exchanger 330, probes 345 and 346 at the water input and output points, respectively, to water-conditioning subsystem 340, and probes 385 and 386 at the blood input and output points, respectively, to blood post-conditioner 380. The sensor probes of ECC 300 include, for example, devices for measuring the pressure in the blood circuit, the speed of and/or blood-flow rate through blood pump 320, the temperature gain of blood through heat exchanger 330, the fluid level of water reservoir 343, the temperature of the water exiting water heater 350, the speed of water pump 370, and whether there are bubbles in the blood circuit.

In one such embodiment, a first sensor measures a parameter of the blood at the ingress to a treating device, a second sensor measures that parameter of the blood at the egress from the treating device, and the two signals provide input to computer system 110 which is controlling the treatment device, in order to provide a closed-loop control system to tightly control the parameter of interest. For example, in one embodiment, probe 335 includes a first sensor measuring blood temperature at the blood input of heat exchanger 330, and probe 336 includes a second sensor measuring blood temperature at the blood output of heat exchanger 330; together, probes 335 and 336 provide computer system 110 with the output temperature and the temperature change across heat exchanger 330, which in turn regulates water heater 350 or water cooler 360 to adjust the amount of heat flowing into or out of the blood, respectively, and additionally monitors whether heat exchanger 330 or any associated part thereof has failed. In one embodiment, a zero-crossing detector and switch, such as a TRIAC, is used to switch heater 350 on and off at the zero-crossing point of the 50/60 Hz power supply current in order to minimize electrical spectrum noise which would otherwise result if the heater were switched on or off at a time other than at the zero crossing of a power cycle (in one embodiment, the TRIAC is turned on at substantially the "zero voltage cross" time and is turned off at substantially the "zero-current-cross" time). In one embodiment, a control interval of ⅙ second (i.e., ten AC cycles) is used for the software which controls the proportion of "ON" versus "OFF" cycles of the current sent to heater 350. According to the present invention, the software 500 running in computer 111 uses a number of temperature parameters, including absolute temperatures in various locations in the patient's body, temperature differentials between those various locations, rates of change of temperatures at those various locations, and/or the temperature rise or fall across the heat exchanger to control the heat added to or removed from the blood. In addition, various other parameters (such as oxygen consumption, $CO_2$ levels in the blood or exhaled breath, or other factors) can be analyzed by computer 111 in order to control the heat or other treatment of the blood passing through ECC 300.

In another similar example, probe 385 includes a first sensor measuring blood oxygen at the blood input of blood post-conditioner 380 in an embodiment which includes a blood oxygenator, and probe 386 includes a second sensor measuring blood oxygen at the blood output of blood post-conditioner 380; probes 385 and 386 provide computer system 110 with the output oxygen content of the blood and the oxygen-content change across blood post-conditioner 380, which in turn regulates blood post-conditioner 380 to adjust the amount of oxygen flowing into the blood, and additionally monitors whether blood post-conditioner 380 or any associated part thereof has failed. In other embodiments, the parameters measured and controlled by probes 385 and 386 and post-conditioner 380 include carbon dioxide, pH, and/or electrolytes.

In one embodiment, probe 386 includes a bubble detector 333, such as an ultrasonic transducer, which continually monitors the blood path at a point near the egress from ECC 300, at a point just before the blood is returned to patient 99, to detect any bubbles which may have entered the blood at any point before or within ECC 300. In one such embodiment, a bubble will cause a change in the echo signal of the ultrasonic transducer, thus indicating the presence of the bubble. In one such embodiment, blood post-conditioner 380 includes a bubble trap which removes any bubbles which may have entered the blood. In another such embodiment, heat exchanger 330 includes a bubble trap which removes any bubbles which may have entered the blood. In one such embodiment, such a bubble trap comprises a substantially vertical tube and/or chamber having a closed or closable end, and another end connected at substantially right angles to a substantially horizontal portion of the blood path such that as the blood passes through the horizontal path, any bubbles will rise into the vertical tube and thus be removed from the blood being returned to patient 99.

ECC 300 comprises blood tubing 302, optional blood pre-conditioner 310, blood pump 320, disposable blood-pump interface 321, heat exchanger 330, disposable heat-exchanger interface 331, optional blood post-conditioner 380, and water-conditioning subsystem 340. Water-conditioning subsystem 340 comprises a water circuit including water reservoir 343 (connected via T-connector 344), water heater 350, water cooler 360, and water pump 370. In one embodiment, water reservoir 343 is designed to minimize the amount of water (and thus the thermal mass) within the heating and cooling circuit, and thus attaches to water reservoir 343 via T-connector 344 in order to keep the thermal mass of the water in water reservoir 343 out of the heating and cooling circuit loop. In one embodiment, water reservoir 343 comprises a water-high and water-low level sensor 342 of suitable conventional design which detects whether any fluid is added (for instance, due to a leak from the blood circuit into the water circuit) or removed (for instance, due to a leak of water out of the water circuit) from the water circuit. In one embodiment, water pump 370 is located within water-conditioning circuit 340 so that it pumps water out of heat exchanger 330, through water pump 370, and then through the rest of water-conditioning system 340, in order that the water pressure in heat exchanger 330 is lowered (relative to other systems in which the outlet of the pump is connected to the inlet of the heat exchanger, thus increasing water pressure in the heat exchanger). By having lower water pressure than blood pressure within the heat exchanger 330, safety is increased (in the possible event of a leak) since blood will leak into the water, rather than the water leaking into the blood and contaminating the blood. In one such embodiment, the water circuit includes at least one clear section in order that any leak of blood into the water can be observed by the user of the system. In another such embodiment, a photodetector is included to automatically detect such discoloration and generate a signal for computer system 110 to report such a leak of blood into the water circuit.

One preferred embodiment uses water as a heat-exchange medium in a water-conditioning subsystem 340. Another preferred embodiment instead uses air as the heat-exchange medium within conditioning system 340, with corresponding heat addition or removal operations and failure detection being performed, as with the water of a water-conditioning subsystem 340. It is to be understood that other heat-exchange media are preferable in other embodiments, and that while the description below is limited to a discussion of water as the heat-exchange medium, the invention is not limited to only water as a heat exchange medium.

In one preferred embodiment, disposable circuit 301 comprises all parts of ECC 300 which come into contact with the patient's blood, is disposable and is designed to be highly reliable, easily sterilized, easily assembled to the rest of ECC 300, to hold a relatively low volume of blood, and to be relatively low-cost. In one embodiment, the volume of blood in the blood circuit is minimized in order to minimize the amount of blood outside the patient. In one such embodiment, such minimization is provided by keeping the components in disposable circuit 301 as close together as practical, and arranging the orientation of the components to minimize the length of connecting tubing. In one embodiment, the parts of disposable circuit 301 are made of clear, bio-compatible plastic which facilitates observation of the blood traveling through PHTS 100, and allows visual detection of faults. In the preferred operation, disposable circuit 301 is filled with sterile saline as part of the start-up process, and this saline is pumped through the operating ECC 300 to verify that all components of ECC 300 are functional, all immediately before the patient is attached to perfusion hyperthermia treatment system 100.

In one embodiment, perfusion system 400 comprises canulas 410 and 420 in order to effect extracorporeal circulation and treatment of the blood of patient 99. In one such embodiment, as shown in FIG. 2A, canula 410 is threaded into a femoral vein to a point relatively near the heart, and withdraws blood for conditioning and treatment (e.g., by heparinization, electrolyte adjustment, chemotherapy, oxygenization, heating, cooling, filtering, light, irradiation, and/or radioactivity, etc.) by ECC 300. The withdrawn blood is then returned to patient 99 through canula 420 into another femoral vein at a point relatively distal to the heart. The returned blood is then circulated throughout patient 99 by the patient's native circulatory system and heart. This warms the body tissues, and, in the end, will warm the lymphatic fluid (which is not connected to the cardiovascular system, but runs in parallel), and other non-circulating fluids. The cerebrospinal fluid, otherwise known as central nervous system (CNS) fluid (the fluid that is in and around the brain and spinal column, particularly massed within the cerebral ventricles) also will be warmed. The control parameters are stored in computer system 110 and are used to target a specific and selectable blood temperature which targets a selectable body temperature. The end point may be the body temperature of 43.5° C., for example, which then warms the cerebral spinal fluid, and of course, the brain. In one embodiment, fail-safe procedures and mechanisms in software 500 provide and maintain a given, selectable temperature differential (typically less than 4° C., but in some cases as much as 8° C.) between the water temperature and the blood temperature in heat exchanger 330; and a maximum temperature differential (which may be preset at 8° C., for example, but which is also user-selectable/changeable) between the blood temperature and the body temperature. Tympanic temperatures are monitored to control an absolute temperature no greater than that of the body-core temperature, and also to control the differential between the left tympanic or right tympanic, to make sure that those temperatures differ by less than 1.3° C.

One purpose for returning the treated blood at a location distant from the heart is to allow any heat added to fully mix with other venal blood and to partially dissipate into the body core of patient 99 before the warmed blood reaches the heart. This particular preferred veno-venous perfusion arrangement is for illustrative purposes, and other arrangements for withdrawing blood from either arteries or veins, and returning blood to either arteries or veins are contemplated within the scope of the present invention.

Figure 4:
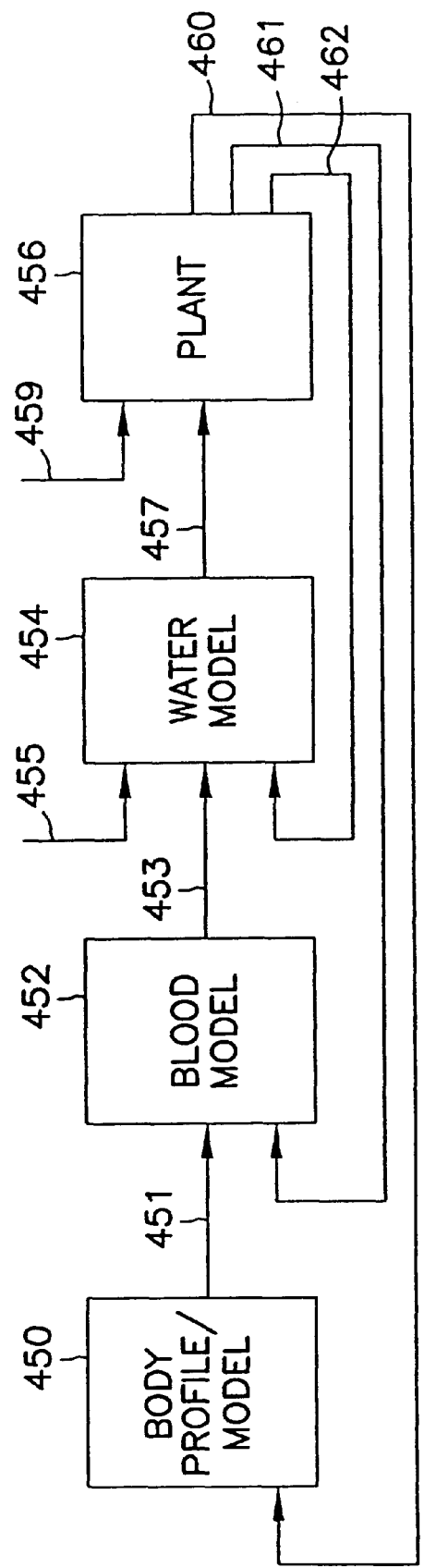
FIG. 4 illustrates one embodiment of the control flow between some of the various software modules which monitor and control PHTS 100.

FIG. 4 shows a conceptual flow of monitoring and control between some of the software modules within one embodiment of software 500. The software body profile/model 450 models how a particular patient will react to treatment (e.g., taking into account the patient's body weight, surface area, circulatory characteristics, heart rate, cardiac output, and other medical characteristics to provide a profile of how the patient's temperature will change as a result of a particular volume of blood at a particular temperature being perfused into the patient), and the desired rates of temperature change, absolute-temperature targets, heart-rate limits, blood-pressure limits, and/or cardiac-output limits. Body parameters 451 from body profile/model 450 then provide a command input to the blood model 452 to help control how heat will be added or removed from the blood within the heat exchanger 330; blood model 452 uses parameters such as the known thermal coefficient of blood, the measured cardiac blood-flow rate, any blood-volume expansion, the known volume of blood in the ECC 300, and/or the measured flow rate of blood through the ECC 300. Blood parameters 453 from blood model 452 then provide command input, along with environment parameters 455 from the external environment (such as the ambient air temperature, if fan cooling of the water circuit is used), to the water model 454 to help control how heat will be added to or removed from the water within the water-conditioning subsystem 340. Other parameters used by the water model 454 include the volume of water in the water circuit (i.e., its thermal mass), the known maximum power capacity of heater 350, and/or the known fan speed of cooler 360. Water parameters 457 from water model 454 then provide command input to the plant model 456 of how heat will be added to or removed from the blood, overall, by ECC 300. Plant model 456 in turn measures temperatures throughout PHTS 100 and provides feedback parameters 460 (for example, indicating the various body temperatures), 461 (for example, indicating the blood temperatures and their rise or fall), and 462 (for example, indicating the water temperature and its rise or fall through the heat exchanger 330) into each of the other models, as shown in FIG. 4.

Figure 5A:
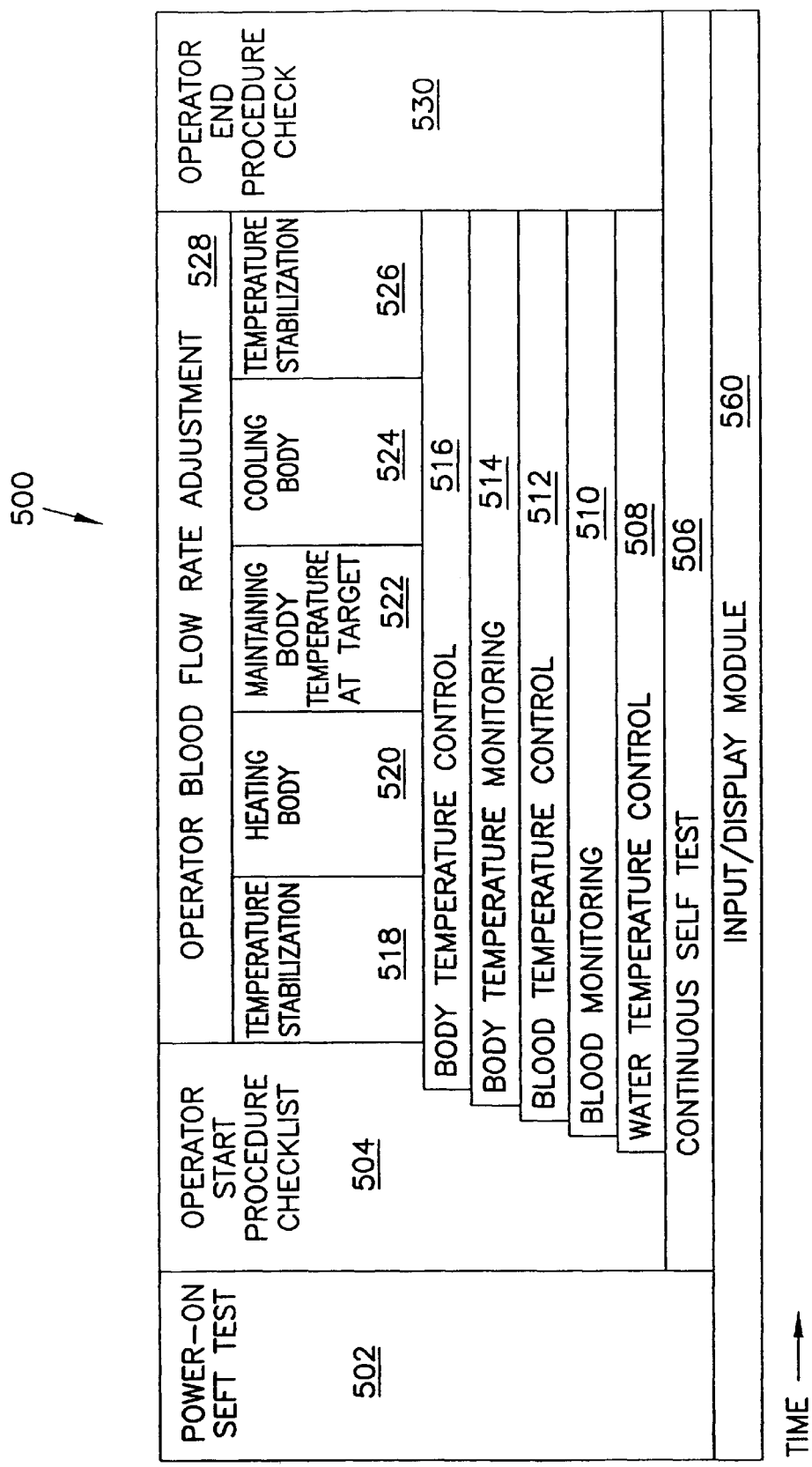
FIG. 5A illustrates one embodiment of the time sequencing between some of the various software modules which monitor and control PHTS 100.

In one embodiment, referring to both FIGS. 4 and 5A, continuous self-test module 506, water-temperature-monitoring module 507, blood-monitoring module 510, and body-temperature-monitoring module 514, are parts of plant module 456; water-temperature-control module 508 is part of water model 454; blood-temperature-control module 512 is part of blood model 452; and body-temperature-control module 516 is part of body profile/model 450.

FIG. 5A shows, for one embodiment, the major software components of software system 500 which run on computer system 110 and how they are invoked (or turned on and off) over time during a typical perfusion hyperthermia treatment. In one preferred embodiment, each software component comprises a task (or "job") which operates in a multitasking environment in computer 111. In one such embodiment, computer system 110 comprises computer 111, which is a dedicated computer board based on a high-performance Intel or Motorola microprocessor and coupled to interface circuit 120, and which communicates with an external personal computer 170 providing input device 130 and output device 160 functions, as shown in FIG. 2A. In the embodiment shown in FIG. 5A, software system 500 comprises the following components: input/display module 560, power-on self-test module 502, operator start-procedure checklist module 504, continuous self-test module 506, water temperature monitoring module 507, water-temperature-control module 508, blood-monitoring module 510, blood-temperature-control module 512, body-temperature-monitoring module 514, body-temperature-control module 516, temperature-stabilization module 518, body-heating module 520, maintaining-body-temperature-at-target module 522, body-cooling module 524, body-temperature-stabilization module 526, operator blood-flow-rate adjustment module 528, and operator end-procedure checklist module 530.

The input/display module 560 has input/output functions including 1) acquiring user input, 2) generating continuous, real-time data display, and 3) real-time data storage. This module is responsible for generating appropriate display information for the operator, acquiring and interpreting operator input, and logging appropriate information for further analysis. The stored data can be transferred to a removable medium for postoperative analysis.

In one embodiment, input/display module 560 provides for control over one or more of the following functions:

a) checklist input—asking for, receiving, and processing user input b) parameter-value selection—allowing the user to specify which parameters are measured and to specify limits for control of those parameters c) display-data selection—allowing the user to specify which data are to be displayed and the display mode (graphical versus textual, differential versus absolute, and/or scaling, etc.)

d) annotation selection—allowing the user to add annotations or explanations of events to the data being recorded e) audible-warning override—allowing the user to specify the sound associated with some or all warnings to be enabled/disabled and/or the volume or type of the sound to be adjusted. In one embodiment, alarm conditions should always cause an audible alarm regardless of the state of switch or parameter settings; and the alarm tone should continue to sound until the condition is acknowledged by the operator.

f) flow-rate adjustment—allow the user to make adjustments to the blood-pump flow rate.

g) manual control—allowing the user to adjust and control various system components, with subject-(i.e., patient 99) and operator-safety aspects still being monitored by computer system 110. In one embodiment, input/display module 560 disregards the manual-override setting if it could cause a condition hazardous to patient 99. In one embodiment, input/display module 560 continues to monitor absolute subject safety limits while operating in manual mode and limits the system outputs of PHTS 100 in a manner appropriate to any hazard detected. In one embodiment, manual overrides are provided for the following:
1) Water pump (WP) automatic/off/on
2) Heater automatic/off/on
3) Fan automatic/off/on
4) Blood pump (BP) automatic/off/rate
5) Emergency shutoff (BP, WP, heater, fan). In one embodiment, a 'pull to shut off' emergency shut off switch is provided on the disposable face of the unit. This switch is capable of simultaneously stopping the blood pump, water heater, water-cooling fan, and water pump.

Power-on self-test module 502 checks for proper operation of components which comprise or are connected to computer system 110, including checking the existence and functionality of the computer 111 and its components, the interface electronics 120, and all attached sensors. Continuous self-test module 506 is then started, and continuously verifies proper function of all subsystems of PHTS 100. Operator start-procedure checklist module 504 performs an interactive operator checklist and equipment check, interactively and/or automatically verifying (a) that PHTS 100 is properly set-up, (b) that all subsystems requiring setup and checks for proper operation have been so prepared and checked (including the input devices 130 and output devices 160 of computer 170, mounting of disposable parts of ECC 300, confirming tubing positions and flow directions, and water levels), and (c) that the patient is properly prepared ("prep'ed") for connection to PHTS 100. In one embodiment, this checklist is implemented as a one-way checklist which requires the operator or user to start a particular series of checklist procedures (or the entire checklist) from the beginning (rather than being allowed to backup a little bit in the checklist), in order to ensure that certain procedures which should be performed in a certain order maintain that order. Continuous self-test module 506 then continuously verifies continued proper function of all subsystems of PHTS 100, including checkable items which may have been connected or started from the operator checklist. Water-temperature-monitoring module 507 then starts, and measures water temperature, pressure, and level. Water-temperature-control module 508 then starts, and turns on the water pump, sets a target (preset) preheat temperature, and monitors and controls operation of the heating, cooling and pumping of water through water-conditioning subsystem 340. Blood-monitoring module 510 then starts, and monitors some or all parameters of the blood (for instance, temperature at various points in the system of PHTS 100, pressure, flow, pH, oxygen level, level of any drugs that may have been added, and/or leakage, etc.). One output of blood-monitoring module 510 is to a display in output device 160 to inform the operator of the measured parameters. Another function of blood-monitoring module 510 is to confirm the temperature-probe functionality. Blood-temperature-control module 512 controls the temperature of the blood as a function of the temperatures detected by blood-monitoring module 510. In one embodiment, before patient 99 is connected to PHTS 100, the functionality is checked by circulating sterile saline through ECC 300 and verifying that heat can successfully be both added to and removed from the saline. Body-temperature-monitoring module 514 is then started, and monitors the temperatures, rates of change of temperatures, and differential temperatures within patient 99. Body-temperature-control module 516 provides additional controls to blood-temperature-control module 512 in order to effect proper body-temperature profiles, rates of change, and absolute temperature.

The perfusion hyperthermia treatment itself is then started, comprising modules 518–526. Temperature-stabilization module 518 measures and verifies proper initial stable body temperature of patient 99 as part of body-temperature control module 516; starting at time $t_a$ and ending at time $t_b$ (see FIG. 5B), this module assures that the patient is stable within satisfactory limits (e.g., at a "normal" temperature of, for example, 37° C.), assures that all initial parameters are within proper limits, determines which probes may have fallen out or failed and whether the treatment can be continued, and provides a set of baseline and average temperatures (and other measurable parameters) for algorithm control. Starting at time $t_b$ (see FIG. 5B), body-heating module 520 measures and controls proper heating temperature rates-of-change as patient 99's temperature is ramped up to the desired treatment temperature. Starting at time $t_c$ (see FIG. 5B), maintaining-body-temperature-at-target module 522 measures and controls proper treatment-stage body temperature (for example, stabilizing patient 99's temperature at a treatment temperature of 43.5° C. for some amount of time, for example, for 20 minutes between time $t_c$ and $t_d$ (see FIG. 5B)) as part of body-temperature-control module 516. Starting at time td (see FIG. 5B), body-cooling module 524 measures and controls proper cooling temperature rates-of-change, cooling the patient back to a "normal" temperature at a controlled rate of temperature change, as part of body-temperature-control module 516. Starting at time $t_e$ and ending at time $t_f$ (see FIG. 5B), body-temperature-stabilization module 526 then measures and controls proper post-treatment temperature stabilization, verifying that the patient has indeed stabilized at their normal temperature, as part of body-temperature-control module 516. Operator blood flow-rate-adjustment module 528 allows the operator to set blood-flow rates within parameter limits set by the software, and, if necessary, to override those limits; this module also provides the operator with the capability to adjust all other thresholds and limits, such as rates of temperature change, water flow rates, etc. Operator end-procedure checklist module 530 elicits and receives operator input as to operations which must be performed and verified at the end of treatment, such as assuring that the data has been successfully written to magnetic media from data output device 163 (such as diskettes), assuring proper discontinuation of medical treatment (such as transfusion of a volume of blood to compensate for blood left in the ECC 300), and logging total perfusion time, peak and average body and tympanic temperatures.

Perfusion hyper/hypothermia treatment system (PHTS) 100 is designed to perform whole-body hyperthermia extracorporeal circulation (WBHT-ECC), systemic perfusion hyperthermia treatment (SPHT), or intraperitoneal perfusion hyperthermia treatment (IPHT). In one embodiment, PHTS 100 is to be incorporated into the operating room environment and will be part of the system for controlling and supporting the subject. One view of PHTS 100 comprises software subsystem 500, mechanical subsystem 600 which connects to patient 99 and moves the blood (or other fluid) from patient 99 through ECC 300 and perfuses the blood (or other fluid) back into patient 99, and electrical subsystem 700 which performs the monitoring of parameters and control of the treatment. In one embodiment, the PHTS 100 provides an interface directly with a disposable subsystem 301. The mechanical subsystem 600 includes a chassis that provides the attachment support for system interface 390 (into which is plugged the disposable subsystem 301) and encloses the majority of the electrical subsystem 700.

Figure 5B:
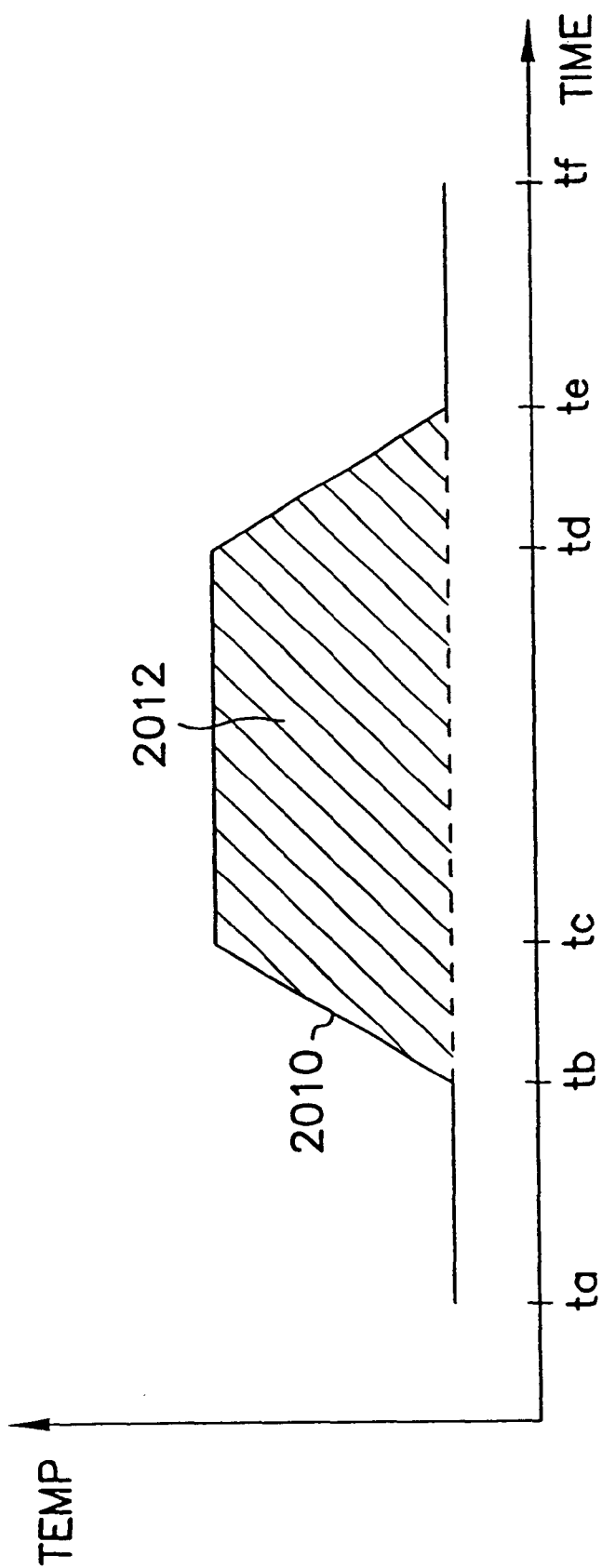
FIG. 5B shows a graph of a typical temperature vs. time for a patient 99 undergoing a perfusion hyperthermia treatment for one embodiment of PHTS 100.
Figure 5C:
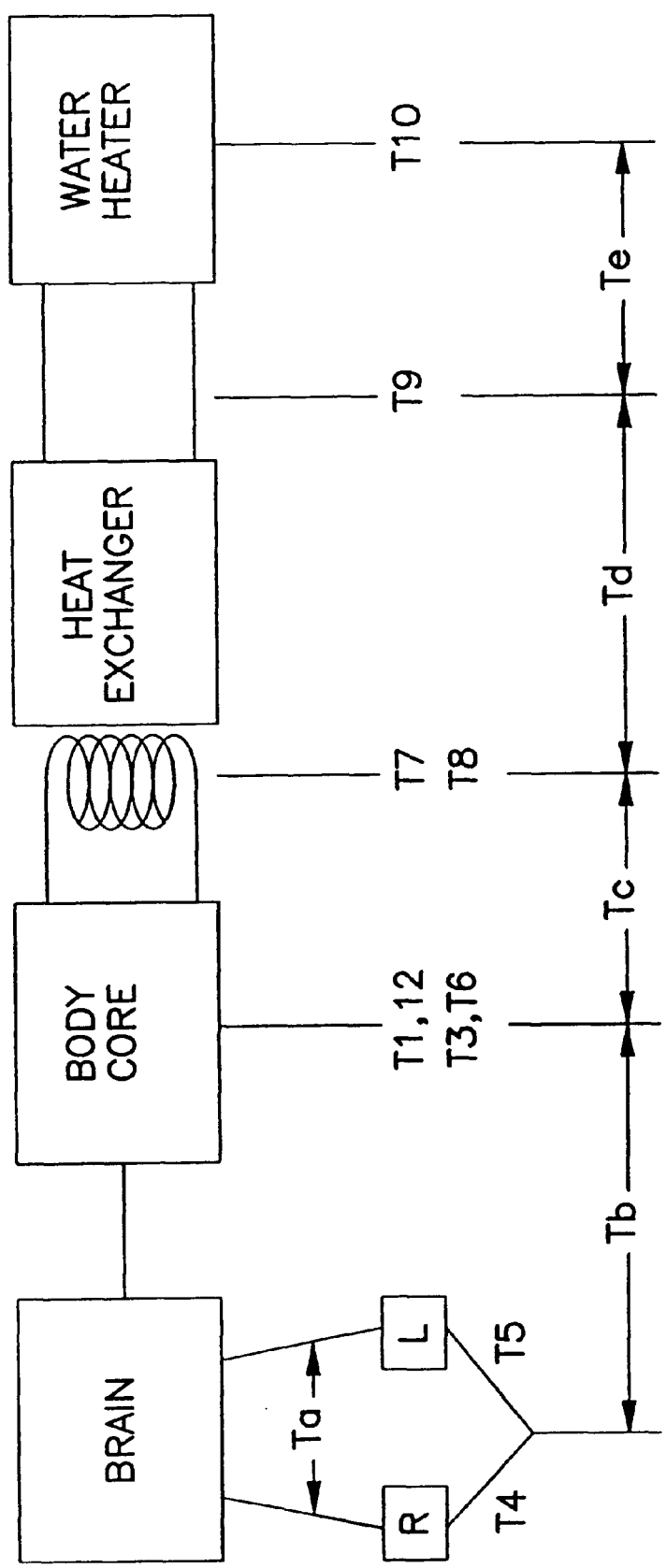
FIG. 5C illustrates a patient and system temperature model used in one embodiment of PHTS 100.

FIG. 5C illustrates a patient and system temperature model used in one embodiment of PHTS 100. (Note that, unlike FIG. 5B, here Ta through Te represent temperature differences rather than time reference points.) Temperatures T1 through T10 represent various temperatures measured throughout monitoring system 200 and ECC 300. In this model, Ta represents the difference between T4, measuring the right tympanic temperature, and T5, measuring the left tympanic temperature. It is thought important to closely control the absolute temperature reached by T4 and T5 and to minimize the difference Ta. In one embodiment, temperatures T1, T2, T3, and T6 are averaged together to calculate an average body-core temperature; T4 and T5 are averaged together to calculate an average brain temperature; and Tb is calculated as the difference between these two averages. T7 is the blood temperature at the blood inlet to heat exchanger 330, and is generally equal to the average body-core temperature. T8 is the blood temperature at the blood outlet from heat exchanger 330, and Tc is the difference between this and the average body-core temperature. Td is the temperature difference between T9 (the temperature of water entering the heat exchanger 330) and T7 (the temperature of blood entering the heat exchanger 330). Te is the temperature difference between T10 (the temperature of water leaving the water heater/cooler 350/360) and T9 (the temperature of water entering the heat exchanger 330). In one embodiment, software 500 uses predetermined parameters as maximum limits for Ta, Tb, Tc, Td, and Te, and controls heat addition/subtraction from the water in order to keep these temperature differences within the specified predetermined limits. In one embodiment, the amount of heat added or subtracted is controlled at least in part by the amount of temperature differential between the water (or other heat-exchange medium) and the blood within heat exchanger 330 (i.e., a greater temperature differential is used to transfer a greater amount of heat to or from patient 99, a lesser temperature differential is used to transfer a lesser amount of heat, and the temperature differential is reversed to reverse the direction of heat transfer). In another embodiment, the blood-flow rate is varied in order to vary the amount of heat transferred. In yet another embodiment, both temperature differential and blood-flow rate are varied in order to vary the amount of heat transferred.

FIG. 6 illustrates an exemplary display screen usable with a mouse-type point-and-click input device 130 or a touch-screen input device 130 for one portion of the software-controlled user-interactive start-up procedure checklist. FIGS. 6 through 13 represent screen displays for one embodiment; other embodiments include additional fields, or remove certain fields from the displays shown. Option menu 606 represents a typical "Windows"-type drop-down menu interface which has been modified specifically for PHTS 100 to indicate to an operator various submenus available. In one embodiment, one or more of the following submenus are available: a "file" submenu which has a plurality of file commands such as "new", "open", "save", "save as", "print", and/or "exit" which operate in a manner familiar to windows users; a "create" submenu which has a plurality of create commands such as "create new file" (which creates a new data file), "create new log" (which creates a log file for logging parameters specifiable by the operator), and/or "create new record" (which creates a new patient record); an "edit" submenu which has a plurality of edit commands such as "cut", "copy", and "paste" which are familiar to windows users, and/or "annotation" which allows the user to add an annotation (in one embodiment, a text annotation is provided, wherein the user types in a textual annotation using a keyboard, in another embodiment, a voice annotation is provided which allows the user to record a voice recording of the annotation desired in a manner known to the multimedia computer art) to a particular event (e.g., if an unusual event occurs during the surgery treatment, the doctor or perfusion technician can have a textual annotation typed in or voice annotation recorded and added to the data log kept by computer 111, thus explaining the conditions present at the event which may not be evident from the measured and recorded parameters alone); a "view" submenu which has a plurality of view commands such as "show graphical view" (which changes the display mode to a mode which presents data in a graphical manner), "show textual view" (which changes the display mode to a mode which presents data in a textual or tabular form), "select parameters to graph and compare" (which allows the operator to choose which parameters are displayed and/or compared), and/or "select parameters to compare" (which allows the operator to choose which parameters are compared); an "options" submenu which has a plurality of options commands such as "monitor only" which directs PHTS 100 to only monitor parameters (such as temperature) without attempting automatic control, "monitor and control" which directs PHTS 100 to monitor and automatically control the measured parameters to a specified profile, "simulation" which directs computer 111 to simulate a perfusion hyperthermia treatment session as if a patient with specified attributes were connected to PHTS 100 (used for developing software and user interfaces of PHTS 100), and/or "training" which also directs computer 111 to simulate a perfusion hyperthermia treatment session as if a patient with specified attributes were connected to PHTS 100 and also provides explanatory text to explain to the user what is happening and medical background regarding certain parameters and how they change and what it means when they change in a certain way, and also measures operator responses and timing to particular simulated emergency events (used to train medical personnel as to the use of the machine and what to do in exigent situations—such as if the patient might "go critical" in the middle of an operation); a "preferences" submenu) which allows the user to customize the presentation of data and the user input/output interface); and a "return!" submenu (which immediately returns the user to the just-previous menu or display mode).

Title field 608 displays an indication (viz., "WATER CIRCUIT CHECKLIST PAGE 1 OF 8") of which checklist is being interactively filled in presently (or how it was previously filled in), and where the user currently is in the sequence of checklists. Field 638 provides an operator input "button" which is activated by the operator (for example, by moving a mouse pointer to the button icon on the screen, and pressing a switch on the mouse device of input device 130) to indicate that the operator has verified that PHTS 100 power has been turned on and the power-supply cord has been secured to the wall-power outlet. Field 612 provides a check-box icon and an associated descriptor to indicate that the heat exchanger 330 has been connected to the water supply. Field 638 and field 612 show alternative embodiments of an interactive checklist which presents the operator with new action items as the operator completes the action currently indicated on the screen. Field 616 indicates the operator has verified that the water reservoir has been filled properly. Field 640 is an example of an output-only field which indicates "LOW" until enough water has been provided, "OK" when properly filled within low and high limits, and "HIGH" when too much water has been added (one embodiment uses the "WATER HIGH" indication during the treatment to indicate a possible leak of blood into the water system). Fields 612, 616, and 640 are grouped on the display under the title "WATER CIRCUIT." Field 620 indicates whether the operator has verified that the water temperature probe at the "into" port of the heat exchanger 330 has been connected and calibrated properly. Field 642 is an output-only field which indicates the digital temperature value of the probe checked at box 620. Similarly, field 624 indicates whether the operator has verified that the water-temperature probe at the "out of" port of the heat exchanger 330 has been connected and calibrated properly. Field 644 is an output-only field which indicates the digital temperature value of the probe checked at box 624. Field 620 indicates whether the operator has verified that the water pump is ready to start. Field 646 (and the ALT-B key combination) indicate the operator desires to skip the checklist process (perhaps due to an emergency which supersedes the normal desirability of proceeding through the checklist process) and go immediately to the automatic or manual control mode. If field 646 is activated and control is moved to the automatic or manual control mode, the user can later go back and complete the checklists after the emergency has been handled. In one embodiment, field 646 allowing bypassing of the checklist process is provided on every checklist display screen.

Figure 7:
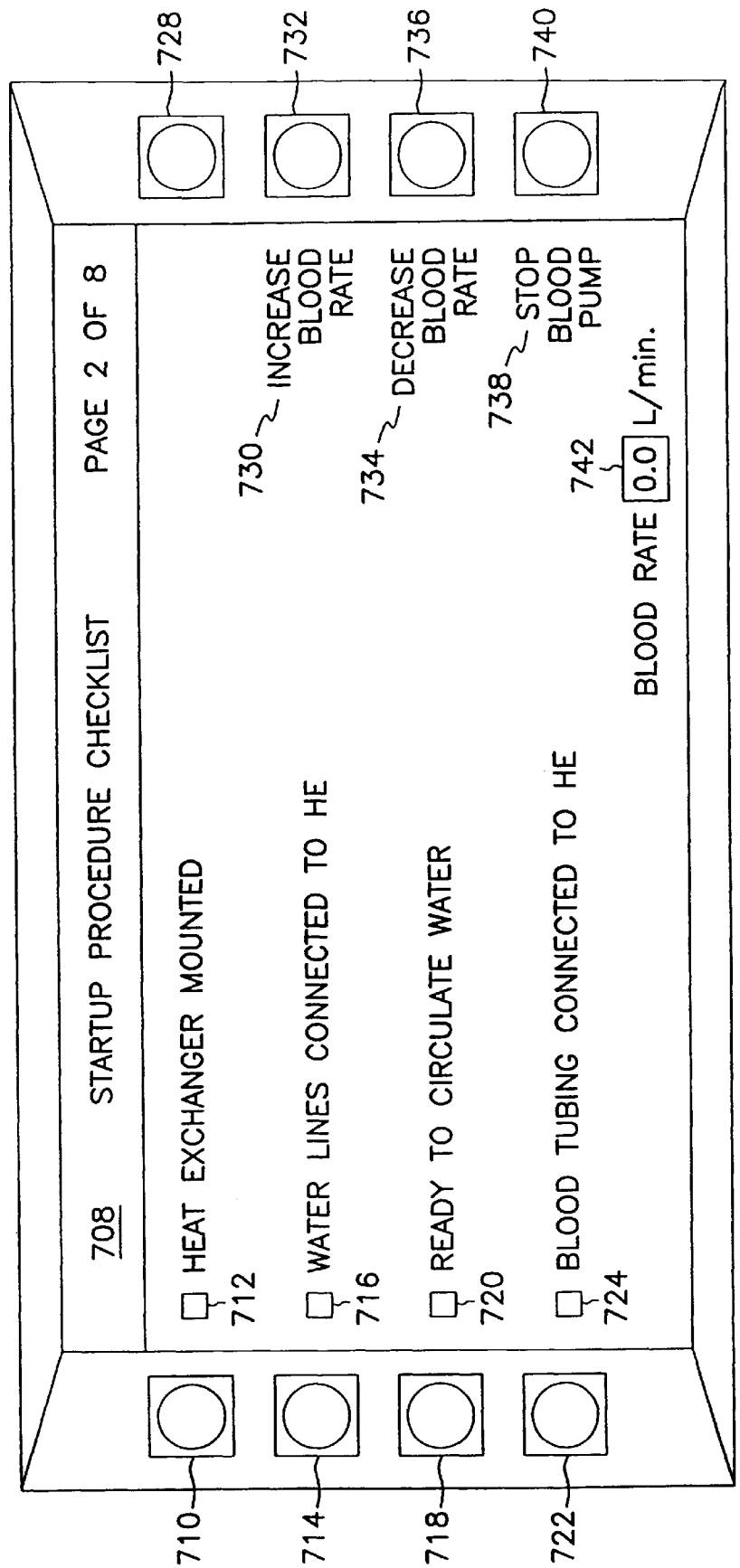
FIG. 7 illustrates an exemplary display screen and bezel buttons of a second portion of the software-controlled user-interactive start-up-procedure checklist.

FIGS. 6 and 7 illustrate exemplary display screens and input device options portions of the software-controlled user-interactive start-up procedure checklist. FIGS. 6 and 7 illustrate embodiment alternatives for output display 161 and input device 130: FIG. 6 is directed towards an interactive interface in which the user provides input using a mouse-type point-and-click input device 130 or a touch-screen input device 130; wherein the user is presented a plurality of windows-type screens and uses the mouse-type pointer (or a touch-screen) to interact. FIG. 7 is directed towards a bezel-button interface, wherein the text displayed next to a button-type switch indicates the function of that button, and this text changes from screen-to-screen, changing the function of the associated buttons as well. Some of the functions indicated on FIGS. 6 and 7 overlap since they are from separate checklist embodiments which address substantially identical functions.

On FIG. 7, title field 708 displays an indication (viz., "STARTUP PROCEDURE CHECKLIST PAGE 2 OF 8") of which checklist is being interactively filled in presently (or how it was previously filled in), and where the user currently is in the sequence of checklists. Field 712 provides a check-box icon and an associated descriptor to indicate that the heat-exchanger interface 331 has been mounted within heat exchanger 330; bezel button 710, when pressed by a user, activates this function for this display screen. Field 716 provides a check-box icon and an associated descriptor to indicate that the water lines are connected to heat exchanger 330; bezel button 714, when pressed by a user, activates this function for this display screen. Field 720 provides a check-box icon and an associated descriptor to indicate that the heat-exchanger 330 is ready to circulate water; bezel button 710, when pressed by a user, activates this function for this display screen; the circulation of water begins after buttons 718 and 722 have both been pressed. Field 724 provides a check-box icon and an associated descriptor to indicate that the blood tubing 302 has been connected to heat-exchanger interface 331; bezel button 722, when pressed by a user, activates this function for this display screen. Field 730 (which, in this example, has no check-box icon) has a descriptor for increasing blood-flow rate through blood pump 320; bezel button 732, when pressed by a user, activates this function for this display screen and increases blood-flow rate, which is indicated in output-only field 742, showing the flow rate in liters per minute. In one embodiment, for each activation of button 732 (i.e., for each press of the button by the operator), the blood rate is increased by a specified amount, for example, by 0.1 liter per minute. Field 734 has a descriptor for decreasing blood-flow rate through blood pump 320; bezel button 736, when pressed by a user, activates this function for this display screen and decreases blood-flow rate. In one embodiment, for each activation of button 736, the blood rate is decreased by a specified amount, for example, by 0.1 liter per minute. Field 738 has a descriptor for stopping blood pump 320; bezel button 740, when pressed by a user, activates this function for this display screen and stops blood pump 320.

Figure 8:
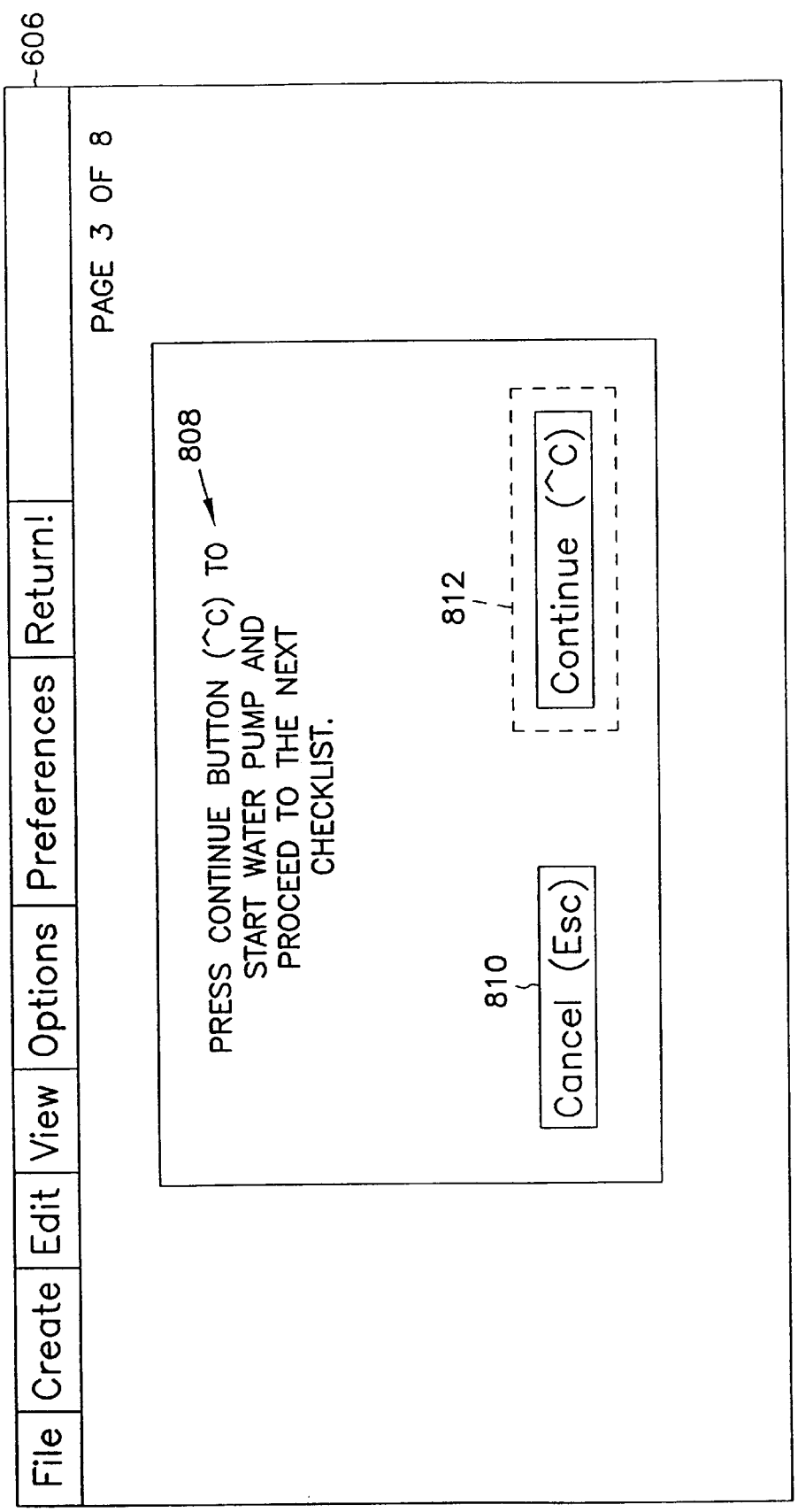
FIG. 8 illustrates an exemplary display screen usable with a mouse-type point-and-click input device for a third portion of the checklist.

FIG. 8 illustrates an exemplary display screen usable with a mouse-type point-and-click input device 130 or a touch-screen input device 130 for a third portion of the checklist. For FIG. 8, no title field is provided; only an indication of where the user currently is in the sequence of checklists ("PAGE 3 OF 8"). Field 812 provides a button icon and its associated descriptor to indicate that the button ("CONTINUE"), if pressed, will start the water pump and proceed to the next checklist screen (alternatively, the user may press the alt-C key combination to accomplish the same function). Field 810 provides a button icon and its associated descriptor to indicate that the button ("CANCEL"), if pressed, will not start the water pump, but will proceed to the next checklist screen (alternatively, the user may press the "Esc" key to accomplish the same escape function).

FIG. 9 illustrates an exemplary display screen usable with a mouse-type point-and-click input device 130 or a touch-screen input device 130 for a fourth portion of a checklist. On FIG. 9, title field 908 displays an indication (viz., "PERFUSION CIRCUIT CHECKLIST PAGE 4 OF 8") of which checklist is being interactively filled in presently (or how it was previously filled in), and where the user currently is in the sequence of checklists. Field 910 provides a check-box icon and an associated descriptor to indicate that the blood tubing 302 (i.e., the blood-pump interface 321) has been mounted to the blood pump 320 so that blood flow travels in the proper direction (note that one embodiment of the present invention provides a disposable circuit 301 and system interface 390 designed so that proper mounting and thus proper blood-flow direction is assured). Field 912 provides a check-box icon and an associated descriptor to indicate that proper occlusion of the blood tubing 302 is present at this point in the procedure (i.e., that the blood-pump interface 321 has been adjusted to the blood pump 320 so that the tubing is properly pinched by the rollers; note that one embodiment of the present invention provides a blood-pump interface 321 and blood pump 320 which are designed to mate so that proper adjustment and thus proper blood-flow occlusion are assured—see the descriptions for FIGS. 14A–14K below). Field 914 provides a check-box icon and an associated descriptor to indicate that the blood tubing 302 been properly connected to heat exchanger 330 (note for each of these similar checkboxes that one embodiment of the present invention provides a disposable circuit 301 and system interface 390 designed so that proper mounting and thus proper blood connections are assured). Field 916 provides a check-box icon and an associated descriptor to indicate that the perfusion circuit 400 is securely mounted to patient 99. Field 918 provides a checkbox icon and an associated descriptor to indicate that the blood-pressure sensor in detector 335 is properly connected. Field 920 provides a check-box icon and an associated descriptor to indicate that the blood-pressure sensor in detector 336 is properly connected. The previous checklist is grouped under the title "PERFUSION CIRCUIT."

The following checklist is grouped under the title "BLOOD TEMP PROBES CONNECTED AND FUNCTIONAL": Field 922 provides a check-box icon and an associated descriptor to indicate that the temperature probe in detector 335 measuring blood temperature at the blood ingress point of heat exchanger 330 is connected and functional. Output-only field 940 indicates the temperature measured by detector 335. Field 924 provides a check-box icon and an associated descriptor to indicate that the temperature probe in detector 336 measuring blood temperature at the blood egress point of heat exchanger 330 is connected and functional. Output-only field 942 indicates the temperature measured by detector 336.

Fields 926 and 928 provide check-box icons and associated descriptors to indicate that the bubble detector 333 has been checked and that blood tubing 302 has been connected, respectively. Output-only field 944 indicates the bubble detector is clear of bubbles, or, if a bubble is detected by bubble detector 333, shows a warning or alarm. Field 930 provides a check-box icon and an associated descriptor to indicate that the PHTS 100 is ready to prime the perfusion circuit with saline, blood, or other suitable fluid.

In a manner similar to that described for FIG. 7, the blood-flow rate can be controlled, as shown at the bottom of the screen of FIG. 9. Field 934 has an icon for increasing blood-flow rate through blood pump 320, and when activated by a user, increases blood-flow rate. The blood-flow rate is indicated in output-only field 932, showing the flow rate in liters per minute. Field 936 has an icon for decreasing blood-flow rate through blood pump 320, and when activated by a user, decreases blood-flow rate. Field 938 has a descriptor for stopping blood pump 320; when activated by a user, this function stops blood pump 320.

Figure 10:
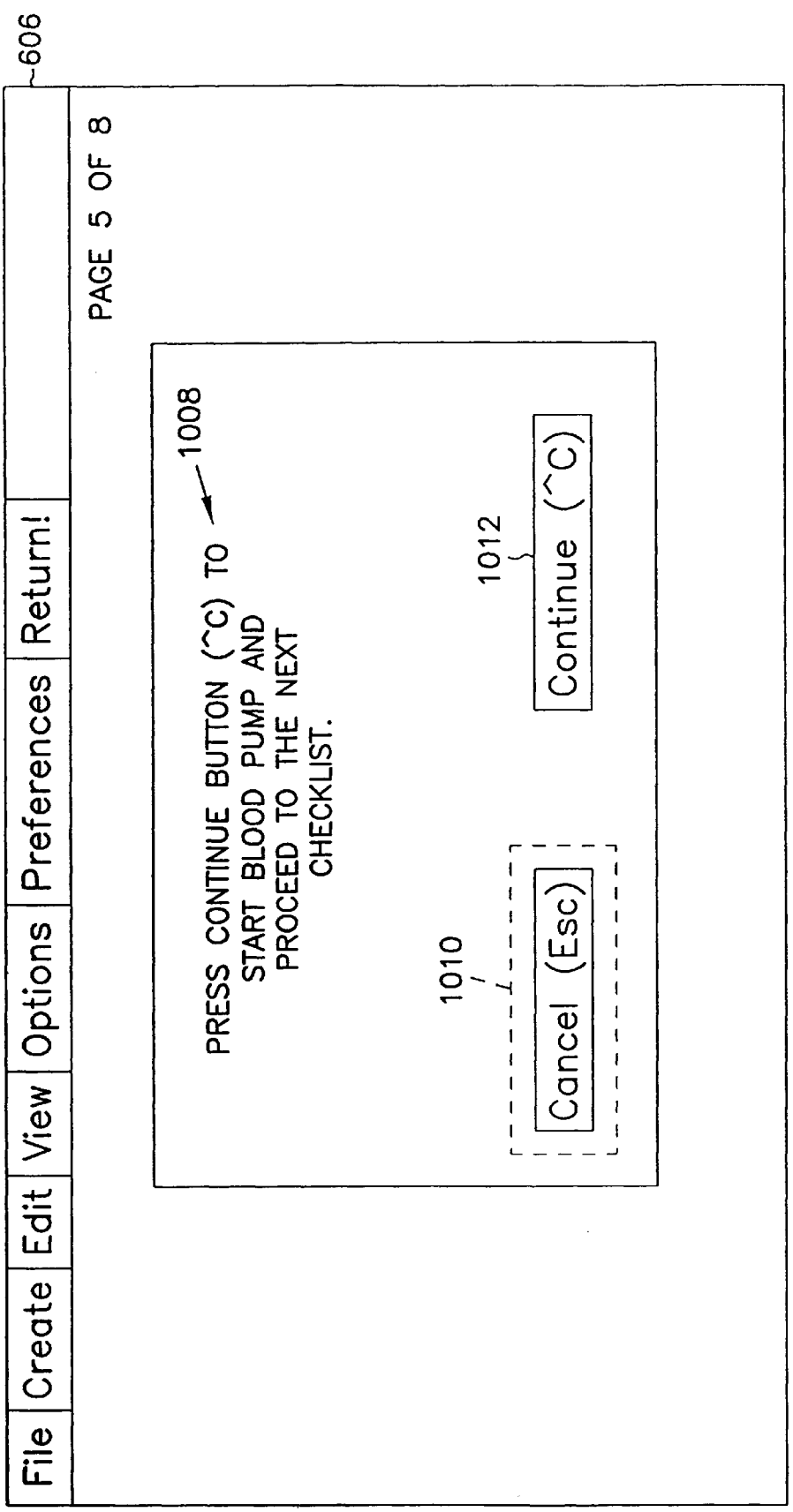
FIG. 10 illustrates an exemplary display screen usable with a mouse-type point-and-click input device for a fifth portion of the checklist.

FIG. 10 illustrates an exemplary display screen usable with a mouse-type point-and-click input device for a fifth portion of a checklist, similar to FIG. 8. For FIG. 10, no title field is provided; only an indication of where the user currently is in the sequence of checklists ("PAGE 5 OF 8"). Field 1012 provides a button icon and its associated descriptor to indicate that the button ("CONTINUE"), if pressed, will start the blood pump and proceed to the next checklist screen (alternatively, the user may press the alt-C key combination to accomplish the same function). Field 1010 provides a button icon and its associated descriptor to indicate that the button ("CANCEL"), if pressed, will not start the blood pump, but will proceed to the next checklist screen (alternatively, the user may press the "Esc" key to accomplish the same escape function).

FIG. 11 illustrates an exemplary display screen usable with a mouse-type point-and-click input device for a sixth portion of the checklist, primarily for the priming of the perfusion circuit. Title field 1108 provides an indication of where in the sequence of checklists the user currently is ("PAGE 6 OF 8"). Output-only field 1114 indicates the bubble detector is clear of bubbles, or, if a bubble is detected by bubble detector 333, shows a warning or alarm. In one embodiment, flashing light spot 1124 flashes a warning or alarm color (such as yellow or red, respectively) if a bubble is detected; in one such embodiment, an audio alarm is also sounded through speaker 162. In the embodiment shown, output-only field 1116 shows the elapsed time since the last bubble was detected, output-only field 1120 shows a target value for the parameter shown in field 1116 (in this example, it is desired that at least 2 minutes pass after the last bubble is detected before the PHTS 100 is connected to a patient 99); and flashing light spot 1126 flashes a warning color (such as yellow) if the time since the last bubble is less than the target time; in one such embodiment, a soft audio alarm is also sounded through speaker 162. Output-only field 1118 shows the temperature of the perfusion circuit (i.e., the temperature of the perfusate within ECC 300), field 1122 shows the target value for this parameter, and flashing light spot 1128 flashes a warning or alarm color (such as yellow or red, respectively) if the temperature is slightly or grossly, respectively, out of the target range. Field 1112 provides a button icon and its associated descriptor to indicate that the button ("CONTINUE"), if pressed, will proceed to the next checklist screen (alternatively, the user may press the alt-C key combination to accomplish the same function). Field 1110 provides a button icon and its associated descriptor to indicate that the button ("CANCEL"), if pressed, will proceed to the previous checklist screen (alternatively, the user may press the "Esc" key to accomplish the same escape function).

FIG. 12 illustrates an exemplary display screen usable with a mouse-type point-and-click input device for a seventh portion of the checklist, primarily for patient 99. Title field 1208 provides an indication of where the user currently is in the sequence of checklists ("SUBJECT PROCEDURE CHECKLIST PAGE 7 OF 8"). An exemplary anesthesia protocol is shown, with checkbox field 1210 completed by the user when the fluid administration lines are primed, checkbox field 1212 completed by the user when the heparin procedure is complete, and checkbox field 1214 completed by the user when the anesthetic procedure is completed. Checkbox fields 1216–1225 are checked (completed) by the user after the corresponding left tympanic, right tympanic, esophageal, indwelling, rectal/bladder and/or rectal temperature probes are connected and functionally tested; the output-only fields 1226–1235 show the temperatures as measured by the corresponding probes indicated by fields 1216–1225, respectively. Output-only fields 1236–1237 show the temperatures as measured by two other temperature probes which are not committed to a control-type measurement function. Output-only fields 1240–1241 show the flow rate and pressure of the blood inside ECC 300. Other fields have functions as previously described for other screen Figures.

FIG. 13 illustrates an exemplary display screen usable with a mouse-type point-and-click input device for a eighth portion of the checklist, which in this case is a second portion of the "SUBJECT PROCEDURE CHECKLIST" which is "PAGE 8 OF 8" of one exemplary checklist. Checkbox 1310 is checked-off to indicate that the user has turned off the blood pump (which was "on" in order to prime and test the perfusion circuit in ECC 300). Checkbox 1312 is checked-off to indicate that the user has connected the blood lines to patient 99. Other fields have functions as previously described for other screen Figures.

Figure 14B:
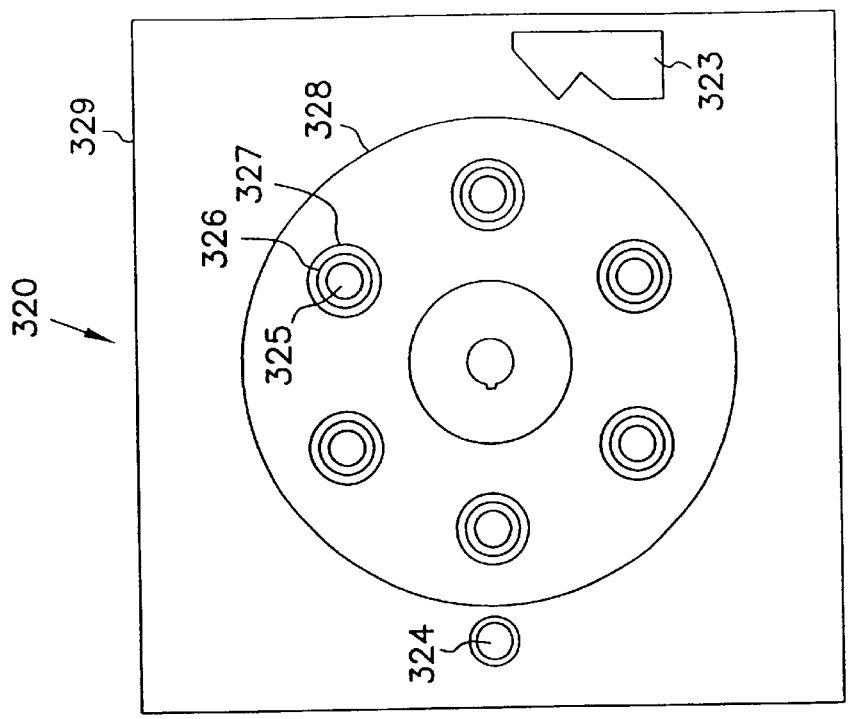
FIG. 14B is a simplified plan view of the blood pump 320 shown in FIG. 14A.
Figure 14A:
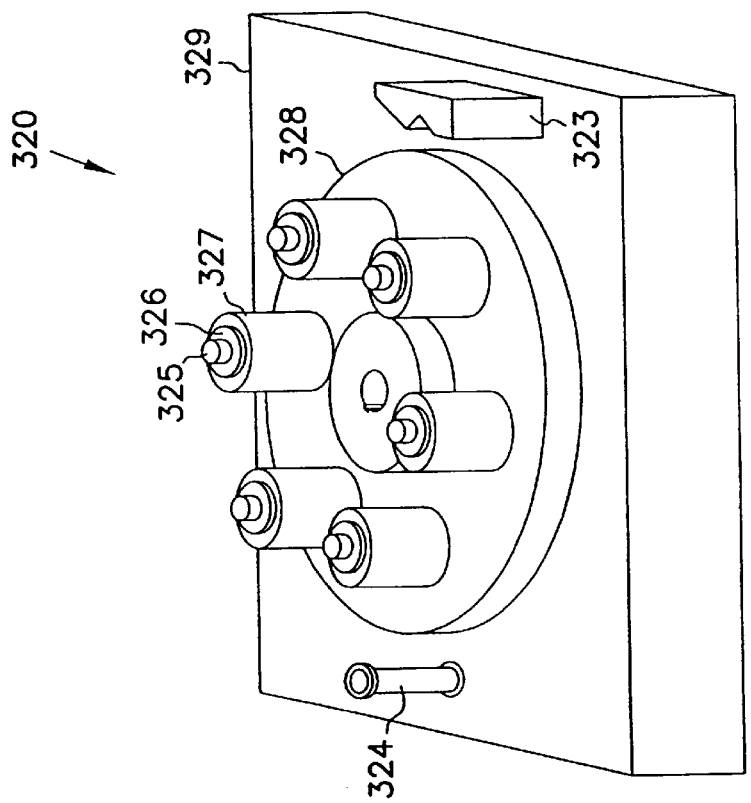
FIG. 14A is a simplified isometric view of one embodiment of blood pump 320.

FIG. 14A is a simplified isometric view of one embodiment of blood pump 320. FIG. 14B is a simplified plan view of the blood pump 320 shown in FIG. 14A. Base 329 provides a mounting structure and cover for other components such as the motor. Plate 328 is coupled to the motor, and rotates (in one embodiment, clockwise), thus successively engaging rollers 327 to squeeze tubing and thus move the blood contained therein. Pin 325 and washer 326 attach roller 327 to plate 328. Pin 324 is provided to engage a corresponding hook on one side of blood-pump interface 321. Spring-loaded retainer 323 holds the other side of blood-pump interface 321. In one embodiment, spring-loaded retainer 323 includes a screw-adjustable tension mounting which can be adjusted in order to provide (when a typical blood-pump interface 321 is mounted to blood pump 320) a proper amount of occlusion (or squeezing) to the portion of deformable blood tubing 302 which is inside a typical blood-pump interface 321, and this adjustment can then be left fixed, thus providing the proper amount of occlusion for all substantially similar blood-pump interfaces 321 which are later mounted to that blood pump 320. In another embodiment, blood-pump interface 321, blood pump 320 and one or more spring-loaded retainers 323 are manufactured to sufficiently close tolerances such that the proper amount of occlusion is achieved for all substantially similar corresponding blood-pump interfaces 321 which are later mounted to that blood pump 320, even without manual adjustments.

FIG. 14C is a plan (or front) view of one embodiment of blood-pump interface 321 which mates with the blood pump shown in FIGS. 14A and 14B. FIG. 14D is a left elevation view, FIG. 14E is a bottom elevation view, FIG. 14F is a right elevation view, and FIG. 14G is a top elevation view of the blood-pump interface 321 shown in FIG. 14C. The positioning of pin 324 and spring-loaded retainer 323, the size (both inner and outer diameter) and material of blood tubing 302, and the size and shape of blood-pump interface 321 are designed to minimize or eliminate the manual adjustments which are typically required of conventional blood pumps. In one embodiment, this is accomplished by providing a screw adjustment to spring-loaded retainer 323 which, once set, will maintain proper adjustment for all similarly made blood-pump interfaces 321.

Figure 14I:
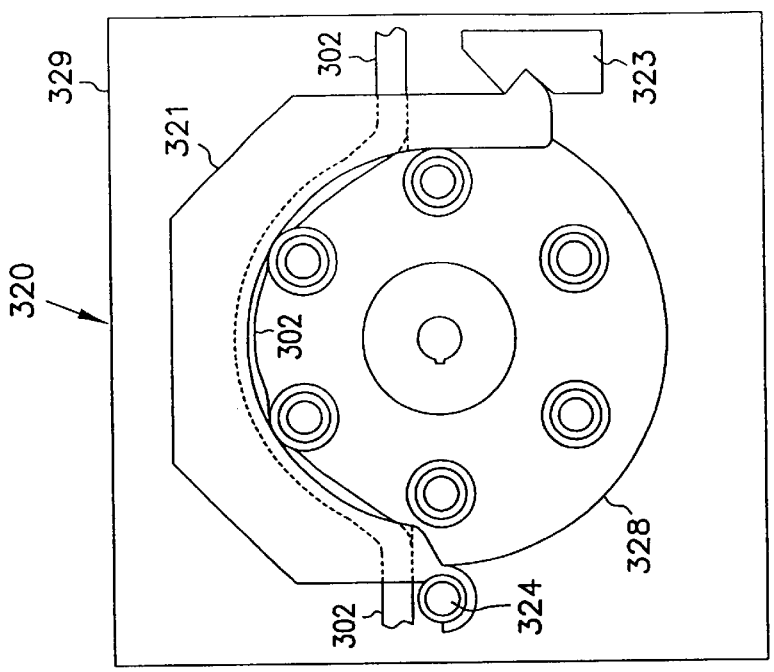
FIG. 14I is a simplified plan view of blood-pump interface 321 assembled to the blood pump 320 shown in FIG. 14A.
Figure 14H:
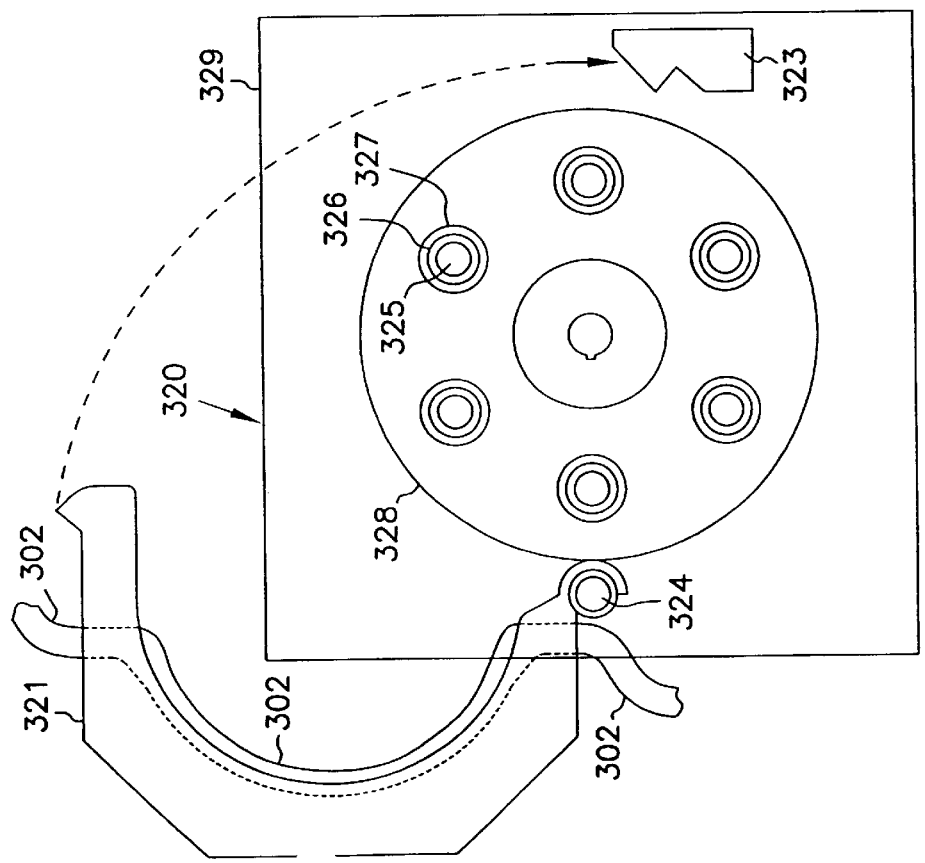
FIG. 14H is a simplified plan view of the assembly operation of blood-pump interface 321 to the blood pump 320 shown in FIG. 14A.

FIG. 14H is a simplified plan view of the assembly operation of blood-pump interface 321 to the blood pump 320 shown in FIG. 14A, wherein the hook portion of blood-pump interface 321 is first engaged to pin 324, and blood-pump interface 321 is then rotated into place and secured by spring-loaded retainer 323. FIG. 14I is a simplified plan view of blood-pump interface 321 assembled to the blood pump 320 shown in FIG. 14A.

Figure 15B:
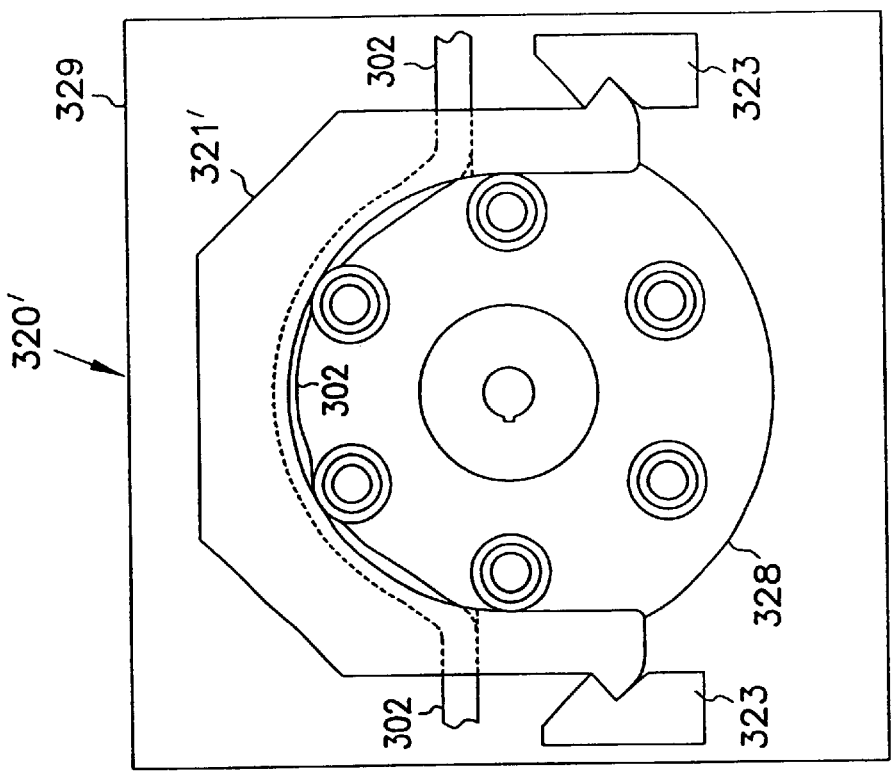
FIG. 15B is a simplified plan view of blood-pump interface 321' assembled to a corresponding blood pump 320'.
Figure 15A:
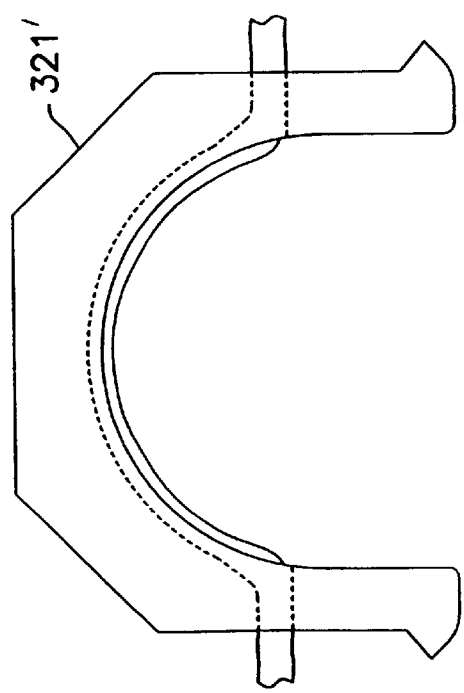
FIG. 15A is a plan view of an alternative embodiment of blood-pump interface 321'.

FIG. 15A is a plan view of an alternative embodiment of blood-pump interface 321', wherein both sides of blood-pump interface 321' are provided with protrusions to engage with spring-loaded retainers 323. In an alternative embodiment, the sides of blood-pump interface 321' are made of a resilient material such as plastic, and provide the spring function, whereas the two retainers 323 are rigidly fixed or adjustably fixed.

FIG. 15B is a simplified plan view of blood-pump interface 321' assembled (i.e., snapped into place) to a corresponding blood pump 320'. In one embodiment, one or both spring-loaded retainers 323 include a screw-adjustable tension mounting which can be adjusted in order to provide (when a typical blood-pump interface 321' is mounted to blood pump 320') a proper amount of occlusion (or squeezing) to the portion of deformable blood tubing 302 which is inside a typical blood-pump interface 321', and this adjustment can then be left fixed, thus providing the proper amount of occlusion for all substantially similar blood-pump interfaces 321' which are later mounted to that blood pump 320'. In another embodiment, blood-pump interface 321', blood pump 320' and spring-loaded retainers 323 are manufactured to sufficiently close tolerances such that the proper amount of occlusion is present for all substantially similar corresponding blood-pump interfaces 321' which are later mounted to that blood pump 320', even without manual adjustments.

Figure 16A:
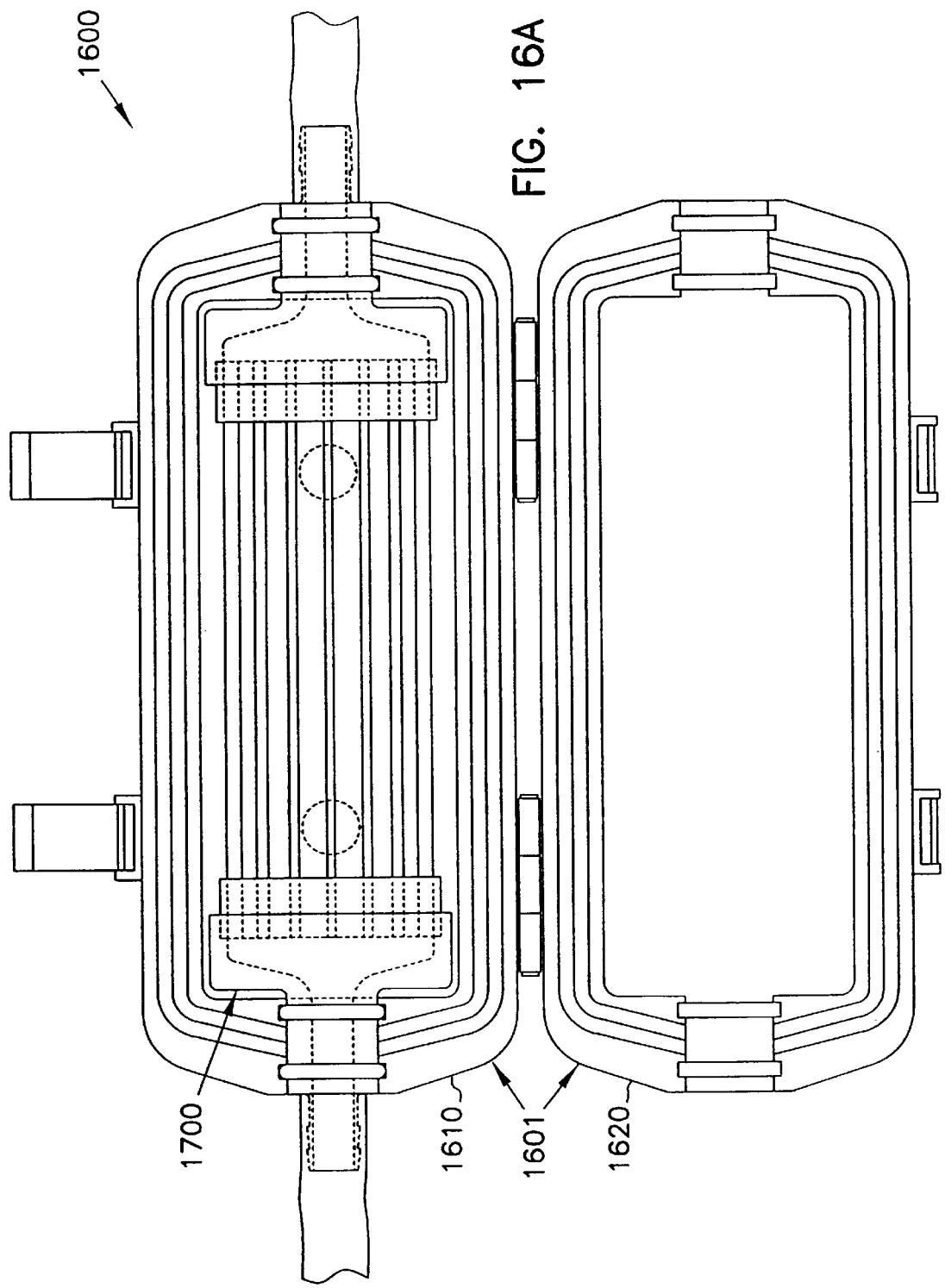
FIG. 16A shows a front, open, view of a modular clam-shell heat exchanger 1600 according to the present invention which can be used as heat exchanger 330 in PHTS 100.

FIG. 16A shows a front, open, view of one embodiment of a modular clam-shell heat exchanger 1600 according to the present invention which can be used for heat exchanger 330 in PHTS 100. Modular clam-shell heat exchanger 1600 comprises a disposable blood-tube assembly 1700 which is assembled within a reusable clam-shell assembly 1601 for use. FIG. 16a shows blood-tube assembly 1700 in place within clam-shell half 1610 of clam-shell assembly 1601 before clam-shell half 1620 of clam-shell assembly 1601 has been closed and latched for use. In one embodiment, a heat-exchanger door-interlock switch is provided to signal to computer system 110 whether or not clam-shell assembly 1601 is properly closed onto blood-tube assembly 1700.

Figure 16B:
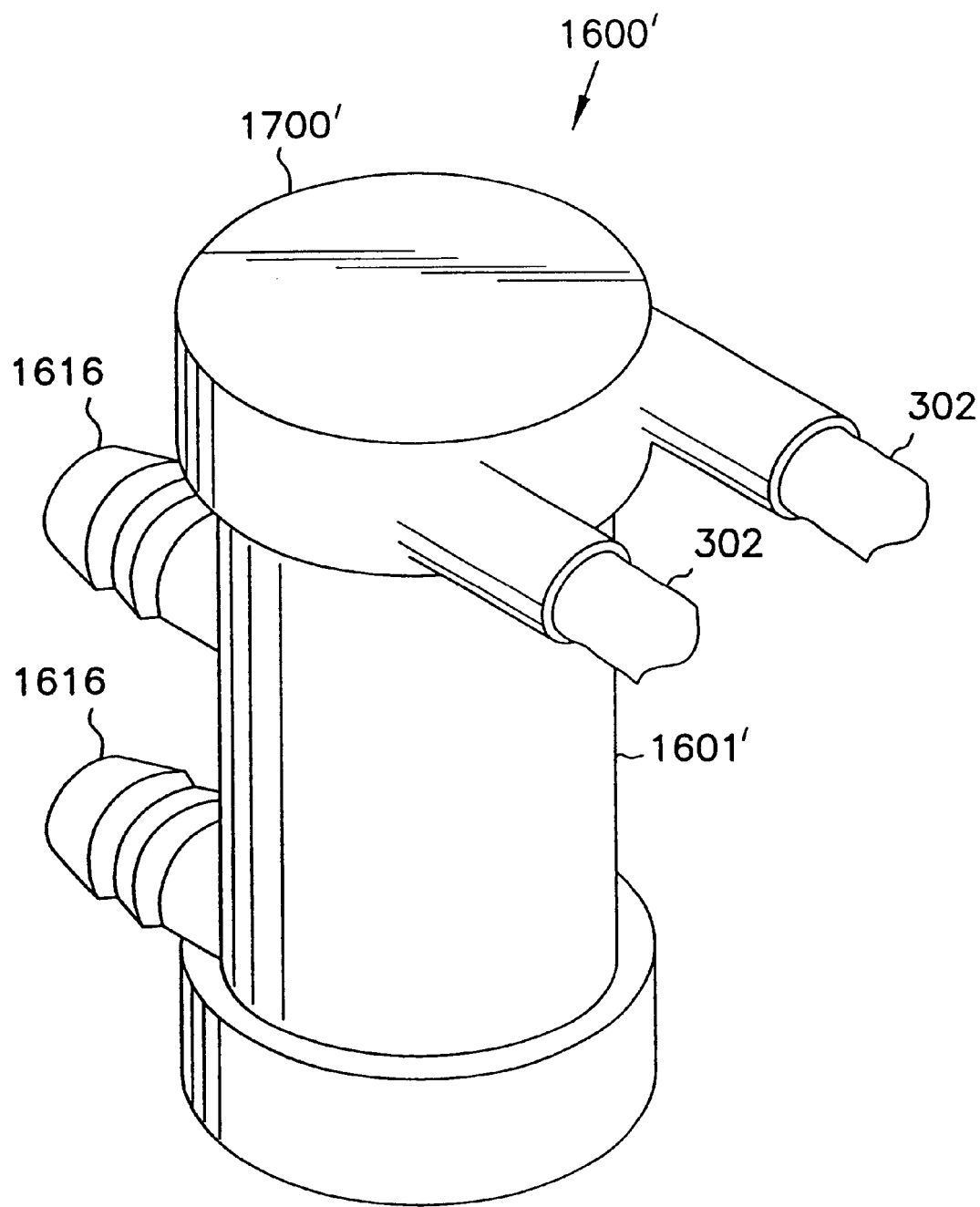
FIG. 16B shows a simplified isometric view of a modular vertical-cylinder heat exchanger 1600' according to the present invention which can be used for heat exchanger 330 in PHTS 100.
Figure 16C:
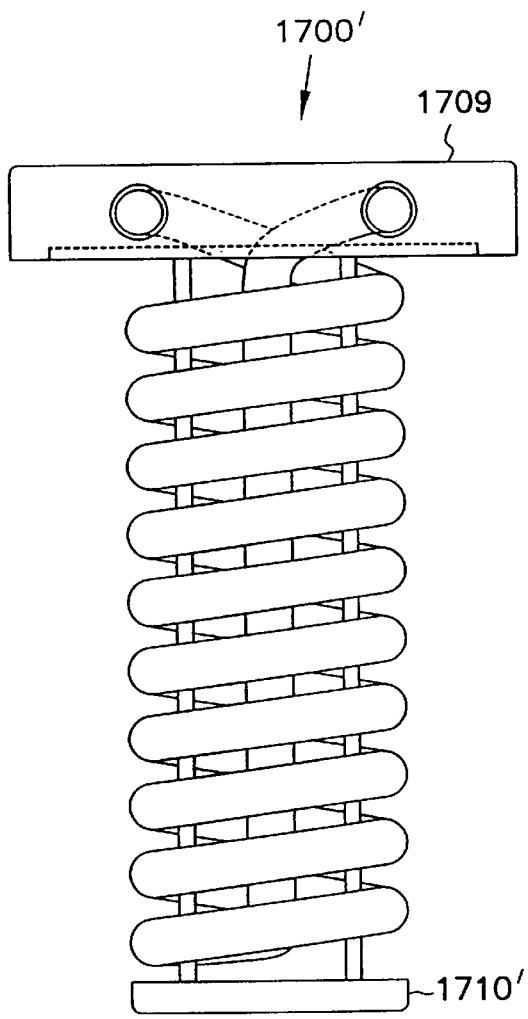
FIG. 16C shows a front view of a disposable blood-tube assembly 1700' according to the present invention which can be used in modular vertical-cylinder heat exchanger 1600' of FIG. 16B.
Figure 16D:
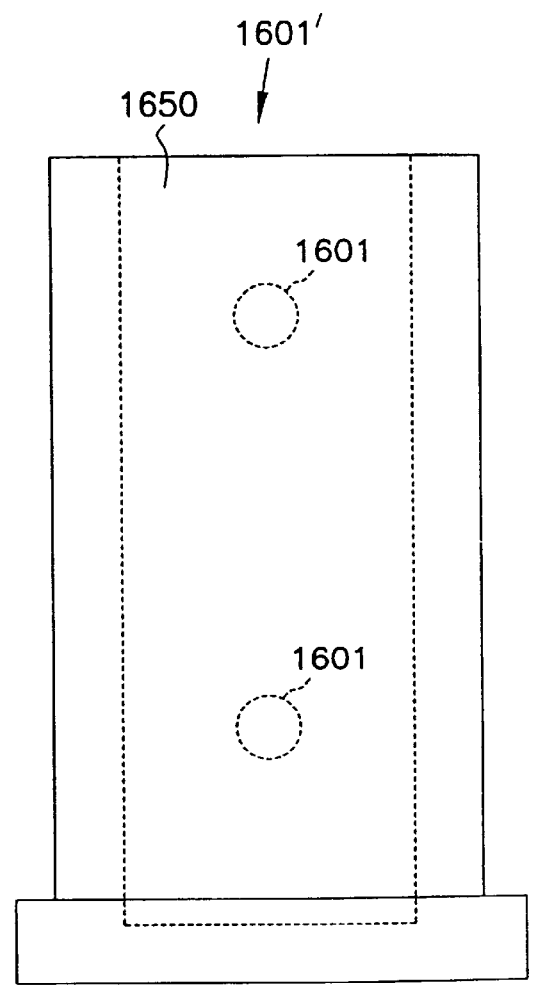
FIG. 16D shows a simplified front view of a reusable vertical-cylinder assembly 1601' according to the present invention which can be used in modular vertical-cylinder heat exchanger 1600' of FIG. 16B.
Figure 19:
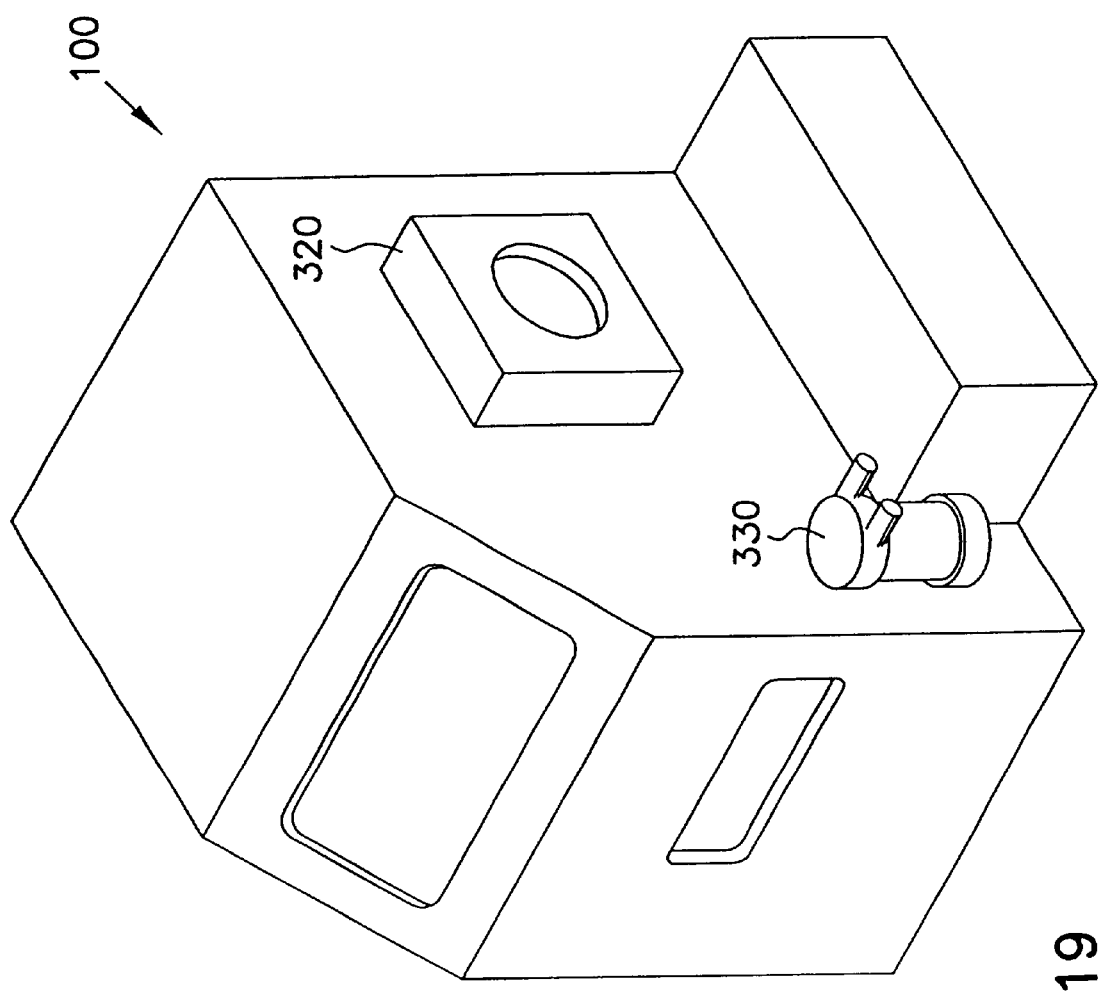
FIG. 19 shows an isometric view of a cover structure for one embodiment of PHTS 100.
Figure 20:
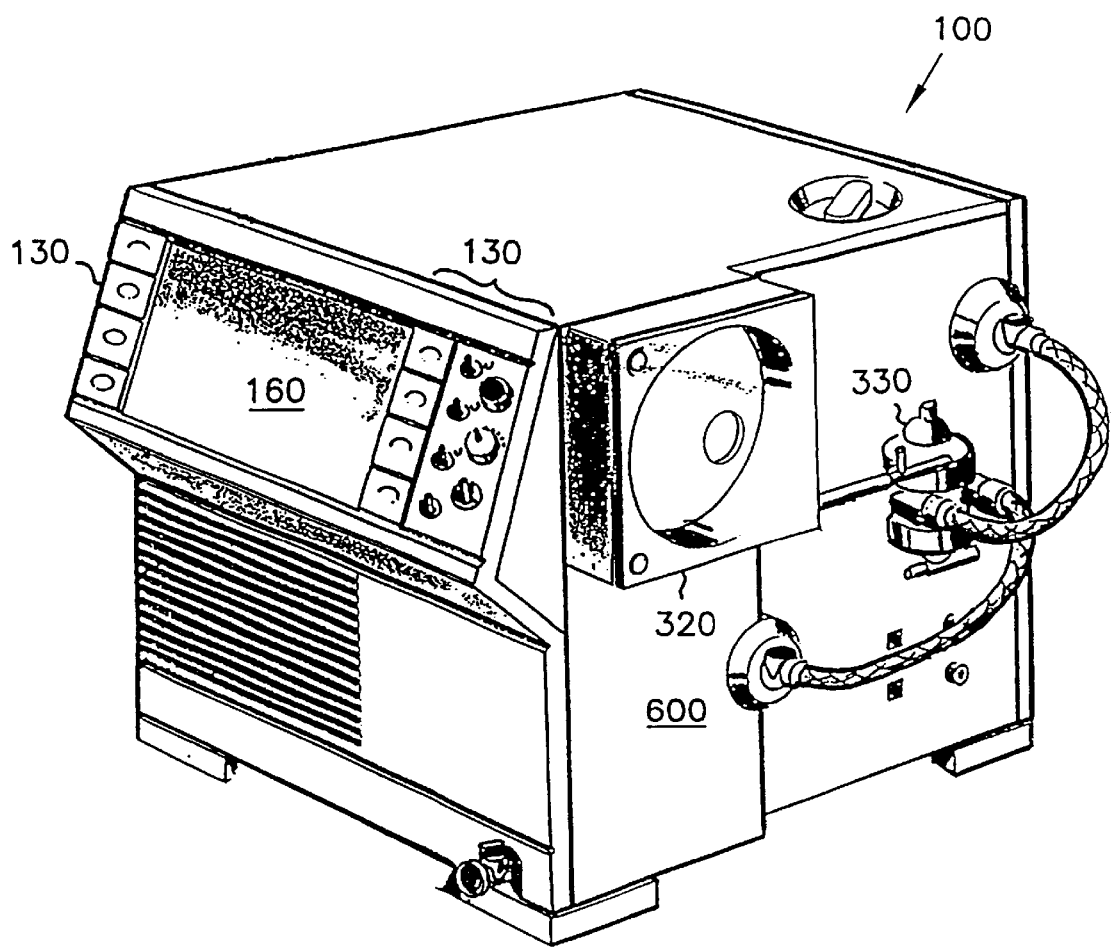
FIG. 20 shows an isometric view of one embodiment of PHTS 100.
Figure 21:
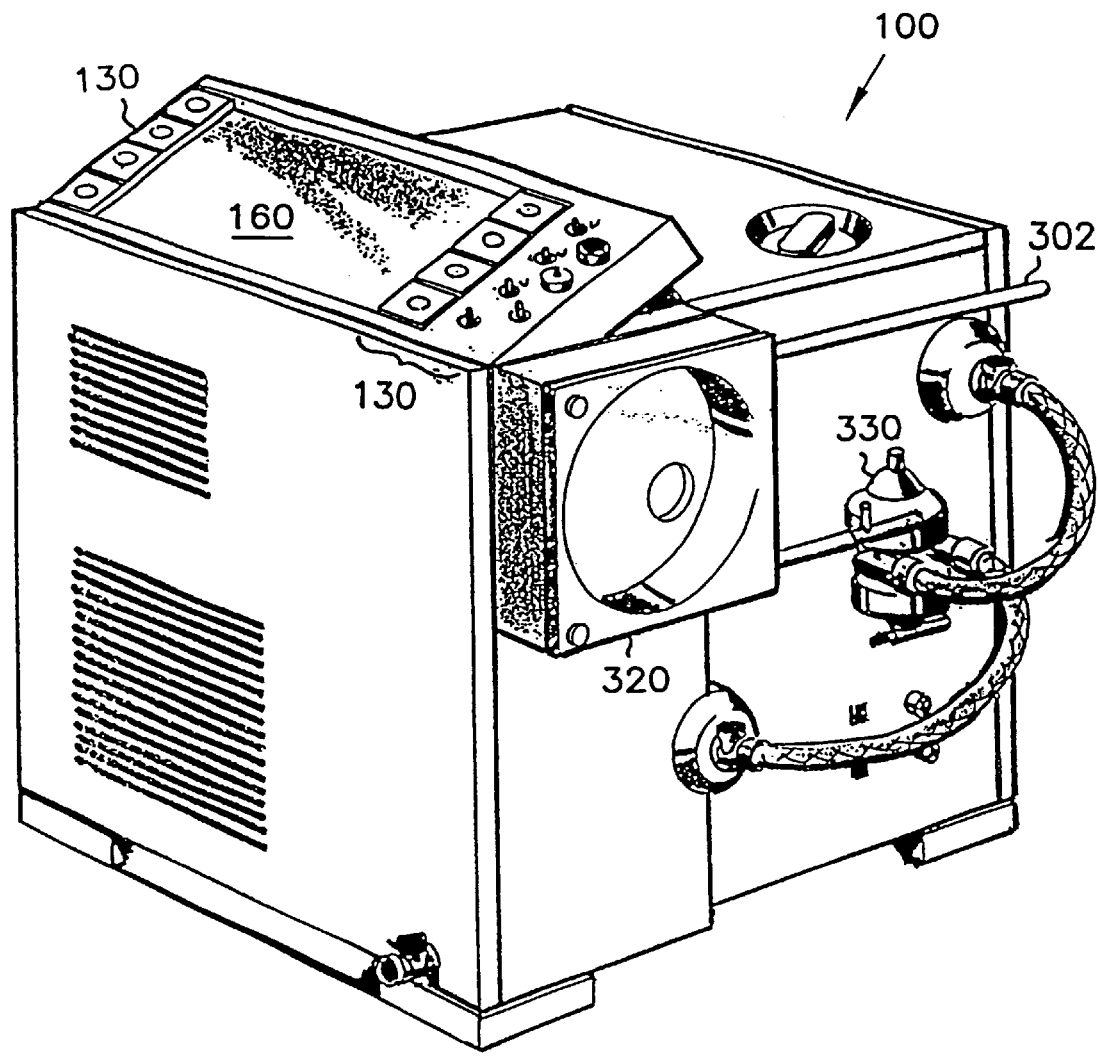
FIG. 21 shows an isometric view of another embodiment of PHTS 100.

FIG. 16B shows a simplified isometric view of a modular vertical-cylinder heat exchanger 1600' according to the present invention which can be used for heat exchanger 330 in PHTS 100. In one embodiment, water-attachment nozzles 1616 are vertically related and pass through the cabinet of PHTS 100 to provide water inlet and outlet points as shown in FIG. 19. In another embodiment, water-attachment nozzles 1616 are horizontally related and connect to external tubing as shown in FIGS. 20 and 21. FIG. 16C shows a front view of a disposable blood-tube assembly 1700' according to the present invention which can be used in modular vertical-cylinder heat exchanger 1600' of FIG. 16B. In this embodiment, tubing 302 passes through the cap 1709, is helically wound around one or more support posts which connect to bottom-end connector 1710', and tubing 302 then passes out through the cap 1709. In one embodiment, the helical-wound portion comprises stainless steel tubing, which is coupled to blood tubing 302. FIG. 16D shows a simplified front view of a reusable vertical-cylinder assembly 1601' which can be used in modular vertical-cylinder heat exchanger 1600' of FIG. 16B.

FIG. 17A shows a front view of a disposable blood-tube assembly 1700 usable with modular clam-shell heat exchanger 1600 of FIG. 16A according to the present invention. One or more end connectors 1710 each provide a connection means to blood tubing 302, and are preferably formed of a rigid, transparent, bio-compatible plastic. In the embodiment shown, a standard ribbed tubing connector is provided to connect blood tubing 302 to each end connector 1710. In another preferred embodiment, blood tubing 302 is glued or welded to end connectors 1710. Manifold 1720 provides a connection means between heat-exchange tubes 1730 (only some of which are schematically shown in FIG. 17A) and end connectors 1710, and is preferably formed of a rigid, transparent, bio-compatible plastic. A plurality of heat-exchange tubes 1730 provide parallel paths having a large aggregate surface area between two end connectors 1710. FIG. 17B shows a cross-section view of the disposable blood-tube assembly 1700 of FIG. 17A across section line 17B. In one embodiment, one or more O-rings 1740 on each end connector 1710 help prevent water from leaking at those positions.

Figure 17C:
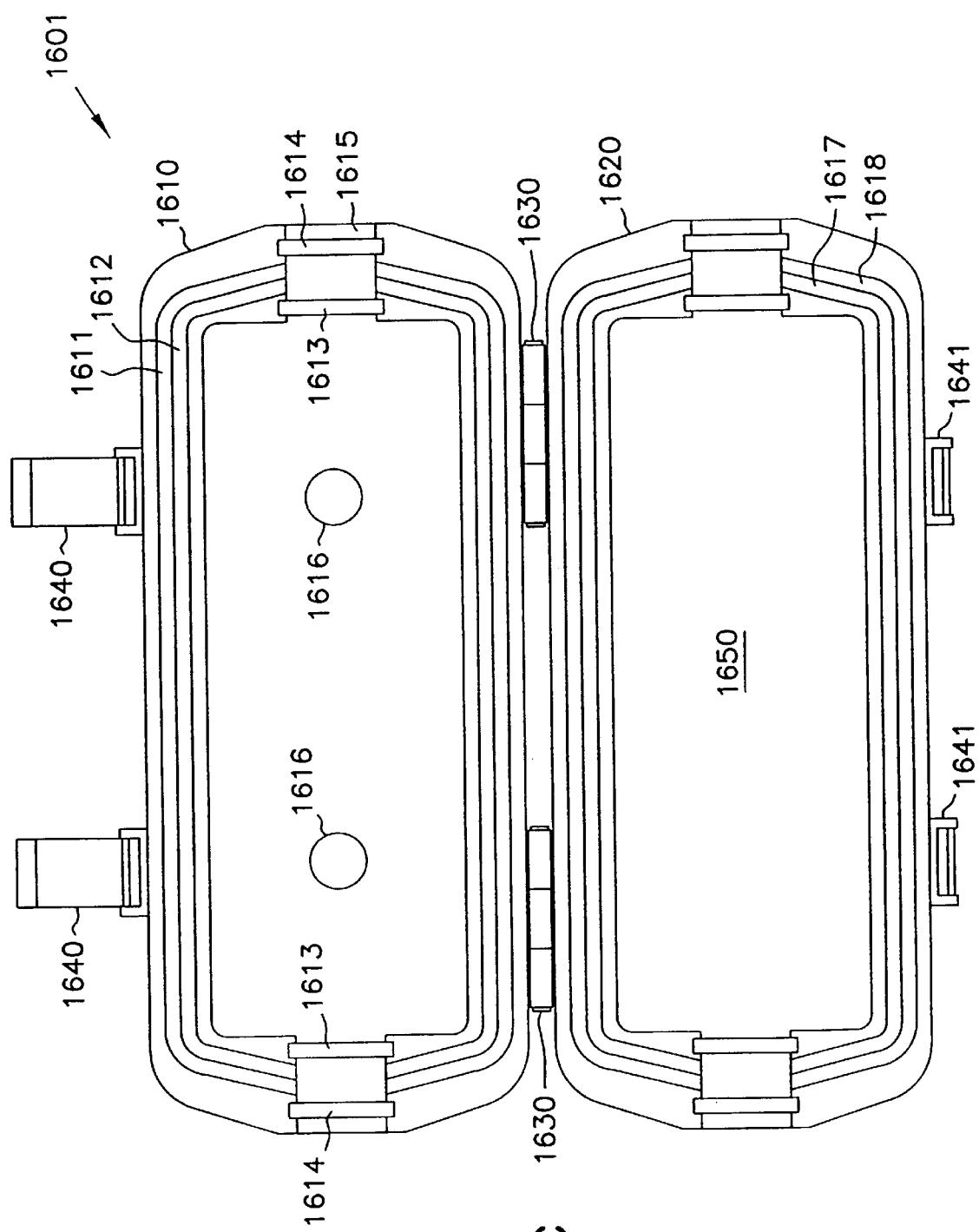
FIG. 17C shows a front, open, view of a reusable clam-shell assembly 1601 usable with modular clam-shell heat exchanger 1600 of FIG. 16A according to the present invention.
Figure 17F:
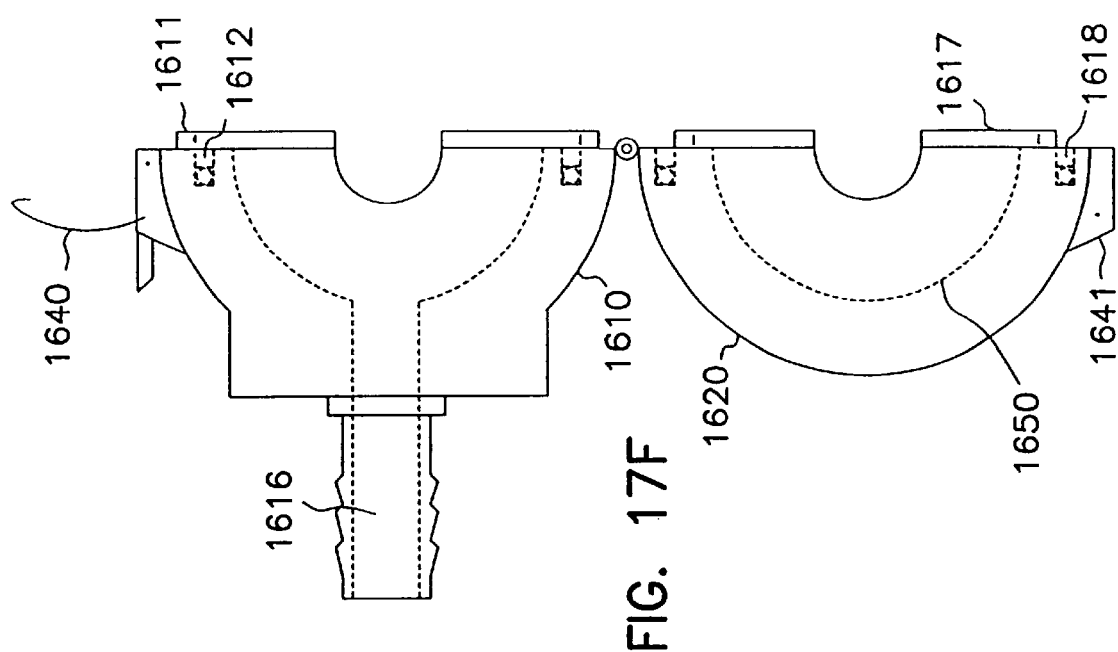
FIG. 17F shows a side, open, view of the reusable clam-shell assembly 1601 of FIG. 17C.
Figure 17D:
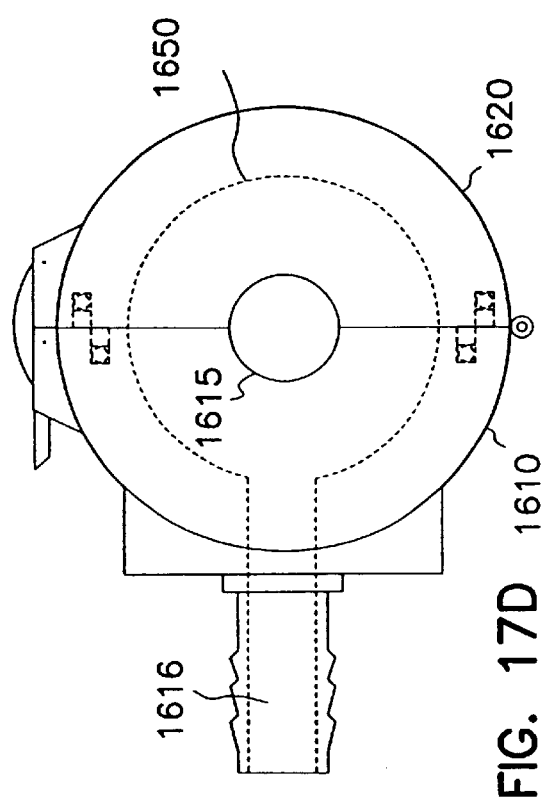
FIG. 17D shows a side, closed, view of the reusable clam-shell assembly 1601 of FIG. 17C.
Figure 17E:
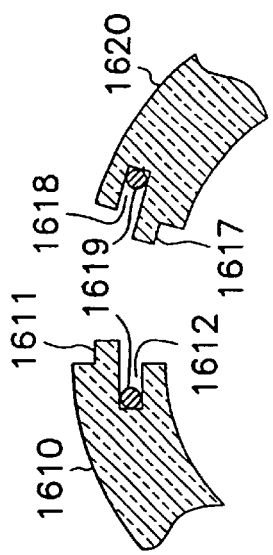
FIG. 17E shows a cutaway detail of one embodiment of the sealing ridges, grooves and gaskets of the edges of reusable clam-shell assembly 1601.

FIG. 17C shows a front, open, view of a reusable clam-shell assembly 1601 usable with modular clam-shell heat exchanger 1600 of FIG. 16A according to the present invention. FIG. 17D shows a side, closed, view of the reusable clam-shell assembly 1601 of FIG. 17C. FIG. 17E shows a cutaway detail of one embodiment of the sealing ridges, grooves, and gaskets of the edges of reusable clam-shell assembly 1601. FIG. 17F shows a side, open, view of the reusable clam-shell assembly 1601 of FIG. 17C. Ridge 1611 mates with groove 1618, in which is preferably a gasketing material 1619; and ridge 1617 mates with groove 1612, in which is also preferably a gasketing material 1619.

On both ends of clam-shell assembly 1601, inner cylindrical grooves 1613 and outer cylindrical grooves 1614 formed into end openings 1615 each mate with corresponding O-rings 1740 (which are rubber O-rings or other gasketing material) of blood-tube assembly 1700 when clam shell 1601 and blood-tube assembly 1700 are assembled. Cavity 1650 provides a path for the heat-exchange water to flow around and/or through blood-tube assembly 1700. Water nozzles 1616 provide water inlet and outlet points. One or more hinges 1630 and one or more latch assemblies 1640–1641 allow the clam shell to be opened or closed and secured. In one embodiment, an electrical signal is generated only when the clam shell is properly closed and secured to a blood-tube assembly 1700. One such embodiment uses a microswitch, which is activated when the clam shell 1601 is fully closed, in series with a connector which passes the signal through both the clam shell 1601 and a particular corresponding blood-tube assembly 1700 for that particular clam shell 1601. For example, various different clam shells 1601 would have electrical connections in different places for different corresponding blood-tube assemblies 1700 in order to detect and prevent operation of PHTS 100 if the wrong blood-tube assembly 1700 (or a counterfeit one) were inserted. Another such embodiment of PHTS 100 uses disposable and/or replaceable parts (such as blood-tube assembly 1700, disposable subsystem 301 as a whole, blood tubing 302, blood preconditioner interface unit 311, blood-pump interface 321, heat-exchanger interface 321, and/or blood postconditioner interface 381) each of which includes an electrical connector (or other signal coupling) to a read-only memory (ROM) which forms a part of the disposable unit and which stores data which is checked by software 500 in order to determine the type and/or authenticity of the disposable and/or replaceable part (in order to prevent use of counterfeit parts and in order to determine and record the type and/or serial number of the disposable part used). Further details of such an authentication apparatus and method are described in U.S. Pat. No. Re. 34,161 to Nakagawa, which is hereby incorporated by reference.

Figure 17G:
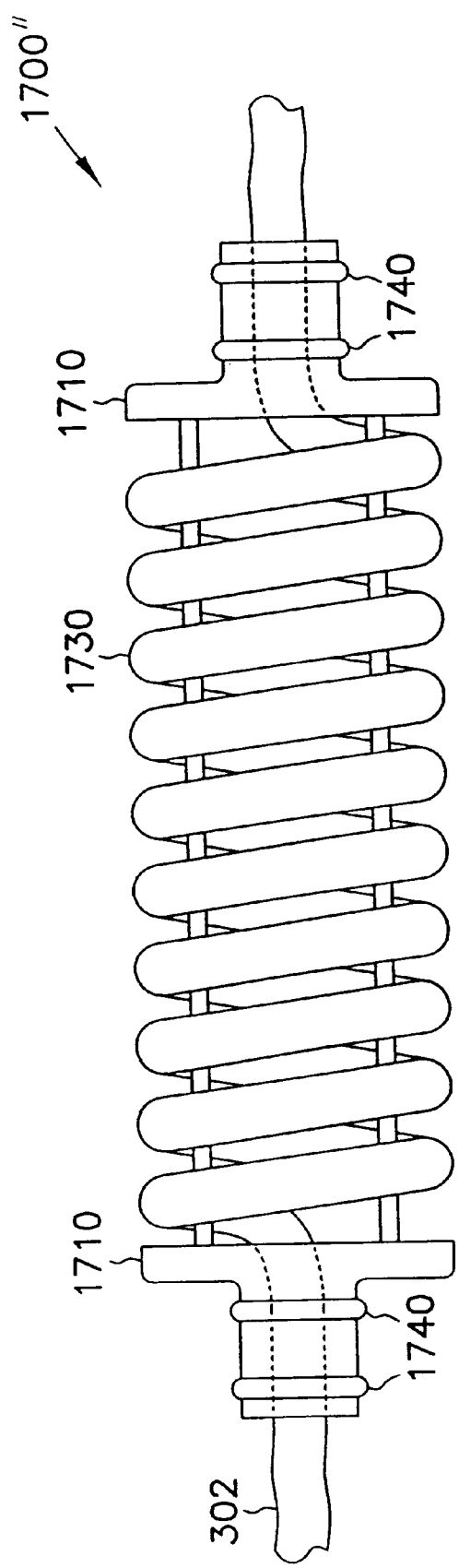
FIG. 17G shows a front view of another embodiment of a disposable blood-tube assembly 1700" usable with modular clam-shell heat exchanger 1600 of FIG. 16A according to the present invention.

FIG. 17G shows a front view of another embodiment of a disposable blood-tube assembly 1700" usable with modular clam-shell heat exchanger 1600 of FIG. 16A according to the present invention, in which blood tubing 302 is helically wound to form a single unified heat-exchange tube 1730. In another such embodiment, a stainless-steel tube is helically wound to form a single heat-exchange tube 1730, and is glued or otherwise sealed to blood tubing 302.

Figure 18:
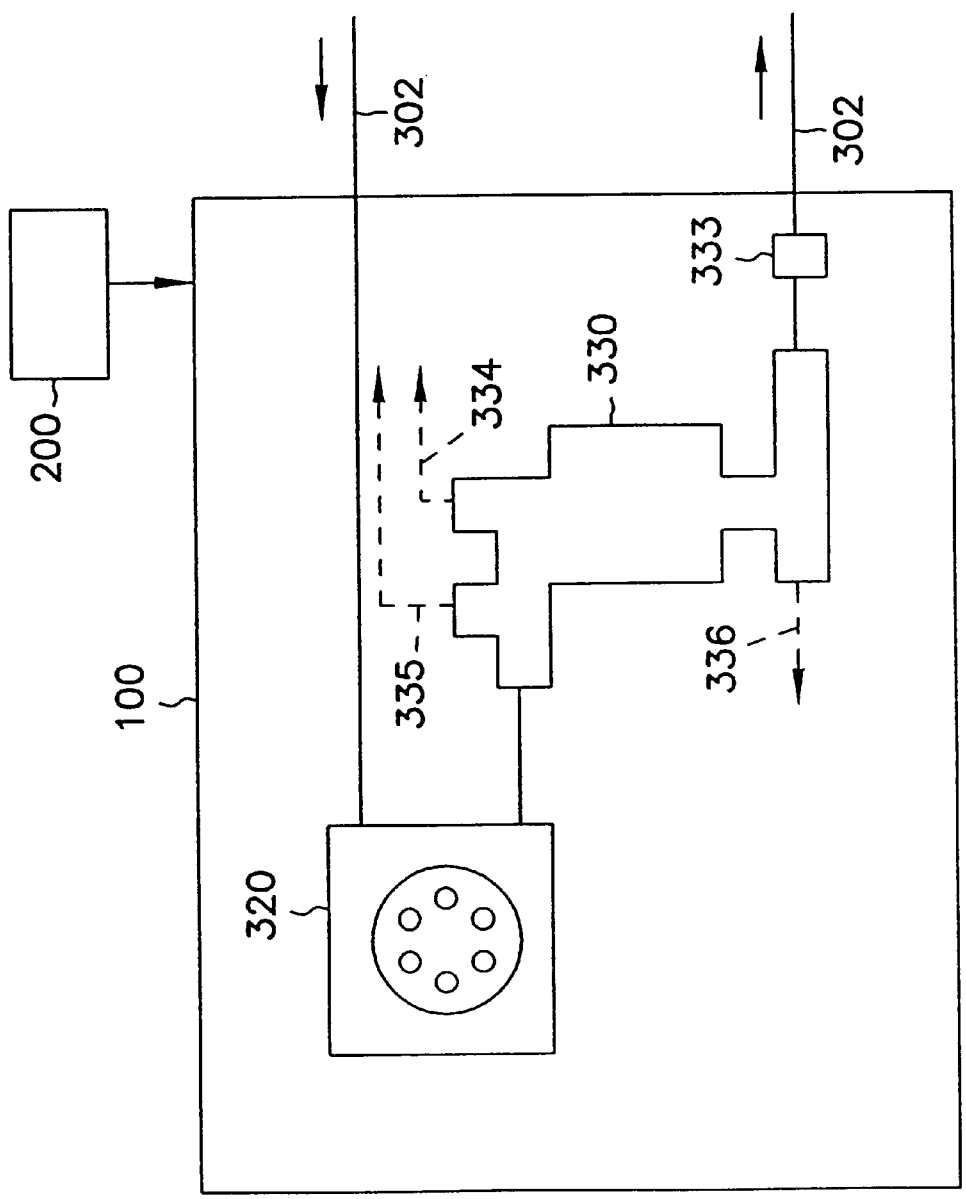
FIG. 18 shows a schematic of some connections of one embodiment of PHTS 100 having a simplified structure including monitoring system 200, blood pump 320, heat exchanger 330, and bubble detector 333.

FIG. 18 shows a schematic of some connections of one embodiment of PHTS 100 having a simplified structure including monitoring system 200, blood pump 320, heat exchanger 330, and bubble detector 333, blood-inlet-temperature detector 335, blood-outlet-temperature detector 336, and blood-pressure detector 334.

FIG. 19 shows an isometric view of a cover structure for one embodiment of PHTS 100.

FIG. 20 shows an isometric view of one embodiment of PHTS 100 having a front-mounted beveled display for mounting display screen 161 using bezel buttons and knobbed switches and dials for input device 130. Blood pump 320 is mounted to the side of the cabinet, with blood tubing 302 connecting it to heat exchanger 330, which has externally connected water tubing running water to and from the cabinet. A water drain is shown at the bottom of the front of the cabinet, a water-fill port on the top, and a gravity-fill path between with water pump 370 at the lowest point of the water circuit.

FIG. 21 shows an isometric view of another embodiment of PHTS 100, similar to FIG. 20, except that the display screen and input devices 130 are mounted at an angle on the top of the cabinet.

Figure 22:
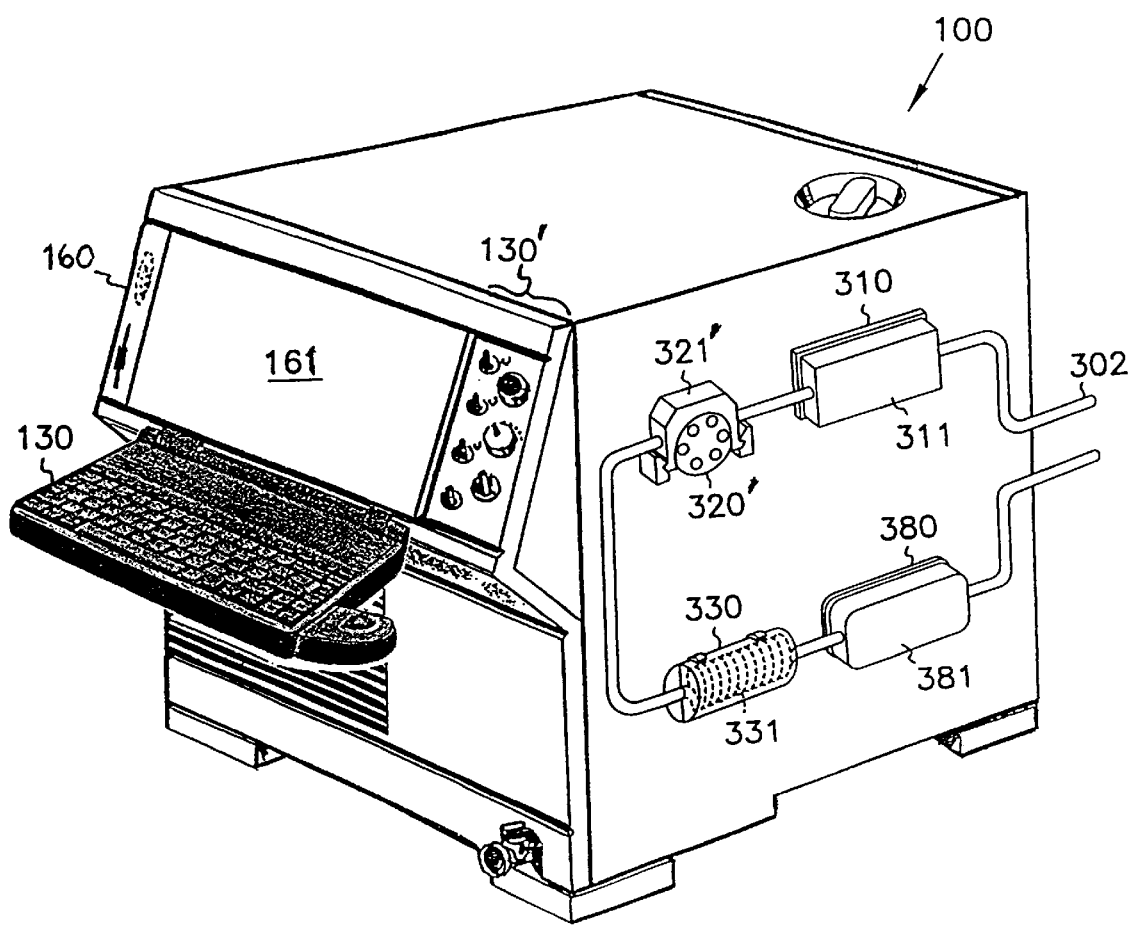
FIG. 22 shows an isometric view of yet another embodiment of PHTS 100.

FIG. 22 shows an isometric view of yet another embodiment of PHTS 100, showing a personal-computer-type keyboard input device 130, some manual control switches input device 130', an output device 160 including a display screen 161, a disposable subsystem 301 (including blood tubing 302, blood preconditioner interface unit 311, blood-pump 320', blood-pump interface 321', heat-exchanger 330 and interface 331, blood postconditioner interface 381, and a further length of blood tubing 302 for returning the blood to the patient) coupled to system interface 390 located on the side of the cabinet of PHTS 100.

The useful features of PHTS 100 include the integrated, self-contained construction of the mechanical (e.g., in one embodiment, the integrated packaging of disposable subsystem 301 its interface to the integrated system interface 390) and electrical (e.g., computer system 110, monitoring system 200, and the electrical sensor and control portions of ECC 300) systems, the disposable circuit 301, and the integrated checklist 504 and system feedback controls, e.g., water temperature control 508, blood temperature control 512, and body temperature control 516 for water, blood, and body temperatures, respectively. Many of the components of PHTS 100 can be based on existing heart-lung machine technology. In one embodiment, PHTS 100 is alternating current (AC) 110 volt line powered, and includes an internationally qualified power supply. PHTS 100 has a first mode of operation which is computer-controlled with some amount of manual input from the user in order to verify certain conditions which cannot be electrically verified by the computer, and a second mode of operation which is computer-monitored with manual overrides on the control nodes. In one embodiment, PHTS 100 includes start-up tests 502 which verify correct function of the major subsystems before any operation of the device is attempted, plus self-diagnostics 506 which continually test for the continuing correct function of the subsystems and parts of PHTS 100 during operation. In one embodiment, PHTS 100 includes integrated pressure-monitoring sensors for measuring pressure of blood in blood tubing 302 and of the water in the water-conditioning subsystem 340. In one embodiment, PHTS 100 also includes automated data logging for therapy sessions, which records all checklist responses, all monitored parameters during the operation, and all control signals, along with timestamps, onto a storage medium. In one embodiment, the storage medium is a paper printout. In another embodiment, the storage medium is a removable magnetic diskette.

In one embodiment, PHTS 100 comprises a blood pump 320 for controlled-rate perfusate pumping (one embodiment uses a DeBakey-type double-roller pump for pump 320); a heat exchanger 330 having water connections 1616; sensors 345 and 346 for monitoring and controlling of the water temperature for the heat exchanger 330; sensors 335 and 336 for monitoring and controlling of the perfusate temperature; up to ten or more sensors 201–203 for monitoring and controlling of the subject's 99 body-core temperature and controlling temperatures and temperature differentials in various parts of the body of patient 99; sensors 333 (one embodiment uses ultrasonic sensors known to the art) for monitoring and acting on bubbles in the perfusate; one or more input device 130 to provide an operator ability to set control points; one or more input device 130 also used to provide an operator open loop control via manual switches; one or more display device 161 for temperature and pressure display; testing sensors and software for power up tests 502 and continuous real time fault monitoring 506 ; an interactive checklist 504 to elicit and receive operator responses to safety and setup checklists; visible warning and alarm indications (e.g., display features 640, 1114, 1124, etc.) on display 161 and audible alarm indications on audio output 162; a controller 111 which provides a system safety fallback to a passive state on a detected component failure; system safety designed into all aspects of the design and implementation of the physical system, within accepted perfusion practices; and removable storage means 162 for parameter data storage and transfer to removable media for post-procedure processing and display.

Several factors, based upon human and animal investigations, have shown that the following seem to be critical factors in the survival of a subject treated with the hyperthermic processes:

A. Maintenance of an adequate and stringently controlled water-to-blood temperature gradient. The rate of heat transfer to the perfusate and the efficiencies involved to effect heat input must be rigorously controlled.

B. Tracking of the various blood and body temperature levels and rates of change to assure uniform heating has been shown to affect the efficacy of the therapy.

C. Measuring the differential left and right tympanic temperatures. Anecdotal evidence suggests that a large temperature differential may be the cause of a neurological deficit (which resolved slowly over time) that occurred to a small subset of test subjects. It also appears to have contributed to strokes and seizures that occurred to other test subjects.

D. Controlled cooling is just as important as controlled heating. Cooling too rapidly appears to be able to cause the same temperature differentials, and potential problems, as heating too rapidly. There is also anecdotal evidence to suggest that there is a possibility that some subjects can reach certain elevated temperature plateaus. Controlled extracorporeal cooling is required to trigger the body's own intrinsic cooling mechanism into operation if one of these plateaus (hypothalamic change of set point) is reached.

In one embodiment, the disposable subsystem 301 interfaces with one side of the chassis of mechanical subsystem 600 as shown in FIG. 20. See FIG. 2C which illustrates a schematic of such a system interface to disposable subsystem 301 of FIG. 2B. In one embodiment, disposable subsystem 301 is pre-assembled and pre-sterilized as an entire subsystem or cartridge which is "plugged" (all electrical and/or mechanical connections made with few, if any, tools or manual adjustments) into the permanent reusable portion, i.e., system interface 390 of ECC 300.

The following system components are under computer control:

A. water pump 370 off/on
B. water cooling 360 fan off/on
C. water heater 350 off/on
D. blood pump 320 off/rate-of-flow One embodiment of blood pump 320 utilizes a reusable roller portion of blood pump 320 to interface with a disposable tubing/tubing interface device 321 through which the blood moves (positive displacement or peristaltic style), and a means (i.e., sensors 325 and 326 along with software programmed feedback control from drivers 124 to the motor of blood pump 320 in order to adjust the measured parameters to their desired levels) for controlling the flow rate, output pressure, or throughput of the pump. The design of this pump 320 is inherently such that the correct setup and assembly of the interface tubing provides a conversion factor between pump speed and calculate/estimated blood-flow rate that closely reflects the actual blood flow.

The mechanical subsystem 600 includes the heating/cooling water conditioning subsystem 340 which contains a water pump 370 and temperature control assembly 350 and 360. In one embodiment, this assembly has the following major components in the following water-flow order:

1. water pump 370 (one embodiment places water pump 370 at or near the lowest point in the water circuit in order to facilitate priming the circuit with water, and pulling water out of the heat exchanger 330 in order to minimize water pressure within the heat exchanger 330)
2. a water cooler 360 for cooling the water (one embodiment uses a radiator, such as an automobile transmission fluid cooler unit, and a fan to blow ambient room air across the radiator; one such embodiment also includes a float-type air purge valve such as are used in home water-heating systems in order to prime the system/fill it with water; another embodiment uses a Peltier-effect thermoelectric module to cool the water; yet another embodiment uses a refrigerator-type cooler to cool the water)
3. 'T'-connector 344 to reservoir 343, with the water passing substantially horizontally through the tangential section, and the reservoir connected above the substantially vertical perpendicular section, as shown in FIG. 2A, in order to minimize heat transfer from the water circuit into the water in the heat exchanger and to transfer air bubbles from the water circuit out into the reservoir 343, and to supply water to the water circuit)
4. water heater 350 for heating the water
5. temperature probe 345
6. blood/water heat exchanger 330 (the blood-contact portion 331 is disposable)
7. temperature probe 346, and back to water pump 370.

In another embodiment, air is used as the heat-exchange medium in conditioning subsystem 340, with the following major components:

1. air fan 370
2. air cooler 360 (one embodiment uses a Peltier-effect thermo-electric module to cool the water; another embodiment uses a refrigerator-type cooler)
4. air heater 350
5. temperature probe 345
6. blood/air heat exchanger 330 (the blood-contact portion 331 is disposable)
7. temperature probe 346, and then vented out of the system.

The heating and cooling subsystem 340 comprises an interface between disposable portion 331 and blood heat exchanger 330 that effects the controlled change in the temperature of the blood passing through disposable portion 331. This in turn affects the temperature of various regions of the body of patient 99. PHTS 100 thus incorporates a means to heat and cool the blood efficiently and in a closely and automatically controlled fashion.

Research has shown that a water exchange system with a minimum of approximately 500 Watts of heat, with a minimum water flow of approximately 10 liters per minute is sufficient for adding the required calories to the blood at a minimal blood-flow rate, while still causing the required change in the blood temperature necessary for overcoming native thermal losses. This ultimately results in the desired change in the body temperature of patient 99.

Computer system 110 comprises one or more computing elements with sufficient processing power, memory, and other resources to perform the following control functions.

1. Monitoring and Control
   a) One primary function of computer system 110 is to acquire the necessary sensor data, interpolate and extrapolate this information, and execute the necessary control functions required to cause PHTS 100 to perform its specified therapy.
   b) The temperature controller is a programmed computer feedback system which measures the temperature of the various critical sites. The controller integrates and controls the rates of change in and between the various monitoring sites.
   c) The pressure monitoring provides a safety feature to detect a liminal occlusion.
   d) Monitoring is performed on a continuous basis. Where appropriate, monitored values have a warning threshold and an alarm threshold. The monitor may either issue a warning or issue an alarm and limit the device output as appropriate for the particular sensor.
2. Data Display and Removable Media Storage
   a) The input/display module 560 has primary functions including 1) user input, 2) continuous, real time data display (in one embodiment, simultaneous graphical displays are generated to display screen 161 of a plurality of graphs of temperature versus time, comparing predetermined desired temperature profiles and measured actual temperature profiles; one such embodiment also includes graphical displays of cardiac, pulmonary, and/or blood-pressure signals), and 3) optional real time data storage. This module is responsible for generating appropriate display information for the operator, acquiring and interpreting operator input, and logging appropriate information for further analysis. The stored data can be transferred to a removable media for postoperative analysis.

All aspects of the design and implement must be performed such that: No single failure can prevent detection of a failure, or prevent PHTS 100 from entering a fail safe state. See Table 1, Alarm and Warning Conditions for a list of monitored parameters in one embodiment.

Because blood temperature changes can cause outgassing, a standard extracorporeal bubble detector is to be used in conjunction with a bubble trap. In one embodiment, the bubble trap is an integral part of the heat exchanger, and is located downstream of the bubble trap within heat exchanger 330. This mechanism provides a fail-safe way to stop the blood pump 320 in the event that a bubble is present in the re-entry line of the blood path. Note: Bubbles are an expected part of any perfusion technique. However, the bubble trap and bubble detector 333 serve to reduce the risk of infusing a bubble into the subject (patient 99).

In one embodiment, the temperature monitor functions 507, 510, and 514 limit the system outputs, and controls are activated if temperatures and temperature rates of change exceed predetermined limits. These limits are set to prevent potential thermal injury to the blood, body, and brain of the patient.

In one embodiment, the pressure monitor function stops the blood pump 320 if the blood pump pressure exceeds a predetermined level. This limit is set to prevent potential injury to patient 99.

The computer system 110 is to be programmed to control the rate limits, process limits, rates of change, etc., for PHTS 100. The computer system 110 employs power up and continuous monitoring that PHTS 100 is functioning. Upon failure, the PHTS 100 is driven to a fail-passive state.

In one embodiment, PHTS 100 is designed and built to provide a specified system failure rate of less than 1 failed device for every 20,000 hours of field use. This corresponds to approximately 5000 treatments at a maximum of 4 hours use per treatment.

In one embodiment, PHTS 100 is designed to facilitate field maintenance by trained personnel. In this embodiment, a periodic preventative-maintenance (PM) regimen is established and major repairs are accomplished under a depot system utilizing field-replaceable-module concepts.

In one embodiment, display 161 is a text-based monochrome LCD-VGA display screen. In one such embodiment, display 161 provides a visual digital indication of the value of each of the temperature probes. In one such embodiment, display 161 is updated at rate of at least once every two seconds (½ Hz.).

In one such embodiment, display 161 provides a digital display which indicates the temperature in tenths of a degree Celsius (°C.) as three digits (tens, ones, decimal point, and tenths of a degree). In one such embodiment, display 161 is designed to be readable, by a person with 20/30 vision, at a distance of 1.2 meters (4 ft) from display 161.

In one such embodiment, display 161 also provides a visual digital indication of the value of each of the pressure sensors, updated at a minimum rate of ½ Hz, and indicates the pressure value in units of millimeters of mercury (millimeters Hg) as three digits with leading zeros suppressed. In one such embodiment, the pressure displayed on display 161 is designed to be readable, by a person with 20/30 vision, at a distance of 1.2 meters (4 ft) from display 161.

In one such embodiment, display 161 also provides a visual indication of the state of the various safety sensors of PHTS 100. See Table 1, Alarm and Warning Conditions.

In one such embodiment, display 161 also provides an indicator that lights in the event that any system safety parameter is exceeded. This indicator should be visible at a distance of 1.8 meters (6 feet) and should be red to indicate danger. In one such embodiment, display 161 should update all displayed data at least once every two seconds. In one such embodiment, display 161 also displays the version number of the software 500. In one such embodiment, display 161 displays blood-flow rate based on the average rate of the immediately preceding 5 seconds. The accuracy of this indicated blood-flow rate is within 10% of the actual flow rate. In one such embodiment, display 161 also displays blood temperature rate, which is recalculated based on the history of the immediately preceding 60 seconds.

TABLE 1

Alarm and Warning Conditions

| Parameter | Alarm Threshold | Warning Threshold |
| --- | --- | --- |
| 1. higher of the two tympanic temps | 43° C. | 42° C. |
| 2. delta tympanic temp | 1.0° C. | 0.8° C. |
| 3. body-core average temperature | 43° C. | 42° C. |
| 4. temperature of blood out of HE | 46° C. | 45° C. |
| 5. Pressure of blood out of the blood pump | 100 mm Hg | 90 mm Hg |
| 6. bubbles detected | yes | yes |
| 7. water reservoir low | yes | yes |
| 8. tympanic average temp rate | 1.4° C./min | 0.3° C./min |
| 9. tympanic average temp, core average temp difference | 4.0° C. | 3.0° C. |
| 10. high core temp, low core temp difference | 4.0° C. | 3.0° C. |
| 11. body-core average temp rate | 0.4° C./min | 0.3° C./min |

TABLE 1-continued

Alarm and Warning Conditions

| Parameter | Alarm Threshold | Warning Threshold |
|---|---|---|
| 12. blood-flow acceleration | 0.25 l/min/min | 0.23 l/min/min |
| 13. blood-flow rate | | 1.25 l/min |
| 14. time body-core temp elevated above normal (or time subject blood pumped) | | 3:00 |
| 15. time body-core temp above target temp | | 2:00 |
| 16. core thermistor failed | yes | yes |
| 17. blood out of HE temp rate | 4.0° C./min | |
| 18. difference between blood out of HE temp, body-core average temp difference | 4.0° C. | |
| 19. difference between water into HE temp, blood into HE temp | | 8.0° C. |

In one embodiment, PHTS 100 has a water fill port that provides the capability to fill water-conditioning subsystem 340 with water without spilling water.

In one embodiment, water-conditioning system 340 provides an indication to control computer 111 of nominal water-full range. In one embodiment, water-conditioning system 340 provides a manually operated water-drain valve that is capable of draining PHTS 100 of water. One purpose is to empty enough water such that freezing PHTS 100 does not cause damage due to ice expansion. In one embodiment, water-conditioning system 340 provides a low-level sensor to indicate to control computer 111 that the water level is too low, which preferably triggers when the water is within 10% of exposing the heater element 350. When the low level sensor is triggered, it preferably causes PHTS 100 to stop the water pump 370, water heater 350, and water cooling fan of water cooler 360, in order to prevent damage to the heating elements.

In one embodiment, water-conditioning system 340 provides a water flow detector sensor in detector 345 and/or 346 to allow early determination of system failure. This sensor is a secondary sensor since ultimate operational status of the device is primarily determined by temperature changes throughout the system. This sensor is primarily intended for use during the start-up safety check and self-test process. Failure to detect water flow at this time preferably prevents the initiation of a therapy session. Failure to detect circulation during a session preferably generates a warning alarm.

In one embodiment, water-conditioning system 340 provides quick release ports for the water interfaces to the heat exchanger: water from the chassis to the heat exchanger and water from the heat exchanger to the chassis.

In one embodiment, PHTS 100 has chassis cooling air entry and exit vents and water cooling air entry and exit vents which are located and oriented such that air is not blown in the direction of the sterile field.

In one embodiment, PHTS 100 includes a blood pump 320 capable of providing up to not less than 1.25 liters/minute of blood flow. The blood pump 320 supports flexible tubing having ¼" inside diameter.

In one embodiment, PHTS 100 includes a bubble detector 333 in the perfusion circuit near the exit point of the bubble trap incorporated in heat exchanger 330. This bubble detector 333 is a secondary fault detector since a bubble trap is in-line upstream in the shunt circuit. This bubble detector 333 is capable of detecting any bubble larger than the inside diameter of the perfusion circuit tubing at a flow rate of 1.25 liters/minute. This bubble detector 333 is designed such that false positive bubble indication occurs no more frequently than 1 false positive every 5,000 operational hours. In one embodiment, PHTS 100 is designed such that the detection of a bubble preferably stops the blood pump immediately and sounds the audible alarm. The bubble detector 333 preferably accepts a ¼" inside diameter plastic tube.

In one embodiment, PHTS 100 includes a heat exchanger holder which accommodates the Electromedics model D1079E heat exchanger. (This heat exchanger is or will be a commercially available component. An appropriate holder/clamp is used.)

In one embodiment, PHTS 100 includes two pressure sensor inputs. One of these sensors is uncommitted and the other is used to monitor the blood pump output. The uncommitted pressure monitor is accurate to within ±10% for the entire range from 0 mm to 300 mm Hg. The uncommitted pressure monitor is able to withstand the range from −50 mm to +450 mm Hg with no damage or loss of accuracy in its operating range. A failed sensor may cause the treatment to be prematurely terminated. The sensor failure rate should be less than 1 for every 10,000 hours of use.

In one embodiment, PHTS 100 uses a minimum of six (6) temperature sensors for the purpose of monitoring subject body temperatures during the course of a therapy session. Two of the sensors (e.g., 201 and 202) are placed such that they can measure the temperature difference across the left and right tympanic monitoring sites. These probes are referred to as right tympanic and left tympanic. The remaining body temperature probes are placed at strategic locations throughout the body mass and are used to determine body-core temperature. Two temperature sensors are required to monitor the blood temperature. One (335) is located to provide the temperature at the heat exchanger 330 inflow, while the other (336) is located at the heat exchanger 330 outflow. Two final temperature sensors (345 and 346) are located to monitor the water system temperatures. One sensor is located in the water path to the heat exchanger 330 to monitor the water temperature of the heat source for the heat exchanger. The other measures the water temperature in the water path out of the heat exchanger. In one embodiment, the water temperature sensors are not disposable (i.e., are not intended to be replaced by the operator). All other temperatures sensors are disposable and are intended to be used for one therapy session only. It is highly desirable that the same technology be used for sensing all points.

In one embodiment, PHTS 100 provides twelve temperature probe interfaces. Table 2 below shows a temperature probe list for one embodiment of the present invention. Given probes that are accurate to within ±0.1° C., the system temperature measuring accuracy preferably is ±0.3° C. from 35° C. through 65° C.

TABLE 2

Temperature Probe List

| Temperature Probe Location | Disposable | Operator Accessible |
|---|---|---|
| 1. left tympanic | | |
| 2. right tympanic | | |
| 3. esophageal, body | | |
| 4. indwelling, body | | |
| 5. rectal, body | | |
| 6. rectal/bladder, body | | |
| 7. uncommitted | | |
| 8. uncommitted | | |
| 9. blood into the heat exchanger | | |
| 10. blood out of the heat exchanger | | |
| 11. water into the heat exchanger | | |
| 12. water out of the heat exchanger | | |

In one embodiment, PHTS 100 does not provide electrocardiogram (ECG) interface or display capabilities. In another embodiment, ECG display is provided.

In one embodiment, PHTS 100 provides a mechanism for logging to output device 163, such as magnetic diskette, the temperature and pressure values acquired and operator control selections during the course of a therapy session.

1. Sampled data values will be logged at a sampling rate of 1 Hz.
2. All operator control selections preferably are logged.
3. Upon operator selection, the log file preferably is copied to a floppy diskette.
4. The logged data preferably is written to the floppy
5. Each data log file preferably includes the following:
    a) The date and time that the file was opened.
    b) The version of the application software.
    c) Indication as to whether each checklist was completed or bypassed.
    d) Thermal dose to the subject. Defined as the area under the subject temperature versus time curve in units of °C.-minutes.
  See FIG. 5B showing thermal dose.
    e) Total time at or above the target body-core average temperature.
    f) Total profusion time. Defined as the time that the blood pump was on while the system was connected to the subject.
    g) Maximum tympanic temperature during the procedure.
    h) Maximum body-core average temperature during the procedure.
6. Temperature and pressure data values preferably are stored in binary format.
7. Logged information that is not data values preferably are stored in ASCII format.

In one embodiment, PHTS 100 generates a tone or audible alarm on speaker 162 that sounds in the event that any system safety parameter is exceeded. This indicator preferably is clearly audible in an operating room environment from a distance of 8 meters (26 feet).

In one embodiment, PHTS 100 provides an output via an RS232 jack that provides temperature, pressure, and system state at the minimum rate of once every 2 seconds. This information is provided for an optional external data display placed at a location remote from PHTS 100.

In one embodiment, PHTS 100 is designed with a system power requirement intended to accommodate international power standards with, at most, the use of an external transformer.

1. The system preferably performs its required capability or functionality with an input power of 100 to 130 VAC, 50 to 60 Hz.
2. Under power conditions that would result in the inability of the system to perform its required functions, the system preferably is driven to a fail-passive state.

In one embodiment, PHTS 100 provides closed loop control of the water, blood, and body temperatures. See FIG. 5A showing the control block diagram.

1. The blood pump rate preferably is increased at a rate not exceeding the blood pump rate warning threshold. See Table 1, Alarm and Warning Conditions.
2. The blood pump rate preferably is set by operator input only. That is to say, the system will not change the blood pump rate automatically. However, the system will ramp the blood pump rate to the rate selected by the operator at an acceleration that does not exceed the warning threshold.
3. The blood-flow rate preferably is adjustable from 0 to 1.25 liters/minute in steps of 10 milliliters/minute with an accuracy of ±milliliters/minute.
4. PHTS 100 preferably automatically starts and stops the water pump to perform its functions.
5. PHTS 100 preferably automatically starts and stops the water heater 350 and water cooler 360 to perform its functions.
6. PHTS 100 preferably only uses the heater 350 while heating and maintaining the temperature of the subject (i.e. will not use the water cooling fan of water cooler 360).
7. PHTS 100 preferably only use the water cooling fan of water cooler 360 while cooling the subject (i.e. will not use the heater 350).
8. PHTS 100 preferably controls the water temperature so that water-temperature-related warnings are not violated.
9. PHTS 100 preferably controls the blood temperature so that blood-temperature warnings are not violated.
10. PHTS 100 preferably controls-the body temperatures so that body and tympanic temperature warnings are not violated.
11. PHTS 100 preferably uses the water temperature to control the blood temperature, the blood temperature to control the body temperature. Within the warning threshold limits, PHTS 100 preferably attempts to drive the subject body temperature to the target temperature for the therapy duration selected.

Manual Control

In one embodiment, PHTS 100 provides the operator, via the manual control panel, the ability to manually control the water pump, water heater, water cooling fan, and the blood pump rate. Even in manual mode, PHTS 100 monitoring will disable certain system control outputs upon warning and/or alarm activation.

1. PHTS 100 preferably reacts to operator selection on the manual front panel within 0.25 seconds.
2. Upon activation of a switch on the manual panel, PHTS 100 preferably stops automatic temperature control of the water.
3. While the water pump is turned off manually, PHTS 100 preferably turns the water heater and water cooling fan off.
4. Upon the operator selecting manual control of the blood pump speed, PHTS 100 preferably sets the automatic speed to zero. This is to prevent the blood pump from starting automatically when the operator selects automatic control after selecting manual control.
5. The manual control panel blood pump rate switch preferably is capable of commanding a blood pump rate from 0 to 1.25 l/min.

Operator Input

In one embodiment, PHTS 100 provides an operator an input capability via the display and bezel button switches listed in Table 3, Operator Input.

TABLE 3

Operator Input

| Operator Input Description | Range | Interval |
|---|---|---|
| 1. checklist items | yes/no | |
| 2. blood pump rate | 0 to 1.25 l/min | 0.10 l/min. |
| 3. target body-core average temperature | 37 to 43° C. | 1.0° C. |
| 4. time at target temperature | 0:10 to 3:00 | 10 minutes |
| 5. log file annotations | See Table 4 | |

TABLE 4

List of Log File Annotations

Log File Annotation Text

1. Temperature probe change
2. Beta blocker administered

Monitoring

In one embodiment, PHTS 100 is designed such that, upon the occurrence of a warning condition, the display is changed, if necessary, to provide information as to the precise nature of the warning.

In one embodiment, PHTS 100 is designed such that upon the occurrence of an alarm condition, the display is changed delineating the alarm.

In one embodiment, PHTS 100 is designed such that the bezel button and screen interaction is implemented in order that an explicit alarm acknowledge is required before other information is displayed or operator selections allowed.

In one embodiment, PHTS 100 is designed such that to avoid nuisance alarm and warning display changes, transitioning in and out of an alarm or warning condition within a fixed time after that alarm or warning has been delineated, does not cause a screen change.

In one embodiment, PHTS 100 is designed such that PHTS 100 requires that at least 3 of the 4 body temperature probes be connected, both tympanic temperature probes, both blood temperature probes, and both water temperature probes for operation.

In one embodiment, PHTS 100 is designed such that PHTS 100 monitors for and declares warning and alarm conditions as defined in Table 1, Alarm and Warning Conditions.

In one embodiment, PHTS 100 is designed such that PHTS 100 provides the operator the capability to remove one of the four body temperature probes from monitoring and use during calculations.

Operational Phases

In one embodiment, PHTS 100 supports the following operational phases:

Power Up, Self Test phase, controlled by power-on self-test module 502, which:

1. In one embodiment, upon power up, PHTS 100:
   a) checks if the previous hyperthermia session had completed.
   b) if the previous session had been completed, initiates power up self test.
   c) if the previous session had not been completed and was started less than four hours ago, PHTS 100 bypasses the power up self test and enters the setup phase.
2. In one embodiment, PHTS 100 tests all inputs and outputs that do not require operator intervention.
3. In one embodiment, if the power up self test completes without any errors detected, PHTS 100 enters the setup phase.

The setup phase, controlled by operator start-procedure checklist module 504, occurs when the operator is preparing the device for connection to the subject. It provides part of the initial check-off required prior to commencement of a therapy session:

1. PHTS 100 preferably lists each step of the set up check list and display operator selections.
2. PHTS 100 preferably allow the operator to bypass any age of the checklist.
3. PHTS 100 preferably preheat the water to the water to blood warning limit.
4. The fluid that is used to prime the blood lines preferably is preheated to the blood to body warning limit.
5. PHTS 100 preferably allow and facilitate the priming of disposable subsystems as necessary for proper operation.
6. PHTS 100 preferably verifies water heating and cooling system functionality.
7. PHTS 100 preferably verifies blood pump functionality.
8. PHTS 100 preferably verifies the functionality of safety sensors.
9. PHTS 100 preferably verifies the blood pump tachometer calibration.

The subject-body-heating phase, controlled by body heating module 520, occurs when the operator completes the set up phase and initiates a therapy session. Heat is applied to the water subsystem insuring that temperature restrictions outlined above are enforced. The rate of rise for the body-core temperature is one of the controlling parameters for this process. Once the body temperature has been held at the target temperature for the appropriate period of time, the controlled cooling cycle is started. The physician will be the final arbiter as to whether or not a particular therapy session has been properly completed:

1. Upon completion of the set up check list, PHTS 100 preferably enters the subject body heating phase.
2. PHTS 100 preferably drives the subject body-core average temperature to the target temperature while staying within the limits of Table 1, Alarm and Warning Conditions.

The subject-body-temperature-maintenance phase, controlled by maintaining-body-temperature-at-target module 522, occurs when the proper target body-core temperature has been reached. PHTS 100 simply maintains the target body-core temperature and monitors the temperature differences between various probes to insure that no limits are exceeded:

1. Upon the average body-core temperature reaching the target temperature, PHTS 100 preferably enters the subject body temperature maintenance phase.
2. PHTS 100 preferably maintains the subject body temperature to within 0.5° C. of the target temperature for the therapy duration while staying within the limits of Table 1, Alarm and Warning Conditions.

The subject-body-cooling phase, controlled by body cooling module 524, occurs when the required period of time for the therapy has been reached. In one embodiment, ambient air is used to cool the water while insuring that temperature control restrictions are enforced. The rate of fall for the body-core temperature is one of the controlling parameters for this process:

1. Upon the therapy duration elapsing, PHTS 100 preferably enters the subject body cooling phase.
2. PHTS 100 preferably drives the subject body-core average temperature to 37° C. while staying within the limits of Table 1, Alarm and Warning Conditions.
3. Upon the subject body-core average temperature reaching 37° C., PHTS 100 preferably maintains the body-core average temperature until the operator stops the blood pump, while staying within the limits of Table 1, Alarm and Warning Conditions.

The disposable subsystem 301 is an vital part of PHTS operation. The temperature probe sensor technology chosen preferably is:

1. Accurate to within ±0.1° C. for the entire temperature range from 35° C. through 65° C. It is not necessary that these sensors be linear in operation; however, their operation preferably is predictable enough such that the output can be interpolated or extrapolated by a processor to achieve the accuracy specified above.
2. Intrinsically non-hazardous (other than the bio-hazard resulting from use).
3. Sterilizeable (or procured as a pre-sterilized unit), since some of these probes are implanted into the body mass or immersed in bodily fluids.
4. Small, in order to facilitate implantation. Target size for the probe is a 1.5 millimeters diameter cylinder which tapers immediately to a diameter sufficient only to retain the electrical cabling interface. The geometry and electrical connections to this probe must facilitate placement into various body cavities.
5. Bio-compatible. The temperature sensor must have a bio-compatible coating that allows it to be placed in any body cavity without causing any deleterious effect on the subject.
6. Reliable. A failed sensor can cause the therapy session to be cancelled, postponed, or invalidated. The sensor failure rate preferably is less than 1 for every 10,000 hours of sensor use. Since each sensor is expected to be used for approximately 4 hours, this allows only 1 failure for each 2,500 sensors. Further, since 10 sensors are used in each therapy session, this means that 1 session in 250 may be interrupted by a temperature sensor failure of some type.
7. Inexpensive, since they are disposable.

The pressure sensor 326 is used to monitor the blood pump 330 output. Either insufficient or excessive pressure is a sign of possible serious malfunction. This sensor interface preferably is:

1. Sterile. The actual pump interface coupling is required to be sterile and disposable.
2. Intrinsically non-hazardous. The disposable portion of the sensor interface preferably is non-hazardous (other than the biohazard resulting from use).
3. Inexpensive. The actual pump interface coupling after sterilization and packaging preferably is less than $2.00 each in quantities.

In one embodiment, PHTS 100 is intended for use in an operating-room environment, outside of the sterile field. This device preferably is capable of storage and transport under the following conditions:

1. Ambient temperature range, between −55 to 70° C. (−67 to 158 F.) typically 18° C. (65 F.).
2. Moderate dust
3. Relative humidity, ranging from 0–90%
4. Drop resistant, not exceeding 150 millimeters (6 inches)

In one embodiment, PHTS 100 is used to treat and control Acquired Immune Deficiency Syndrome (AIDS).

In another embodiment, PHTS 100 is used to treat and control cancer. It is thought that hyperthermia works in cancer due to a direct effect upon the mitotic activity of cell growth. Cancer is a rapidly growing tissue with a non-differentiated cell structure. Malignancies that are formed exhibit circulatory collapse after hyperthermia with a stimulation of tumor-modulating factors. Empirically, hyperthermia induces a localization factor that affects the tumor, independent of normal tissue. Other factors which may relate to the effect of WBHT on cancer may include water balance of the entire patient versus water balance within cancerous or virus-infected tissue.

In one embodiment, blood-flow rates of between 2 and 4.5 liters per minute though ECC 300 are provided for.

In one embodiment, whole-body hyperthermia is provided for. In another embodiment, perfusion to a single limb, or even local application of heat to a tumor by perfusion are provided for.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method for using a computerized system for a perfusion hyper/hypothermia treatment of a patient comprising:

obtaining physiological fluid having a temperature;

coupling a plurality of temperature signals to the computerized system, each one of the temperature signals representative of a temperature at a separate one of a plurality of patient locations on or within the patient;

generating at least one temperature value representative of each one of the temperatures;

comparing the at least one temperature value to a set of stored parameters in the computerized system to generate a comparison value;

controlling a change in the temperature of the physiological fluid based on the comparison value;

perfusing the physiological fluid into the patient;

measuring a time difference between a start of treatment time and a current time; and wherein the step of comparing further includes comparing the time difference to a stored parameter in the computerized system.

2. The method according to claim 1, wherein the physiological fluid is blood withdrawn from the patient.

3. The method according to claim 1, further including:

calculating, with the computerized system, at least one temperature differential value based on the temperature values of two or more patient locations; and wherein the step of comparing further includes comparing the temperature differential value to a stored parameter in the computerized system.

4. A method for using a computerized system for a perfusion hyper/hypothermia treatment of a patient comprising:

obtaining physiological fluid having a temperature;

coupling a plurality of temperature signals to the computerized system, each one of the temperature signals representative of a temperature at a separate one of a plurality of patient locations on or within the patient;

generating at least one temperature value representative of each one of the temperatures;

comparing the at least one temperature value to a set of stored parameters in the computerized system to generate a comparison value;

controlling a change in the temperature of the physiological fluid based on the comparison value;

perfusing the physiological fluid into the patient;

calculating, with the computerized system, at least one rate of temperature change value based on a time difference and the temperature values; and wherein the step of comparing further includes comparing the rate of temperature change value to a stored parameter in the computerized system.

5. The method according to claim 4, further including:

calculating, with the computerized system, at least one temperature differential value based on the temperature values of two or more patient locations; and wherein the step of comparing further includes comparing the temperature differential value to a stored parameter in the computerized system.

6. A method for using a computerized system for a perfusion hyper/hypothermia treatment of a patient comprising:

obtaining physiological fluid having a temperature;

coupling a plurality of temperature signals to the computerized system, each one of the temperature signals representative of a temperature at a separate one of a plurality of patient locations on or within the patient;

generating at least one temperature value representative of each one of the temperatures;

comparing the at least one temperature value to a set of stored parameters in the computerized system to generate a comparison value;

controlling a change in the temperature of the physiological fluid based on the comparison value;

perfusing the physiological fluid into the patient;

eliciting and receiving checklist input from a user; and controlling operation of the computerized system based on the checklist input from the user.

7. A method for using a computerized system for a perfusion hyper/hypothermia treatment of a patient comprising:

obtaining physiological fluid having a temperature;

coupling a plurality of temperature signals to the computerized system, each one of the temperature signals representative of a temperature at a separate one of a plurality of patient locations on or within the patient;

generating at least one temperature value representative of each one of the temperatures;

comparing the at least one temperature value to a set of stored parameters in the computerized system to generate a comparison value;

controlling a change in the temperature of the physiological fluid based on the comparison value;

perfusing the physiological fluid into the patient;

repeatedly verifying correct operation of the computerized system with a self-test program.

8. A method for using a computerized system for a perfusion hyper/hypothermia treatment of a patient comprising:

obtaining physiological fluid having a temperature;

coupling a plurality of temperature signals to the computerized system, each one of the temperature signals representative of a temperature at a separate one of a plurality of patient locations on or within the patient;

generating at least one temperature value representative of each one of the temperatures;

comparing the at least one temperature value to a set of stored parameters in the computerized system to generate a comparison value;

controlling a change in the temperature of the physiological fluid based on the comparison value;

perfusing the physiological fluid into the patient;

repeatedly verifying correct coupling of the computerized system to external components with a self-test program.

9. A computerized perfusion hyper/hypothermia treatment method comprising:

providing a physiological fluid having a temperature;

at each of a plurality of times, receiving one or more temperature values each representative of a temperature at a patient location on or within a patient;

comparing the received temperature values to a stored temperature-versus-time profile;

controlling a change in the temperature of the physiological fluid based on the profile; and perfusing the physiological fluid into the patient.

10. The method according to claim 9, further comprising:

eliciting and receiving checklist input from a user; and controls operation of the method based on the checklist input.

11. The method according to claim 9, wherein the physiological fluid is blood withdrawn from the patient, and wherein the blood is perfused back into the patient at a different temperature from that when it was withdrawn based on the profile.

12. The method according to claim 9, further comprising:

pumping the physiological fluid at a flow rate that is based on the stored profile.

13. The method according to claim 9, further comprising:

generating a time-difference value representative of a time difference between a start of treatment time and a current time, wherein the comparing the set of temperature values to the temperature-versus-time profile further includes selecting among a set of stored parameters based on the time-difference value.

14. The method according to claim 9, further comprising:

a self-test program that runs on the computer system to verify correct operation of a computer system that controls the comparing the received temperature values to the stored temperature-versus-time profile.

15. The method according to claim 9, further comprising:

mounting a replaceable physiological-fluid heat-exchanger cartridge to a heat-exchanger structure configured to use replaceable heat-exchanger cartridges;

introducing a heat-exchange medium into the heat-exchanger structure; and circulating the medium in thermal contact with the physiological-fluid heat-exchanger cartridge.

16. The method according to claim 9, further comprising:

mounting a replaceable physiological-fluid pump-interface cartridge having a substantially rigid connector and a physiological-fluid path including a deformable plastic enclosure assembled to the connector to a physiological-fluid pump structure configured to use replaceable pump-interface cartridges to provide mechanical energy to the physiological-fluid-treatment pump interface cartridge, wherein the pump structure and the connector cooperate to provide a predetermined occlusion to the deformable plastic enclosure when the physiological-fluid-pump interface cartridge is attached to the physiological-fluid-pump structure.

17. The method according to claim 9, wherein the physiological fluid is saline.

18. In a perfusion hyper/hypothermia-treatment computer-system used to treat a patient, a method comprising:

holding, in the computer system, a set of stored parameters, the set of stored parameters including a minimum and a maximum temperature parameter, and a minimum and a maximum temperature-rate-of-change parameter;

providing a physiological fluid having a temperature, wherein the physiological fluid is blood withdrawn from the patient;

generating a temperature value representative of temperatures at each of a plurality of patient locations on or within a patient and a temperature-rate-of-change value based on a rate of temperature change of one of the temperatures;

comparing, in the computer system, the temperature value to the minimum and maximum temperature parameters in the computer system to generate temperature comparison values;

comparing, in the computer system, the temperature-rate-of-change value to the minimum and maximum temperature-rate-of-change parameters in the computer system to generate rate comparison values;

exchanging heat with the physiological fluid and controlling a change in the temperature of the physiological fluid based on the temperature and rate comparison values; and perfusing the physiological fluid into the patient.

19. The method according to claim 18, further comprising:

pumping the physiological fluid at a pumping rate controlled by the computer system whereby the physiological fluid is pumped to be perfused into the patient after a temperature change has been affected.

20. The method according to claim 18, wherein computer system is operatively coupled to a heat exchanger adapted to accept a replaceable heat exchanger cartridge, wherein the heat exchanger includes a heat-exchanger structure configured to accept a replaceable heat-exchanger cartridge, the method further comprising:

removing a first replaceable heat-exchanger cartridge; and inserting a second replaceable heat-exchanger cartridge into the heat-exchanger structure; and introducing a heat-exchange medium into the heat-exchanger structure and circulating the medium around or through the second heat-exchanger cartridge.

21. The method according to claim 18, further comprising:

comparing a plurality of different-time received temperature values to a stored temperature-versus-time profile and generating time-profile comparison values, wherein the exchanging heat with the physiological fluid and controlling a change in the temperature of the physiological fluid is further based on the time-profile comparison values.

* * * * *